(12) United States Patent
Xiao et al.

(10) Patent No.: US 7,563,787 B2
(45) Date of Patent: Jul. 21, 2009

(54) SUBSTITUTED PYRAZOLE COMPOUNDS

(75) Inventors: Xiao-Yi Xiao, San Diego, CA (US);
Dinish V. Patel, Fremont, CA (US);
John S. Ward, Redwood City, CA (US);
Mark R. Bray, Oakville (CA); Gregory E. Agoston, Rockville, MD (US);
Anthony M. Treston, Rockville, MD (US)

(73) Assignee: Miikana Therapeutics, Inc., Rockville, MD (US)

( * ) Notice: Subject to any disclaimer, the term of this patent is extended or adjusted under 35 U.S.C. 154(b) by 157 days.

(21) Appl. No.: 11/541,484

(22) Filed: Sep. 29, 2006

(65) Prior Publication Data

US 2007/0142368 A1    Jun. 21, 2007

Related U.S. Application Data

(60) Provisional application No. 60/722,217, filed on Sep. 30, 2005, provisional application No. 60/732,340, filed on Oct. 31, 2005, provisional application No. 60/733,868, filed on Nov. 4, 2005.

(51) Int. Cl.
*A61K 31/535* (2006.01)
*C07D 413/00* (2006.01)

(52) U.S. Cl. .................... 514/231.5; 544/111; 544/333; 514/256

(58) Field of Classification Search ................ 514/256; 544/333
See application file for complete search history.

(56) References Cited

U.S. PATENT DOCUMENTS

| | | | |
|---|---|---|---|
| 4,450,162 A | 5/1984 | Kamioka et al. |
| 5,453,414 A | 9/1995 | Tice et al. |
| 5,525,604 A | 6/1996 | Lee et al. |
| 5,852,023 A | 12/1998 | Schaper et al. |
| 5,916,908 A | 6/1999 | Giese et al. |
| 6,200,977 B1 | 3/2001 | Cushing et al. |
| 6,207,401 B1 | 3/2001 | Plowman et al. |
| 6,432,947 B1 | 8/2002 | Arnaiz et al. |
| 6,462,069 B2 | 10/2002 | Reich et al. |
| 6,528,513 B2 | 3/2003 | Cushing et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,677,337 B2 | 1/2004 | Laufersweiler et al. |
| 6,696,452 B2 | 2/2004 | Davies et al. |
| 6,727,251 B2 | 4/2004 | Bebbington et al. |
| 6,762,179 B2 | 7/2004 | Cochran et al. |
| 6,784,195 B2 | 8/2004 | Hale et al. |
| 6,825,190 B2 | 11/2004 | Moon et al. |
| 6,835,726 B2 | 12/2004 | Cushing |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,875,789 B2 | 4/2005 | Tang et al. |
| 6,989,385 B2 | 1/2006 | Bebbington et al. |
| 6,995,159 B2 | 2/2006 | Chiang et al. |
| 7,008,948 B2 | 3/2006 | Bebbington et al. |
| 7,067,522 B2 | 6/2006 | Pease et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,597 B2 | 10/2006 | Bilodeau et al. |
| 7,115,739 B2 | 10/2006 | Bebbington et al. |
| 7,179,826 B2 | 2/2007 | Bebbington et al. |
| 7,226,923 B2 | 6/2007 | Boyd et al. |
| 7,244,735 B2 | 7/2007 | Straub et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2002/0137755 A1 | 9/2002 | Bilodeau et al. |
| 2003/0064982 A1 | 4/2003 | Davies et al. |
| 2003/0069239 A1 | 4/2003 | Cai et al. |

(Continued)

FOREIGN PATENT DOCUMENTS

JP    6-65237    3/1994

(Continued)

OTHER PUBLICATIONS

Author: Fry et al., Title: Inhibitors of Cyclin-Dependent Kinases as Therapeutic Agents for the Treatment of Cancer, Publ: *Current Opinion in Oncologic, Endocrine and Metabolic Investigational Drugs*, vol./Iss: 2 (1), pp. 40-59, Date: Jan. 1, 2000.

(Continued)

*Primary Examiner*—Rei-tsang Shiao
(74) *Attorney, Agent, or Firm*—King & Spalding LLP

(57) ABSTRACT

Disclosed are protein kinase inhibitors, compositions comprising such inhibitors, and methods of use thereof. More particularly, disclosed are inhibitors of Aurora A (Aurora-2) protein kinase. Also disclosed are methods of treating diseases associated with protein kinases, especially diseases associated with Aurora-2, such as cancer.

6 Claims, No Drawings

U.S. PATENT DOCUMENTS

| | | |
|---|---|---|
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0207873 A1 | 11/2003 | Harrington |
| 2004/0006068 A1 | 1/2004 | Cushing et al. |
| 2004/0009981 A1 | 1/2004 | Bebbington et al. |
| 2004/0023963 A1 | 2/2004 | Cao et al. |
| 2004/0023977 A1 | 2/2004 | Larsen et al. |
| 2004/0049032 A1 | 3/2004 | Charrier et al. |
| 2004/0087789 A1 | 5/2004 | Beauchamp et al. |
| 2004/0097531 A1 | 5/2004 | Ledeboer et al. |
| 2004/0116454 A1 | 6/2004 | Davies |
| 2004/0157893 A1 | 8/2004 | Bebbington et al. |
| 2004/0167141 A1 | 8/2004 | Bebbington et al. |
| 2004/0214814 A1 | 10/2004 | Bebbington et al. |
| 2005/0038023 A1 | 2/2005 | Bebbington et al. |
| 2005/0070561 A1 | 3/2005 | Jung et al. |
| 2005/0113382 A1 | 5/2005 | Jahangir et al. |
| 2005/0192294 A1 | 9/2005 | Rudolph et al. |
| 2006/0004030 A1 | 1/2006 | Ebden et al. |
| 2006/0084650 A1 | 4/2006 | Dong et al. |
| 2006/0106029 A1 | 5/2006 | Ohkubo et al. |
| 2006/0135541 A1 | 6/2006 | Mortlock et al. |
| 2006/0142572 A1 | 6/2006 | Martinez-Botella et al. |
| 2006/0258658 A1 | 11/2006 | Bebbington et al. |
| 2006/0270660 A1 | 11/2006 | Charrier et al. |
| 2007/0004731 A1 | 1/2007 | Mastalerz et al. |
| 2007/0004732 A1 | 1/2007 | Gavai et al. |
| 2007/0004733 A1 | 1/2007 | Chen et al. |
| 2007/0037888 A1 | 2/2007 | Nowak et al. |
| 2007/0142368 A1 | 6/2007 | Xiao et al. |
| 2007/0173516 A1 | 7/2007 | Mortimore et al. |
| 2007/0270444 A1 | 11/2007 | Bebbington et al. |
| 2008/0124384 A1 | 5/2008 | Blum |
| 2008/0161278 A1 | 7/2008 | Thomas et al. |
| 2008/0161330 A1 | 7/2008 | Thomas |
| 2008/0200485 A1 | 8/2008 | Xiao et al. |

FOREIGN PATENT DOCUMENTS

| | | |
|---|---|---|
| WO | WO 00/21955 A1 | 4/2000 |
| WO | WO 00/39101 A1 | 7/2000 |
| WO | WO 02/18346 A1 | 3/2002 |
| WO | WO 02/22601 A1 | 3/2002 |
| WO | WO 02/24667 A1 | 3/2002 |
| WO | WO 02/066461 | 8/2002 |
| WO | WO 2006/055831 | 5/2006 |
| WO | WO 2006/067391 A1 | 6/2006 |
| WO | WO 2006/067614 A2 | 6/2006 |
| WO | WO 2006/070198 A1 | 7/2006 |
| WO | WO 2007/005630 A1 | 1/2007 |
| WO | WO 2007/005631 A1 | 1/2007 |
| WO | WO 2007/005708 A1 | 1/2007 |
| WO | WO 2007/014250 A1 | 2/2007 |

OTHER PUBLICATIONS

Author: Sausville, E., Title: Aurora Kinases Dawn as Cancer Drug Targets, Publ: *Nature Medicine*, vol./Iss: 10 (3), pp. 234-267, Date: Mar. 1, 2004.

Author: Anderson et al., Title: Requirement for Integration of Signals from Two Distinct Phophorylation Pathways for Activation of MAP Kinase, Publ: *Nature*, vol./Iss: 343, pp. 641-653, Date: Feb. 15, 1990.

Author: Andrews et al., Title: Mitotic Mechanics: The Auroras Come Into View, Publ: *Current Opinion in Cell Biology*, vol./Iss: 15, pp. 672-683, Date: Jan. 1, 2003.

Author: Andrews, Paul D., Title: Aurora Kinases: Shining Lights on the Therapeutic Horizon?, Publ: *Oncogene*, vol./Iss: 24, pp. 5005-5015, Date: Jan. 1, 2005.

Author: Biscardi et al., Title: c-Src, Receptor Tyrosine Kinases, and Human Cancer, Publ: *Advances in Cancer Research*, vol./Iss: 76, pp. 61-119, Date: Jan. 1, 1999.

Author: Bjorbaek et al., Title: Divergent Functional Roles for p90$^{rsk}$ Kinase Domains, Publ: *The Journal of Biological Chemistry*, vol./Iss: 270 (32), pp. 18848-18852, Date: Jan. 1, 1995.

Author: Bokemeyer et al., Title: Multiple Intracellular MAP Kinase Signaling Cascades, Publ: *Kidney International*, vol./Iss: 49, pp. 1187-1198, Date: May 1, 1996.

Author: Bolen et al., Title: Activation of pp60$^{c-src}$ Protein Kinase Activity in Human Colon Carcinoma, Publ: *Proceedings of the National Academy of Sciences USA*, vol./Iss: 84, pp. 2251-2255, Date: Apr. 1, 1987.

Author: Crews et al., Title: The Primary Structure of MEK, A Protein Kinase that Phosphorylates the ERK Gene Product, Publ: *Science*, vol./Iss: 258, pp. 478-480, Date: Oct. 16, 1992.

Author: Ditchfield et al., Title: Aurora B Couples Chromosome Alignment with Anaphase by Targeting BubR1, Mad2, and Cenp-E to Kinetochores, Publ: *The Journal of Cell Biology*, vol./Iss: 161 (2), pp. 267-280, Date: Apr. 28, 2003.

Author: Druker et al., Title: Activity of a Specific Inhibitor of the BCR-ABL Tyrosine Kinase in the Blast Crisis of Chronic Myeloid Leukemia and Acute Lymphoblastic Leukemia with the Philadelphia Chromosome, Publ: *The New England Journal of Medicine*, vol./Iss: 344 (14), pp. 1038-1043, Date: Apr. 5, 2001.

Author: Ferrara et al., Title: Vascular Endothelial Growth Factor: Basic Science and Clinical Progress, Publ: *Endocrine Reviews*, vol./Iss: 25 (4), pp. 581-611, Date: Aug. 1, 2004.

Author: Fischer et al., Title: Inhibitors of Cyclin-Dependent Kinases as Anti-Cancer Therapeutics, Publ: *Current Medicinal Chemistry*, vol./Iss: 7, pp. 1213-1245, Date: Jan. 1, 2000.

Author: Frey et al., Title: Involvement of Extracellular Signal-Regulated Kinase 2 and Stress-Activated Protein Kinase/Jun N-Terminal Kinase Activation by Transforming Growth Factor β in the Negative Growth Control of Breast Cancer Cells, Publ: *Cancer Research*, vol./Iss: 57, pp. 628-633, Date: Feb. 15, 1997.

Author: Gomtsyan et al., Title: Design, Synthesis, and Structure—Activity Relationship of 6-Alkynylpyrimidines as Potent Adenosine Kinase Inhibitors, Publ: *Journal of Medicinal Chemistry*, vol./Iss: 45, pp. 3639-3648, Date: Aug. 15, 2002.

Author: Boschelli et al., Title: Small Molecule Inhibitors of Src Family Kinases, Publ: *Drugs of the Future*, vol./Iss: 25 (7), pp. 717-736, Date: Jan. 1, 2000.

Author: Brown et al., Title: Evolutionary Relationships of Aurora Kinases: Implications for Model Organism Studies and the Development of Anti-Cancer Drugs, Publ: *BMC Evolutionary Biology*, vol./Iss: 4 (39), pp. 1-10, Date: Jan. 1, 2004.

Author: Carmena et al., Title: The Cellular Geography of Aurora Kinases, Publ: *Nature*, vol./Iss: 4, pp. 842-854, Date: Nov. 1, 2003.

Author: Carter et al., Title: Inhibition of Drug-Resistant Mutants of ABL, KIT and EGF Receptor Kinases, Publ: *Proceedings of the National Academy of Sciences USA*, vol./Iss: 102 (31), pp. 11011-11016, Date: Aug. 2, 2005.

Author: Castro et al., Title: Involvement of Aurora A Kinase During Meiosis I-II Transition in *Xenopus* Oocytes, Publ: *The Journal of Biological Chemistry*, vol./Iss: 278 (4), pp. 2236-2241, Date: Jan. 1, 2003.

Author: Cheetham et al., Title: Crystal Structure of Aurora-2, an Oncogenic Serine/Threonine Kinase, Publ: *The Journal of Biological Chemistry*, vol./Iss: 277 (45), pp. 42419-42422, Date: Nov. 8, 2002.

Author: Chen et al., Title: Phosphorylation of the c-Fos Transrepression Domain by Mitogen-Activated Protein Kinase and 90-kDa Ribosomal S6 Kinase, Publ: *Proceedings of the National Academy of Sciences USA*, vol./Iss: 90, pp. 10952-10956, Date: Dec. 1, 1993.

Author: Masaki et al., Title: pp60$^{c-src}$ Activation in Hepatocellular Carcinoma of Humans and LEC Rats, Publ: *Hepatology*, vol./Iss: 27 (5), pp. 1257-1264, Date: May 1, 1998.

Author: Molina et al., Title: Profound block in Thymocyte Development in Mice Lacking p56$^{lck}$, Publ: *Nature*, vol./Iss: 357, pp. 161-164, Date: May 14, 1992.

Author: Moodie et al., Title: Complexes of Ras-GTP with Raf-1 and Mitogen-Activated Protein Kinase Kinase, Publ: *Science*, vol./Iss: 260, pp. 1658-1661, Date: Jun. 11, 1993.

Author: Namikawa et al., Title: Akt/Protein Kinase B Prevents Injury-Induced Motoneuron Death and Accelerates Axonal Regeneration, Publ: *The Journal of Neuroscience*, vol./Iss: 20 (8), pp. 2875-2886, Date: Apr. 15, 2000.

Author: Oliver et al., Title: Transforming Growth Factor-α and Epidermal Growth Factor Activate Mitogen-Activated Protein Kinase and Its Substrates in Intestinal Epithelial Cells, Publ: *Proceedings of the Society for Experimental Biology and Medicine*, vol./Iss: 210 (2), pp. 162-170, Date: Nov. 1, 1995.

Author: Raingeaud et al., Title: MKK3- and MKK6-Regulated Gene Expression is Mediated by the p38 Mitogen-Activated Protein Kinase Signal Transduction Pathway, Publ: *Molecular and Cellular Biology*, vol./Iss: 16 (3), pp. 1247-1255, Date: Mar. 1, 1996.

Author: Rosen et al., Title: Analysis of $pp60^{c-src}$ Protein Kinase Activity in Human Tumor Cell Lines and Tissues, Publ: *The Journal of Biological Chemistry*, vol./Iss: 261 (29), pp. 13754-13759, Date: Oct. 15, 1986.

Author: Harrington et al., Title: VX-680, A Potent and Selective Small-Molecule Inhibitor of the Aurora Kinases, Suppresses Tumor Growth in vivo and Addendum (dated Apr. 2007), Publ: *Nature Medicine*, vol./Iss: 10 (3), pp. 262-267, Date: Mar. 1, 2004.

Author: Hauf et al., Title: The Small Molecule Hesperadin Reveals a Role for Aurora B in Correcting Kinetochore-Microtubule Attachment and in Maintaining the Spindle Assembly Checkpoint, Publ: *The Journal of Cell Biology*, vol./Iss: 161 (2), pp. 281-294, Date: Apr. 28, 2003.

Author: Heinrich et al., Title: Inhibition of KIT Tyrosine Kinase Activity: A Novel Molecular Approach to the Treatment of KIT-Positive Malignancies, Publ: *Journal of Clinical Oncology*, vol./Iss: 20 (6), pp. 1692-1703, Date: Mar. 15, 2002.

Author: Khwaja et al., Title: AKT is More Than Just Bad Kinase, Publ: *Nature*, vol./Iss: 401, pp. 33-34, Date: Sep. 2, 1999.

Author: Lutz et al., Title: Overexpression and Activation of the Tyrosine Kinase Src in Human Pancreatic Carcinoma, Publ: *Biochemical and Biophysical Research Communications*, vol./Iss: 243, pp. 503-508, Date: Jan. 1, 1998.

Author: Lynch et al., Title: Increased Expression of the src Proto-Oncogene in Hairy Cell Leukemia and a Subgroup of B-Cell Lymphomas, Publ: *Leukemia*, vol./Iss: 7 (9), pp. 1416-1422, Date: Sep. 1, 1993.

Author: Mani et al., Title: Cyclin-Dependent Kinase Inhibitors: Novel Anticancer Agents, Publ: *Expert Opinion on Investigational Drugs*, vol./Iss: 9 (8), pp. 1849-1870, Date: Aug. 1, 2000.

Author: Rouse et al., Title: A Novel Kinase Cascade Triggered by Stress and Heat Shock that Stimulates MAPKAP Kinase-2 and Phosphorylation of the Small Heat Shock Proteins, Publ: *Cell*, vol./Iss: 78, pp. 1027-1037, Date: Sep. 23, 1994.

Author: Sakai et al., Title: MBD3 and HDAC1, Two Components of the NuRD Complex, are Localized at Aurora-A-Positive Centrosomes in M Phase, Publ: *The Journal of Biological Chemistry*, vol./Iss: 277 (50), pp. 48714-48723, Date: Dec. 13, 2002.

Author: Scrittori et al., Title: pEg2 Aurora-A Kinase, Histone H3 Phosphorylation, and Chromosome Assembly in *Xenopus* Egg Extract, Publ: *The Journal of Biological Chemistry*, vol./Iss: 276 (32), pp. 30002-30010, Date: Aug. 10, 2001.

Author: Sen et al., Title: Amplification/Overexpression of a Mitotic Kinase Gene in Human Bladder Cancer, Publ: *Journal of the National Cancer Institute*, vol./Iss: 94 (17), pp. 1320-1329, Date: Sep. 4, 2002.

Author: Silvaraman et al., Title: Hyperexpression of Mitogen-Activated Protein Kinase in Human Breast Cancer, Publ: *Journal of Clinical Investigation*, vol./Iss: 99 (7), pp. 1478-1483, Date: Apr. 1, 1997.

Author: Soriano et al., Title: Targeted Disruption of the c-src Proto-Oncogene Leads to Osteopetrosis in Mice, Publ: *Cell*, vol./Iss: 64, pp. 693-702, Date: Feb. 22, 1991.

Author: Staley et al., Title: Decreased Tumorigenicity of a Human Colon Adenocarcinoma Cell Line by an Antisense Expression Vector Specific for c-Src[1], Publ: *Cell Growth & Differentiation*, vol./Iss: 8, pp. 269-274, Date: Mar. 1, 1997.

Author: Sternberg et al., Title: Therapeutic Intervention in Leukemias that Express the Activated fms-like Tyrosine Kinase 3 (FLT3): Opportunities and Challenges, Publ: *Current Opinion in Hematology*, vol./Iss: 12, pp. 7-13, Date: Jan. 1, 2004.

Author: Takayanagi et al., Title: Suppression of Arthritic Bone Destruction by Adenovirus-Mediated csk Gene Transfer to Synoviocytes and Osteoclasts, Publ: *The Journal of Clinical Investigation*, vol./Iss: 104 (2), pp. 137-146, Date: Jul. 1, 1999.

Author: Talamonti et al., Title: Increase in Activity and Level of $pp60^{c-src}$ in Progressive Stages of Human Colorectal Cancer, Publ: *Journal of Clinical Investigation*, vol./Iss: 91, pp. 53-60, Date: Jan. 1, 1993.

Author: Warner et al., Title: Targeting Aurora-2 Kinase in Cancer, Publ: *Molecular Cancer Therapeutics*, vol./Iss: 2, pp. 589-595, Date: Jun. 1, 2003.

Author: Whelchel et al., Title: Inhibition of ERK Activation Attenuates Endothelin-Stimulated Airway Smooth Muscle Cell Proliferation, Publ: *American Journal of Respiratory Cell and Molecular Biology*, vol./Iss: 16, pp. 589-596, Date: Jan. 1, 1997.

Author: Wiener et al., Title: Decreased Src Tyrosine Kinase Activity Inhibits Malignant Human Ovarian Cancer Tumor Growth in a Nude Mouse Model, Publ: *Clinical Cancer Research*, vol./Iss: 5, pp. 2164-2170, Date: Aug. 1, 1999.

Author: Wong et al., Title: Molecular Cloning and Nucleic Acid Binding Properties of the GAP-Associated Tyrosine Phosphoprotein p62, Publ: *Cell*, vol./Iss: 69, pp. 551-558, Date: May 1, 1992.

Author: Yuan et al., Title: Frequent Activation of AKT2 and Induction of Apoptosis by Inhibition of Phosphoinositide-3-OH Kinase/Akt Pathway in Human Ovarian Cancer, Publ: *Oncogene*, vol./Iss: 19, pp. 2324-2330, Date: Jan. 1, 2000.

Author: Zhang et al., Title: Aberrant Quantity and Localization of Aurora-B/AIM-1 and Survivin During Megakaryocyte Polyploidization and the Consequences of Aurora-B/AIM-1 Deregulated Expression, Publ: *Blood*, vol./Iss: 103 (10), pp. 3717-3726, Date: May 15, 2004.

Title: International Search Report and Written Opinion for PCT/US08/07288, pp. 1-9, Date: Sep. 12, 2008.

SUBSTITUTED PYRAZOLE COMPOUNDS

CROSS-REFERENCE TO RELATED APPLICATIONS

This application claims the benefit of U.S. Provisional Application No. 60/722,217, filed Sep. 30, 2005, and U.S. Provisional Application No. 60/732,340, filed Oct. 31, 2005, and U.S. Provisional Application No. 60/733,868, filed Nov. 4, 2005, all of which are incorporated herein by reference in their entirety.

FIELD OF THE INVENTION

This invention is directed to protein kinase inhibitors, compositions comprising such inhibitors, and methods of use thereof. More particularly, the invention relates to inhibitors of Aurora A (Aurora-2) protein kinase. The invention also relates to pharmaceutical compositions, as well as to methods of treating diseases associated with protein kinases, especially diseases associated with Aurora A, such as cancer.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor alpha (TNF-alpha)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

In humans, there are three highly related Aurora kinases that are all serine/threonine protein kinases (see Andrews, P. D., et al., Curr. Opin. Cell. Biol. 2003, 15, 672-683; Carmena, M., Earnshaw, W. C., Nat. Rev. Mol. Cell. Biol. 2003, 4, 842-854; Brown, J. R., et al., BMC Evol. Biol. 2004, 4, 39, Andrews, P. D., Oncogene 2005, 24, 5005-5015). Despite the sequence relatedness of Aurora A, B and C, the localization and function of these kinases is quite distinct. As a result, overexpression or activation of each of these kinases can be associated with different disease states, including proliferative diseases such as cancer.

Members of the family demonstrate distinct subcellular localization during mitosis and are degraded by the proteosome following exit from mitosis (Graham et al. (2002) J. Biol. Chem. 277:42419-22). The kinases are often found complexed with other proteins, including cytoskeletal structures.

The Aurora kinases share a conserved C-terminal catalytic domain, with greater variation being observed at the N-terminus. Aurora A (Aurora-2) is unique in the presence of two lysine residues in the nucleotide-binding domain of the kinase (Warner et al. (2003) Molecular Cancer Therapeutics 2:589-95).

Maximum levels of the Aurora A polypeptide, and maximum Aurora A activity, are observed at the $G_2$/M transition leading into mitotic prophase, with the polypeptide localizing to the mitotic spindle pole (Graham et al. (2002) J. Biol. Chem. 277:42419-22; Sakai et al. (2002) J. Biol. Chem. 277: 48714-23). Aurora A appears to regulate chromosome duplication with aberrant expression being associated with aneuploidy and an aggressive clinical phenotype, particularly in solid tumors. Such observations, and additional experimental data, suggest that Aurora A disrupts the signaling cascade that regulates chromosome segregation (Sen et al. (2002) J. Nat. Cancer. Inst. 94:1320-29).

Aurora A also appears to function in meiosis, likely in separating homologous chromosomes and in spindle rotation. Injection of antibodies against Aurora A into *Xenopus* oocytes prevents first polar body extrusion and causes arrest at meiosis I (Castro et al. (2003) J. Biol. Chem. 2236-41). The *Xenopus* kinesin-like protein, Eg5, is known to be a substrate for Aurora-2 (Castro et al. (2003) J. Biol. Chem. 2236-41).

In addition, in vitro studies show that Aurora A is incorporated into chromatin and phosphorylates histone H3, and possibly histone H2B (Scrittori et al. (2001) J. Biol. Chem. 276:30002-10). H3 phosphorylation, e.g., at serine-10, during chromosome assembly, appears to be a conserved event in eukaryotic cell division. Inhibition of H3 phosphorylation leads to chromosome condensation, abnormal segregation, and the loss of chromosomes during mitosis and meiosis (Scrittori et al. (2001) J. Biol. Chem. 276:30002-10).

Accordingly, the emerging model for histone phosphorylation is analogous to that of histone acetylation, wherein partially redundant enzymatic activities are associated with histone modifications but different enzymes may function in different cellular contexts. For example, some enzymes may modify histones in bulk, while other enzymes modify histones in a targeted manner, ie., in a sequence or domain-specific manner in the context of assembled chromatin (see, e.g., Scrittori et al. (2001) J. Biol. Chem. 276:30002-10). According to this model, Aurora A would appear to be a kinase responsible for targeted histone modification, in the context of assembled or assembling chromatin.

Other members of the Aurora kinase family are also associated with mitosis and meiosis. Aurora B, like Aurora A, is involved in distinct protein phosphorylation events that regulate the cell cycle. Unlike Aurora A, Aurora B is localized to inner-centromeric chromatin from prophase until the metaphase-anaphase transition, relocalizes to the microtubules in the spindle midzone during telophase, and subsequently is found in the midbody throughout cytokinesis (See Andrews, P. D., Oncogene 2005, 24, 5005-5015, loc. cit.). The function of Aurora B is to ensure accurate chromosome segregation and appropriate cytokinesis. Aurora B appears to associate with a survivin, a polypeptide that associates with the inner centromere and undergoes a significant degree of stretching during mitosis. Survivin appears to be involved with inhibition of apoptosis as well as cell cycle control. Interestingly, both Aurora B and survivin are delocalized during megakaryocyte endomitosis, a process by which late anaphase and cytokinesis are skipped, leading to megakaryocyte polyploidy (Zhang et al. (2004) *Blood* 103:3717-26). Inhibitors of this function in a proliferative disease such as cancer would lead to stasis and cell death, making such inhibitors useful in cancer chemotherapy.

Aurora C (Aurora-3) is the least studied, known member of the family. Aurora C localizes to centrosomes from anaphase until telophase (or even cytokinesis), and is highly expressed in the testis (Brown et al. (2004) *BMC Evolutionary Biology* 4:39).

As noted above, Aurora kinases are overexpressed in certain types of cancers, including colon, breast, and other solid-tumor cancers. The genes encoding the Aurora B and A kinases tend to be amplified in certain types of cancers, while the gene encoding the Aurora C kinase resides in a region of the chromosome that is subject to rearrangement and deletion. Aurora A has been associated with a variety of malignancies, including primary colon, colorectal, breast, stomach, ovarian, prostate, and cervical cancer, neuroblastoma, and other solid-tumor cancers (Warner et al. (2003) *Molecular Cancer Therapeutics* 2:589-95).

Inhibitors of Aurora A have been described. For example, Harrington et al. ((2004) *Nat. Med.* 10:262-67) have described VX-680, a small-molecule inhibitor that blocks cell-cycle progression and induces apoptosis in certain types of tumors in in vivo xenograft models. A pyrazole Aurora A kinase inhibitor is also described in U.S. Pat. No. 6,653,301 (Bebbington et al., issued Nov. 25, 2003).

Hauf et al. ((2003) *J. Cell. Biol.* 161:281-294) identified the indolinone (Hesperadin) as an inhibitor of Aurora B, which causes cells to enter anaphase with monooriented chromosomes, having both sister kinetochores attached to a single spindle pole (a condition known as syntelic attachment).

Ditchfield et al. ((2003) *J. Cell. Biol.* 161:267-280) described ZM447439 ((4-(4-(N-benzoylamino)anilino)-6-methoxy-7-(3-(1-morpholino)propoxy)quina-zoline), an Aurora kinase inhibitor which interferes with chromosome alignment, segregation, and cytokinesis.

Accordingly, kinase inhibitors, particularly inhibitors of Aurora kinases, are of particular interest in treating certain disorders, including cancer. Compounds exhibiting such inhibition are of particular value.

SUMMARY OF THE INVENTION

The present invention provides compounds or pharmaceutically acceptable derivatives or prodrugs thereof, compositions, and methods for treating diseases mediated by kinases. Such diseases include primary, secondary, and metastatic cancers such as melanoma, lymphoma, leukemia, colon, colorectal, breast, lung, kidney, pancreatic, renal, CNS, stomach, ovarian, prostate, cervical, and neuroblastoma.

These compounds have the general formula I:

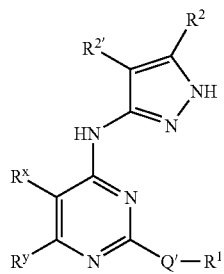

Formula I or a pharmaceutically acceptable derivative or prodrug thereof, wherein:

$R^x$ and $R^y$ are independently selected from the group consisting of -T-$R^3$ and -L-Z-$R^3$;

Q' is selected from the group consisting of —$CR^{6''}$=$CR^{6''}$— and —=—, wherein said —$CR^{6''}$=$CR^{6''}$— may be a cis or trans double bond or a mixture thereof;

$R^1$ is -T-(Ring D);

Ring D is a 5-7 membered monocyclic ring or 8-10 membered bicyclic ring selected from the group consisting of aryl, heteroaryl, heterocyclyl, and carbocyclyl, said heteroaryl or heterocyclyl ring having 1-4 ring heteroatoms selected from the group consisting of nitrogen, oxygen, and sulfur, wherein each substitutable ring carbon of Ring D is independently substituted by oxo, -T-$R^5$, or -V-Z-$R^5$, and each substitutable ring nitrogen of Ring D is independently substituted by —$R^4$;

T is a valence bond or —(C($R^{6'}$)$_2$)-A-;

A is a valence bond or a $C_1$-$C_3$ alkylidene chain wherein a methylene unit of said $C_{1-3}$ alkylidene chain is optionally replaced by —O—, —S—, —N($R^4$)—, —Co—, —CONH—, —NHCO—, —$SO_2$—, —$SO_2$NH—, —$NHSO_2$—, —$CO_2$—, —OC(O)—, —OC(O)NH—, or —$NHCO_2$—;

Z is a $C_{1-4}$ alkylidene chain;

L is selected from the group consisting of —O—; —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, and —C($R^6$)$_2$N($R^6$)CON($R^6$)—;

$R^2$ and $R^{2'}$ are independently selected from the group consisting of —R and -T-W—$R^6$, or $R^2$ and $R^2$ taken together with their intervening atoms form a fused, 5-8 membered, unsaturated or partially unsaturated ring having 0-3 ring heteroatoms selected from the group consisting of nitrogen, oxygen, and sulfur, wherein each substitutable ring carbon of said fused ring formed by $R^2$ and $R^{2'}$ is independently substituted by halo, oxo, —CN, —$NO_2$, $R^7$, or —V—$R^6$, and each substitutable ring nitrogen of said ring formed by $R^2$ and $R^{2'}$ is independently substituted by —$R^4$;

$R^3$ is selected from the group consisting of —R, -halo, —OR, —C(=O)R, —$CO_2$R, —COCOR, —$COCH_2$COR, —$NO_2$, —CN, —S(O)R, —S(O)$_2$ R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$) $SO_2$N($R^7$)$_2$, —N($R^4$)$SO_2$R, and —OC(=O)N(R)$_2$;

each R is independently hydrogen or an optionally substituted group selected from the group consisting of $C_{1-6}$ aliphatic, $C_{6-10}$ aryl, a heteroaryl ring having 5-10 ring atoms, and a heterocyclyl ring having 5-10 ring atoms;

each $R^4$ is independently selected from the group consisting of —$R^7$, —$COR^7$, —$CO_2$(optionally substituted $C_{1-6}$ aliphatic), —CON($R^7$)$_2$, and —$SO_2R^7$;

each $R^5$ is independently selected from the group consisting of —R, halo, —OR, —C(=O)R, —$CO_2$R, —COCOR, —$NO_2$, —CN, —S(O)R, —$SO_2$ R, —SR, —N($R^4$)$_2$, —CON($R^4$e), —$SO_2$N($R^4$), —OC(=O)R, —N($R^4$)COR, —N($R^4$) $CO_2$ (optionally substituted $C_{1-6}$ aliphatic), —N($R^4$)N($^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, and —OC(=O)N($R^4$)$_2$;

V is selected from the group consisting of —O—, —S—, —SO—, —SO$_2$—, —N(R$^6$)SO$_2$—, —SO$_2$N(R$^6$)—, —N(R)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, and —C(R$^6$)$_2$N(R$^6$)CON(R$^6$)—;

W is selected from the group consisting of —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, and —CON(R$^6$)—;

each R$^6$ is independently selected from the group consisting of hydrogen and an optionally substituted C$_{1-4}$ aliphatic group, or two R$^6$ groups on the same nitrogen atom may be taken together with the nitrogen atom to form a 3-6 membered heterocyclyl or heteroaryl ring;

each R$^{6'}$ is independently selected from the group consisting of hydrogen and a C$_{1-4}$ aliphatic group, or two R$^{6'}$ on the same carbon atom are taken together to form a 3-8 membered carbocyclic ring;

each R$^{6''}$ is independently selected from the group consisting of hydrogen, a C$_{1-4}$ aliphatic group, halogen, optionally substituted aryl, and optionally substituted heteroaryl, or two R$^{6''}$ on adjacent carbon atoms are taken together to form a 5-7 membered carbocyclic ring; and each R$^7$ is independently selected from the group consisting of hydrogen and an optionally substituted C$_{1-6}$ aliphatic group, or two R$^7$ on the same nitrogen are taken together with the nitrogen to form a 5-8 membered heterocyclyl or heteroaryl ring.

DETAILED DESCRIPTION

As used herein, the following definitions shall apply unless otherwise indicated. The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "acetamido" refers to the group —NHC(=O)CH$_3$.

The term "aliphatic" as used herein means straight-chain, branched or cyclic C$_1$-C$_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C$_3$-C$_{12}$ hydrocarbons which are completely saturated or which contain one or more units of unsaturation, but which are not aromatic.

The term "amino" refers to an NH$_2$ group.

The term "alkylamino" refers to an amino group wherein one of the hydrogen atoms is replaced by an alkyl group.

The term "dialkylamino" refers to an amino group wherein the hydrogen atoms are replaced by alkyl groups, wherein the alkyl group may be the same or different.

The terms "haloalkyl", "haloalkenyl" and "haloalkoxy" means alkyl, alkenyl or alkoxy, as the case may be, substituted with one or more halogen atoms.

The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having six to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a nonaromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido [3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on any unsaturated carbon atom of an aryl, heteroaryl, aralkyl, or heteroaralkyl group include a halogen, —$R^O$, —$OR^O$, —$SR^O$, 1,2-methylene-dioxy, 1,2-ethylenedioxy, protected OH (such as acyloxy), phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —$N(R^O)_2$, —$NR^OC(O)R^O$, —$NR^OC(O)N(R^O)_2$, —$NR^OCO_2R^O$, —$NR^ONR^OC(O)R^O$, —$NR^ONR^OC(O)N(R^O)_2$, —$NR^ONR^OC_2R^O$, —$C(O)C(O)R^O$, —$C(O)CH_2C(O)R^O$, —$CO_2R^O$, —$C(O)R^O$, —$C(O)N(R^O)_2$, —$OC(O)N(R^O)_2$, —$S(O)_2R^O$, —$SO_2N(R^O)_2$, —$S(O)R^O$, —$NR^OSO_2N(R^O)_2$, —$NR^OSO_2R^O$, —$C(=S)N(R^O)_2$, —$C(=NH)$—$N(R^O)_2$, —$(CH_2)_yNHC(O)R^O$, and —$(CH_2)_yNHC(O)CH(V—R^O)(R^O)$; wherein each $R^O$ is independently selected from hydrogen, a substituted or unsubstituted aliphatic group, an unsubstituted heteroaryl or heterocyclic ring, phenyl (Ph), substituted Ph, —O(Ph), substituted —O(Ph), —$CH_2$ (Ph), or substituted —$CH_2$(Ph); y is 0-6; and V is a linker group. Examples of substituents on the aliphatic group or the phenyl ring of $R^O$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

An aliphatic group or a non-aromatic heterocyclic ring or a fused aryl or heteroaryl ring may contain one or more substituents. Examples of suitable substituents on any saturated carbon of an aliphatic group or of a non-aromatic heterocyclic ring or a fused aryl or heteroaryl ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$ (alkyl), or =NR*, where each R* is independently selected from hydrogen, an unsubstituted aliphatic group, or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

Suitable substituents on the nitrogen of a non-aromatic heterocyclic ring include —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^+)_2$, —$C(=NH)$—$N(R^+)_2$, and —$NR^+SO_2R^+$; wherein each $R^+$ is independently selected from hydrogen, an aliphatic group, a substituted aliphatic group, phenyl (Ph), substituted Ph, —O(Ph), substituted —O(Ph), —$CH_2$(Ph), substituted —$CH_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl.

The term "linker group" or "linker" means an organic moiety that connects two parts of a compound. Linkers are typically comprised of an atom such as oxygen or sulfur, a unit such as —NH—, —$CH_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated $C_{1-6}$ alkylidene chain which is optionally substituted, and wherein one or two saturated carbons of the chain are optionally replaced by —C(O)—, —C(O)C(O)—, —CONH—, —CONHNH—, —$CO_2$—, —OC(O)—, —$NHCO_2$—, —O—, —NHCONH—, —OC(O)NH—, —NHNH—, —NHCO—, —S—, —SO—, —$SO_2$—, —NH—, —$SO_2NH$—, or —$NHSO_2$—

The term "alkylidene chain" refers to an optionally substituted, straight or branched carbon chain, that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept in the dark at a temperature of 40° C. or less, in the absence of moisture or other chemically reactive conditions, for at least a week.

It is understood that in all substituted groups defined herein, polymers arrived at by defining substituents with further substituents to themselves (e.g., substituted phenyl having a substituted phenyl as a substituent which is itself substituted with a substituted phenyl, etc.) are not intended for inclusion herein. In such cases, the maximum number of such substituents is three. For example phenyl substituted with a substituted phenyl is limited to -substituted phenyl-(substituted phenyl)-(substituted phenyl).

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of formula I, or salts thereof, may be formulated into compositions. In a preferred embodiment, the composition is a pharmaceutical composition. In one embodiment, the composition comprises an amount of the protein kinase inhibitor effective to inhibit a protein kinase in a biological sample or in a patient. Compounds of this invention and pharmaceutical compositions thereof, which comprise an amount of the protein kinase inhibitor effective to treat or prevent a kinase mediated condition and a pharmaceutically acceptable carrier, adjuvant, or vehicle, may be formulated for administration to a patient.

Another aspect of this invention relates to a method of treating or preventing a kinase mediated disease. In one embodiment, the disease is a Aurora A-mediated disease, which method comprises administering to a patient in need of such a treatment a therapeutically effective amount of a compound of formula I or a pharmaceutical composition thereof.

The term "Aurora A-mediated disease" or "Aurora A-mediated condition", as used herein, means any disease or other deleterious condition in which Aurora is thought to play a role. The terms "Aurora A-mediated disease" or "Aurora A-mediated condition" also mean those diseases or conditions that are alleviated by treatment with an Aurora A inhibitor. Such conditions include cancer.

The term "cancer" includes, but is not limited to, solid tumors and blood borne tumors and include, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. The term "cancer" includes primary cancer, cancers secondary to treatment, and metastatic cancers.

An aspect of the invention relates to compounds and compositions that are useful for treating cancer.

Another aspect of the invention relates to the treatment of the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another aspect of the invention is a method for treating cancer comprising administering one or more of the compounds described herein to a patient with cancer.

Angiogenesis is characterized by the proliferation of endothelial cells to form new blood vessels (often called neovascularization). Inhibition of mitosis of endothelial cells results in inhibition of angiogenesis. Another aspect of this invention therefore relates to inhibition of undesirable mitosis, including undesirable angiogenesis. A mammalian disease characterized by undesirable cell mitosis, as defined herein, includes, but is not limited to, excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease).

Other undesired angiogenesis involves normal processes including ovulation and implantation of a blastula. The compositions described above can be used as a birth control agent by reducing or preventing uterine vascularization required for embryo implantation. Accordingly, the compositions described above can be used to block ovulation and implantation of a blastula or to block menstruation (induce amenorrhea).

Diseases associated with undesirable mitosis including neovascularization can be treated according to the present invention. Such diseases include, but are not limited to, ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with undesirable mitosis including neovascularization can be treated according to the present invention. Such diseases include, but are not limited to, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications. Other diseases include, but are not limited to, diseases associated with rubeosis (neovascularization of the iris and the angle) and diseases caused by the abnormal proliferation of fibrovascular or fibrous tissue including all forms of proliferative vitreoretinopathy, whether or not associated with diabetes.

Another aspect of the invention relates to the treatment of inflammatory diseases including, but no limited to, excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

Another aspect of the invention relates to inhibiting Aurora A activity in a biological sample, which method comprises contacting the biological sample with the Aurora A inhibitor of formula I, or a composition thereof.

Another aspect of this invention relates to a method of inhibiting Aurora A activity in a patient, which method comprises administering to the patient a compound of formula I or a composition comprising said compound.

In another aspect of this invention, compounds of formula I are more potent inhibitors of Aurora A compared to Aurora B.

Another aspect of this invention relates to a method of treating or preventing a GSK-3-mediated disease with a GSK-3 inhibitor, which method comprises administering to a patient in need of such a treatment a therapeutically effective amount of a compound of formula I or a pharmaceutical composition thereof.

The terms "GSK-3-mediated disease, or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of .beta.-catenin, which is useful for treating schizophrenia.

Another aspect of the invention relates to inhibiting GSK-3 activity in a biological sample, which method comprises contacting the biological sample with a GSK-3 inhibitor of formula I.

Another aspect of this invention relates to a method of inhibiting GSK-3 activity in a patient, which method comprises administering to the patient a compound of formula I or a composition comprising said compound.

Another aspect of this invention relates to a method of treating or preventing a CDK-2-mediated disease with a CDK-2 inhibitor, which method comprises administering to a patient in need of such a treatment a therapeutically effective amount of a compound of formula I or a pharmaceutical composition thereof.

The terms "CDK-2-mediated disease" or CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, such as are described for example in Fischer, P. M. and Lane, D. P., Current Medicinal Chemistry, 7, 1213-1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40-59 (2000).

Another aspect of the invention relates to inhibiting CDK-2 activity in a biological sample or a patient, which method comprises administering to the patient a compound of formula I, or a composition comprising said compound.

Another aspect of this invention relates to a method of treating or preventing an ERK-2-mediated diseases with an ERK-2 inhibitor, which method comprises administering to a patient in need of such a treatment a therapeutically effective amount of a compound of formula I or a pharmaceutical composition thereof. The terms "ERK-mediated disease" or "ERK-mediated condition", as used herein mean any disease or other deleterious condition in which ERK may play a role. The terms "ERK-2-mediated disease" or "ERK-2-mediated condition" also mean those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. ERK-2 protein kinase and its implication in various diseases has been described for example in Bokemeyer et al. 1996, Kidney Int. 49, 1187; Anderson et al., 1990, Nature 343, 651; Crews et al., 1992, Science 258, 478; Bjorbaek et al., 1995, J. Biol. Chem. 270, 18848; Rouse et al., 1994, Cell 78, 1027; Raingeaud et al., 1996, Mol. Cell. Biol. 16, 1247; Raingeaud et al. 1996; Chen et al., 1993 Proc. Natl. Acad. Sci. USA 90, 10952; Oliver et al., 1995, Proc. Soc. Exp. Biol. Med. 210, 162; Moodie et al., 1993, Science 260, 1658; Frey and Mulder, 1997, Cancer Res. 57, 628; Sivaraman et al., 1997, J. Clin. Invest. 99, 1478; Whelchel et al., 1997, Am. J. Respir. Cell Mol. Biol. 16, 589.

Another aspect of the invention relates to inhibiting ERK-2 activity in a biological sample or a patient, which method comprises administering to the patient a compound of formula I, or a composition comprising said compound.

Another aspect of this invention relates to a method of treating or preventing an AKT-mediated diseases with an AKT inhibitor, which method comprises administering to a patient in need of such a treatment a therapeutically effective amount of a compound of formula I or a pharmaceutical composition thereof.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described for example in Khwaja, A., Nature, pp. 33-34, 1990; Zang, Q. Y., et al, Oncogene, 19 2000; Kazuhiko, N., et al, The Journal of Neuroscience, 20 2000.

Another aspect of the invention relates to inhibiting AKT activity in a biological sample or a patient, which method comprises administering to the patient a compound of formula I, or a composition comprising said compound.

Another aspect of this invention relates to a method of treating or preventing a Src-mediated disease with a Src inhibitor, which method comprises administering to a patient in need of such a treatment a therapeutically effective amount of a compound of formula I or a pharmaceutical composition thereof.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described for example in Soriano, Cell, 69, 551 (1992); Soriano et al., Cell, 64, 693 (1991); Takayanagi, J. Clin. Invest., 104, 137 (1999); Boschelli, Drugs of the Future 2000, 25(7), 717, (2000); Talamonti, J. Clin. Invest., 91, 53 (1993); Lutz, Biochem. Biophys. Res. 243, 503 (1998); Rosen, J. Biol. Chem., 261, 13754 (1986); Bolen, Proc. Natl. Acad. Sci. USA, 84, 2251 (1987); Masaki, Hepatology, 27, 1257 (1998); Biscardi, Adv. Cancer Res., 76, 61 (1999); Lynch, Leukemia, 7, 1416 (1993); Wiener, Clin. Cancer Res., 5, 2164 (1999); Staley, Cell Growth Diff., 8, 269 (1997).

Another aspect of the invention relates to inhibiting Src activity in a biological sample or a patient, which method comprises administering to the patient a compound of formula I, or a composition comprising said compound.

Another aspect of this invention relates to a method of treating or preventing an Lck-mediated disease with an Lck inhibitor, which method comprises administering to a patient in need of such a treatment a therapeutically effective amount of a compound of formula I, or a pharmaceutical composition thereof.

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described for example in Molina et al., Nature, 357, 161 (1992).

Another aspect of the invention relates to inhibiting Lck activity in a biological sample or a patient, which method comprises administering to the patient a compound of formula I, or a composition comprising said compound.

Another aspect of this invention relates to a method of treating or preventing an Abl-mediated disease with an Abl inhibitor, which method comprises administering to a patient in need of such a treatment a therapeutically effective amount of a compound of formula I, or a pharmaceutical composition thereof.

The terms "Abl-mediated disease" or "Abl-mediated condition", as used herein, mean any disease state or other deleterious condition in which Abl is known to play a role. The terms "Abl-mediated disease" or "Abl-mediated condition" also mean those diseases or conditions that are alleviated by treatment with an Abl inhibitor. Abl-mediated diseases or conditions include, but are not limited to, leukemias, particularly chronic myeloid leukemia. The association of Abl with various diseases has been described for example in Druker, et al., *N. Engl. J. Med.* 2001, 344, 1038-1042.

Another aspect of the invention relates to inhibiting Abl activity in a biological sample or a patient, which method comprises administering to the patient a compound of formula I, or a composition comprising said compound.

Another aspect of this invention relates to a method of treating or preventing a cKit-mediated disease with an cKit inhibitor, which method comprises administering to a patient in need of such a treatment a therapeutically effective amount of a compound of formula I, or a pharmaceutical composition thereof.

The terms "cKit-mediated disease" or "cKit-mediated condition", as used herein, mean any disease state or other deleterious condition in which cKit is known to play a role. The terms "cKit-mediated disease" or "cKit-mediated condition" also mean those diseases or conditions that are alleviated by treatment with an cKit inhibitor. cKit-mediated diseases or conditions include, but are not limited to, mastocytosis/mast cell leukemia, gastrointestinal stromal tumor, sinonasal natural killer/T-cell lymphoma, seminoma/dysgerminoma, throid carcinoma, samll-cell lung carcinoma, malignant melanoma, adenoid cystic carcinoma, ovarian carcinoma, acute myelogenious leukemia, anaplastic large-cell lymphoma, angiosarcoma, endometrial carcinom, pediatric T-cell ALL/lymphoma, breast carcinoma and prostate carcinoma. The association of cKit with various diseases has been described for example in Heinrich, et al., *J. Clinical Oncology* 2002, 20, 1692-1703.

Another aspect of the invention relates to inhibiting cKit activity in a biological sample or a patient, which method comprises administering to the patient a compound of formula I, or a composition comprising said compound.

Another aspect of this invention relates to a method of treating or preventing a Flt3-mediated disease with an Flt3 inhibitor, which method comprises administering to a patient in need of such a treatment a therapeutically effective amount of a compound of formula I, or a pharmaceutical composition thereof.

The terms "Flt3-mediated disease" or "Flt3-mediated condition", as used herein, mean any disease state or other deleterious condition in which Flt3 is known to play a role. The terms "Flt3-mediated disease" or "Flt3-mediated condition" also mean those diseases or conditions that are alleviated by treatment with an Flt3 inhibitor. Flt3-mediated diseases or conditions include, but are not limited to, acute myelogenous leukemia, mixed lineage leukemia and acute lymphocytic leukemia. The association of Flt3 with various diseases has been described for example in Sternberg and Licht, *Curr. Opin Hematol.* 2004, 12, 7-13.

Another aspect of the invention relates to inhibiting Flt3 activity in a biological sample or a patient, which method comprises administering to the patient a compound of formula I, or a composition comprising said compound.

Another aspect of this invention relates to a method of treating or preventing a KDR-mediated disease with a KDR inhibitor, which method comprises administering to a patient in need of such a treatment a therapeutically effective amount of a compound of formula I, or a pharmaceutical composition thereof.

The terms "KDR-mediated disease" or "KDR-mediated condition", as used herein, mean any disease state or other deleterious condition in which KDR is known to play a role. The terms "KDR-mediated disease" or "KDR-mediated condition" also mean those diseases or conditions that are alleviated by treatment with an KDR inhibitor. KDR-mediated diseases or conditions include, but are not limited to, carcinoma of the lung, breast, gastrointestinal tract, kidney, bladder, ovary and endometrium, intracranial tumors including glioblatoma multiforme, sporadic capillary hemangioblastoma, hematological malignancies, including T cell lymphoma, acute lymphoblastic leukemia, Burkitt's lymphoma and promyelocytic leukemia, age-related macular degeneration, herpetic ocular disease, rheumatoid arthritis, cerebral ischemia and endometriosis. The association of KDR with various diseases has been described for example in Ferrara, *Endocrine Reviews* 2004, 25, 581-611.

Another aspect of the invention relates to inhibiting KDR activity in a biological sample or a patient, which method comprises administering to the patient a compound of formula I, or a composition comprising said compound.

The term "patient" includes human and veterinary subjects.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

An amount effective to inhibit protein kinase, for example, Aurora A, is an amount that causes measurable inhibition of the kinase activity when compared to the activity of the enzyme in the absence of an inhibitor. Any method may be used to determine inhibition, such as, for example, the Biological Testing Examples described below.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

The compositions of the present invention may be administered orally, parenterally, by inhalation, topically, rectally, nasally, buccally, vaginally, transdermally, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, subcutaneously, intraperitoneally or intravenously.

Formulations can be prepared by a variety of techniques known in the art. Examples of formulation techniques can be found in literature publications and in texts such as "Water-insoluble drug formulation", edited by Rong Liu, 2000, Interpharm Press.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The pharmaceutical compositions of this invention may be prepared by techniques known in the art and may be orally administered in any orally acceptable dosage form including, but not limited to, capsules, tablets, aqueous suspensions or solutions. In the case of tablets for oral use, carriers commonly used include but are not limited to celluloses, lactose, or corn starch. Lubricating agents, such as magnesium stearate, are also typically added. For oral administration in a capsule form, useful diluents or carriers include lactose and dried cornstarch. When aqueous suspensions or solutions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared using techniques known in the art including for example by mixing the agent with a suitable non-irritating excipient, which is solid at room temperature but liquid at rectal temperature, and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, the airways, or the lower intestinal tract. Suitable topical formulations are readily prepared for each of these areas or organs using techniques known in the art. For example, topical application for the lower intestinal tract can be effected in a rectal suppository formulation (see above) or in a suitable enema formulation. Topically-transdermal patches may also be used.

For topical or transdermal applications, the pharmaceutical compositions may be formulated by techniques known in the art in a suitable ointment or base containing the active component suspended or dissolved in one or more carriers. Carriers for topical administration of the compounds of this invention are well known in the art and include, but are not limited to, mineral oil, liquid petrolatum, white petrolatum, propylene glycol, polyoxyethylene, polyoxypropylene compound, emulsifying wax, and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated by techniques known in the art as micronized or nanometer-sized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as suspensions or solutions in saline, optionally employing benzyl alcohol or other suitable preservatives, absorption promoters to enhance bioavailability, fluorocarbons, and/or other conventional solubilizing or dispersing agents.

The present invention can be used to treat inflammatory or immune mediated diseases in humans or animals, wherein the inflammatory or immune mediated diseases include, but are not limited to, rheumatoid arthritis, osteoarthritis, ulcerative colitis, Crohn's disease, Mooren's ulcer, arthritis, sarcoidosis, inflammatory or immune mediated bowel disease, systemic lupus, Wegener's syndrome, Stevens-Johnson disease, Behcet's disease, pemphigoid, Lyme's disease, asthma or acquired immune deficiency syndrome.

The present invention can be used to treat infectious diseases in humans or animals, wherein the infectious diseases include, but are not limited to syphilis, a bacterial infection, a Mycobacterial infection, a bacterial ulcer, a fungal ulcer, a Herpes simplex infection, a Herpes zoster infection, a protozoan infection, a Bartonellosis infection, or toxoplasmosis.

The present invention can be used to treat blood or blood vessel diseases in humans or animals, wherein the blood or blood vessel diseases include, but are not limited to, vein occlusion, artery occlusion, carotid obstructive disease, polyarteritis, atherosclerosis, Osler-Weber-Rendu disease, sickle cell anemia, leukemia, acute or chronic neoplastic disease of the bone marrow, hemangiomas, hereditary hemorrhagic telangiectasia, disease of the bone marrow, anemia, impaired blood clotting or enlargement of the lymph nodes, liver, or spleen. The present invention can also be used to treat chronic neoplastic disease of the bone marrow, wherein those diseases include, but are not limited to, multiple myeloma and myelo dysplastic syndrome.

The present invention can be used to treat skin conditions in a humans or an animals, wherein the skin conditions include, but are not limited to, abnormal wound healing, acne rosacea, chemical burns of the skin, dermatitis or psoriasis.

In addition, the invention can be used to treat a variety of post-menopausal symptoms, osteoporosis, cardiovascular disease, myocardial angiogenesis, plaque neovascularization, hemophiliac joints, angiofibroma, wound granulation, intestinal adhesions, scleroderma, hypertrophic scars; i.e., keloids. They are also useful in the treatment of diseases that have angiogenesis as a pathologic consequence, such as cat scratch disease, and *Helicobacter pylori* ulcers. The invention can also be used to treat Alzheimer's disease, to reduce the incidence of stroke, and as an alternative to prior estrogen replacement therapies. The compounds of the present invention can work by estrogenic and non-estrogenic biochemical pathways.

Additionally, the compounds of the present invention can be used to treat endometriosis. Endometriosis is the abnormal growth of endometrial cells; the same cells that line the uterus that are shed monthly in the menstrual process. Wayward endometrial cells can position themselves in the lower abdomen on areas such as the cul-de-sac, the recto-vaginal septum, the stomach, the fallopian tubes, the ovaries, and the bladder. During menstruation, the normal uterine lining is sloughed off and expelled through the vagina, but transplanted endometrial tissue has no means of exiting the body; instead the endometrial tissue and cells adhere and grow where positioned. The results are internal bleeding, inflammation, and scarring. One of the serious consequences of endometrial scarring is infertility. The endometrial growths are generally not malignant or cancerous. Among other complications, the growths can rupture and can spread the endometriosis to new areas of the lower abdomen. Endometriosis is a progressive disease. The growths or lesions are first seen as clear vesicles, then become red, and finally progress to black lesions over a period of seven to ten years.

In addition, the compounds of this invention, can be formulated to increase the bioavailability of the compound by methods well know to those of ordinary skill in the art. Methods of formulating the compounds of this invention and examples of formulations are described in "Water-Insoluble Drug Formulation" Rong Liu editor, CRC Press LLC, 2000, which is incorporated herein by reference in its entirety.

Formulations contemplated as part of this invention include nanoparticles formulations made by controlled precipitation methods and by methods disclosed in U.S. patent application Ser. No. 10/392,403 (Publication No. 2004/0033267), which is hereby incorporated by reference in its entirety. Common excipients for nanoparticles known in the art include water, surface active agents such as sugar polymers (modified celluloses) and detergents, and also optionally preservatives such as benzalkonium salts, benzoic acid or salts thereof, or parabens. By forming nanoparticles, the compositions disclosed herein have increased bioavailability. Preferably, the particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 mm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art. Nanoparticle preparations can be incorporated into many of the formulation approaches described here, including for example suspensions or creams or ointments for topical or transdermal administration, suspensions or powders or tablets or capsules or pellets for suppositories or for oral administration, suspensions for sterile injectable formulations, and polymer formulations.

The compounds that make up this invention can be incorporated into biodegradable or non-biodegradable polymers allowing for sustained release of the compound. The polymers can be implanted so that the drug is delivered parenterally throughout the body or the polymers with the compounds that make up this invention can be implanted in the vicinity of the tumor. A review of polymers in controlled drug delivery can be found for example in "Biodegradable Polymers as Drug Delivery Systems, Chasin M and Langer R (eds), New York, Marcel Dekker, 1990, which is incorporated herein by reference in its entirety. Another review can be found in "Handbook of Biodegradable Polymers", D. Weseman, J. Kost and A. Domb, Taylor & Francis, 1998, which is incorporated herein by reference in its entirety.

A "pharmaceutically acceptable derivative or prodrug" means any pharmaceutically acceptable salt, ester, amide, salt of an ester or amide, or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, the following derivatives of the present compounds: esters, amino acid esters, amino acid amides, phosphate esters, metal salts, sulfonate esters, carbamates, and amides.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase-mediated condition to be treated or prevented, additional therapeutic agents, which are normally administered to treat or prevent that condition, may be administered together with the inhibitors of this invention. For example, in the treatment of cancer, other kinase inhibitors, chemotherapeutic agents, anti-angiogenesis agents, anti-nausea agents, colony-stimulating factors, or other anti-proliferative agents may be combined with the present compounds to treat cancer as is known in the art. These agents include, without limitation, bevacizumab, adriamycin, dexamethasone, vincristine, cyclophosphamide, fluorouracil, topotecan, taxanes, interferons, and platinum derivatives.

Other examples of agents the inhibitors of this invention may also be combined with include, without limitation, agents for treating diabetes such as insulin or insulin analogues, in injectable or inhalation form, glitazones, alpha glucosidase inhibitors, biguanides, insulin sensitizers, and sulfonyl ureas; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; therapeutic antibodies such as bevacizumab; and agents for treating immunodeficiency disorders such as gamma globulin.

Those additional agents may be administered separately from the protein kinase inhibitor-containing composition, or as part of a multiple dosage regimen. Alternatively, those agents may be part of a single dosage form, mixed together with the protein kinase inhibitor of this invention in a single composition.

Compounds of this invention may exist in alternative tautomeric forms, for example as in tautomers shown below. Unless otherwise indicated, the representation of any tautomer is meant to include any other tautomers.

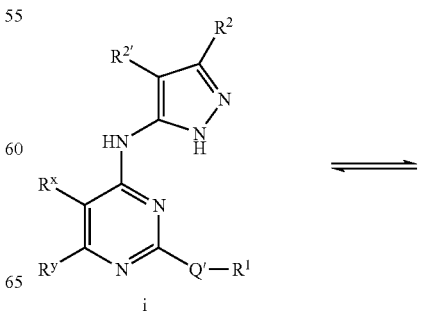

i

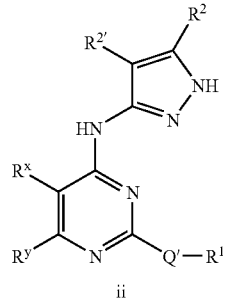

ii

In one embodiment, the present invention provides a compound of formula I or a pharmaceutically acceptable derivative or prodrug thereof,

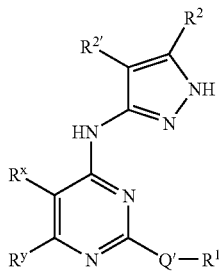

Formula I wherein:

$R^x$ and $R^y$ are independently selected from the group consisting of -T-$R^3$ and -L-Z-$R^3$;

Q' is selected from the group consisting of —$CR^{6''}$=$CR^{6''}$— and —≡—, wherein said —$CR^{6''}$—$CR^{6''}$— may be a cis or trans double bond or a mixture thereof, $R^1$ is -T-(Ring D);

Ring D is a 5-7 membered monocyclic ring or 8-10 membered bicyclic ring selected from the group consisting of aryl, heteroaryl, heterocyclyl, and carbocyclyl, said heteroaryl or heterocyclyl ring having 1-4 ring heteroatoms selected from the group consisting of nitrogen, oxygen, and sulfur, wherein each substitutable ring carbon of Ring D is independently substituted by oxo, -T-$R^5$, or -V-Z-$R^5$, and each substitutable ring nitrogen of Ring D is independently substituted by —$R^4$;

T is a valence bond or —$(C(R^{6'})_2)$-A-;

A is a valence bond or a $C_1$-$C_3$ alkylidene chain wherein a methylene unit of said $C_{1-3}$ alkylidene chain is optionally replaced by —O—, —S—, —N($R^4$)—, —CO—, —CONH—, —NHCO—, —$SO_2$—, —$SO_2$NH—, —$NHSO_2$—, —$CO_2$—, —OC(O)—, —OC(O)NH—, or —$NHCO_2$—;

Z is a $C_{1-4}$ alkylidene chain;

L is selected from the group consisting of —O—, —S—, —SO—, —$SO_2$—, —N(R)$SO_2$—, —$SO_2$N(R)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, and —C($R^6$)$_2$N($R^6$)CON($R^6$)—;

$R^2$ and $R^{2'}$ are independently selected from the group consisting of —R and -T-W—$R^6$, or $R^2$ and $R^{2'}$ taken together with their intervening atoms form a fused, 5-8 membered, unsaturated or partially unsaturated ring having 0-3 ring heteroatoms selected from the group consisting of nitrogen, oxygen, and sulfur, wherein each substitutable ring carbon of said fused ring formed by $R^2$ and $R^{2'}$ is independently substituted by halo, oxo, —CN, —$NO_2$, $R^7$, or -V-$R^6$, and each substitutable ring nitrogen of said ring formed by $R^2$ and $R^{2'}$ is independently substituted by —$R^4$;

$R^3$ is selected from the group consisting of —R, -halo, —OR, —C(=O)R, —$CO_2$R, —COCOR, —COCH$_2$COR, —$NO_2$, —CN, —S(O)R, —S(O)$_2$ R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$) $SO_2$N($R^7$)$_2$, —N($R^4$)$SO_2$R, and —OC(=O)N(R)$_2$;

each R is independently hydrogen or an optionally substituted group selected from the group consisting of $C_{1-6}$ aliphatic, $C_{6-10}$ aryl, a heteroaryl ring having 5-10 ring atoms, and a heterocyclyl ring having 5-10 ring atoms;

each $R^4$ is independently selected from the group consisting of —$R^7$, —$COR^7$, —$CO_2$(optionally substituted $C_{1-6}$ aliphatic), —CON($R^7$)$_2$, and —$SO_2R^7$;

each $R^5$ is independently selected from the group consisting of —R, halo, —OR, —C(=O)R, —$CO_2$R, —COCOR, —$NO_2$, —CN, —S(O)R, —$SO_2$ R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, and —OC(=O)N($R^4$)$_2$;

V is selected from the group consisting of —O—, —S—, —SO—, —$SO_2$—, —N($R^6$)$SO_2$—, —$SO_2$N($R^6$)—, —N(R)—, —CO—, —$CO_2$—, —N($R^6$)CO—, —N($R^6$)C(O)O—, —N($R^6$)CON($R^6$)—, —N($R^6$)SO$_2$ N($R^6$)—, , —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, and —C($R^6$)$_2$N($R^6$)CON($R^6$)—;

W is selected from the group consisting of —C($R^6$)$_2$O—, —C($R^6$)$_2$S—, —C($R^6$)$_2$SO—, —C($R^6$)SO$_2$—, —C($R^6$)$_2$SO$_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, —C($R^6$)$_2$N($R^6$)CON($R^6$)—, and —CON($R^6$)—;

each $R^6$ is independently selected from the group consisting of hydrogen and an optionally substituted $C_{1-4}$ aliphatic group, or two $R^6$ groups on the same nitrogen atom may be taken together with the nitrogen atom to form a 5-6 membered heterocyclyl or heteroaryl ring;

each $R^{6'}$ is independently selected from the group consisting of hydrogen and a $C_{1-4}$ aliphatic group, or two $R^{6'}$ on the same carbon atom are taken together to form a 3-6 membered carbocyclic ring;

each $R^{6''}$ is independently selected from the group consisting of hydrogen, a $C_{1-4}$ aliphatic group, halogen, optionally substituted aryl, and optionally substituted heteroaryl, or two $R^{6''}$ on adjacent carbon atoms are taken together to form a 5-7 membered carbocyclic or heterocyclic ring, or one of the R6" can be taken together with a substituent on ring D to form a fused bicyclic carbocylcic or heterocyclic ring; and each $R^7$ is independently selected from the group consisting of hydrogen and an optionally substituted $C_{1-6}$ aliphatic group, or two $R^7$ on the same nitrogen are taken together with the nitrogen to form a 5-8 membered heterocyclyl or heteroaryl ring.

In one embodiment, the present invention provides a compound of formula Ia or a pharmaceutically acceptable derivative or prodrug thereof,

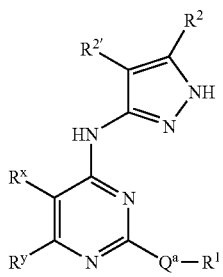

Ia wherein $R^2$, $R^{1'}$, $R^x$, $R^y$, and $R^1$ is defined as in formula I; $Q^a$ is cis or trans —$CR^{6''}$—$CR^{6''}$— or a mixture thereof; and each $R^{6''}$ is independently selected from hydrogen, methyl, halogen, optionally substituted aryl, and optionally substituted heteroaryl.

In some embodiments, the invention provides compounds of formula Ia wherein $Q^a$ is trans —$CR^{6''}$=$CR^{6''}$—.

In another embodiment, the present invention provides a compound of formula Ib or a pharmaceutically acceptable derivative or prodrug thereof,

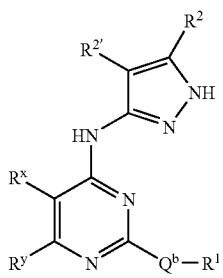

Ib wherein $R^2$, $R^{2'}$, $R^x$, $R^y$, and $R^1$ is defined as in formula I, and $Q^b$ is —≡—.

Preferred $R^x$ groups in the compounds of formula I, Ia, Ib, II, Ia, and IIb include hydrogen, alkyl, amino, nitro, alkyl- or dialkylamino, acetamido, or a $C_{1-4}$ aliphatic group such as methyl, ethyl cyclopropyl, or isopropyl, and most preferably hydrogen and amino.

Preferred $R^y$ groups in the compounds of formula I, Ia, Ib, II, Ia, and IIb include -T-$R^3$ or -L-Z-$R^3$ wherein T is a valence bond or a alkyl (1-6 carbons in length, branched or unbranched) or alkene (1-6 carbons in length, branched or unbranched), L is —O—, —S—, —C(R)$_2$O—, —CO—, C(O)N($R^6$)—, or —N($R^4$)—, and $R^3$ is —R, —N($R^4$)$_2$, or OR. Preferred $R^y$ groups include 5-6 membered heteroaryl or non-aromatic heterocyclic rings, such as 2-pyridyl, 3-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, or 4-methylpiperazinyl, N-acetylpiperizinyl, N-alkylcarboxamidpiperizinyl, N-(methylsulfone)piperizinyl, thiophene, furan, tetrahydrofuran, cyclo[2.2.1]heptenyl; $C_{1-6}$ aliphatic, such as methyl, ethyl, cyclopropyl, isopropyl, or t-butyl; alkoxyalkylamino such as methoxyethylamino; alkoxyalkyl such as methoxymethyl or methoxyethyl; amino, alkyl- or dialkylamino such as ethylamino or dimethylamino; alkyl- or dialkylaminoalkoxy such as dimethylaminopropyloxy; acetamido; alkoxycarbonyl; alkyl- and dialkylamidocarbonyl; and optionally substituted phenyl such as phenyl or halo-substituted phenyl. For amine nitrogens, the N can be in the free base form, a pharmaceutically acceptable salt or the quaternary salt. This invention envisions that R3 can be attached to L or T through either the heteroatom or any ring atom where there is a hydrogen available for ring attachment.

$R^2$ and $R^{2'}$ may be taken together to form a fused ring, thus providing a bicyclic ring system containing a pyrazole ring. Preferred fused rings include benzo, pyrido, pyrimido, a partially unsaturated 6-membered carbocyclo ring, wherein said fused ring is optionally substituted. Fused 5-membered rings are also envisioned and include but are not limited to pyrrolo, tetrahydrofuran, tetrahydrothiofuran imidazolidine and pyrazolidine. These are exemplified in the following formula I compounds having a pyrazole-containing bicyclic ring system, but also apply to compounds of formula Ia and Ib:

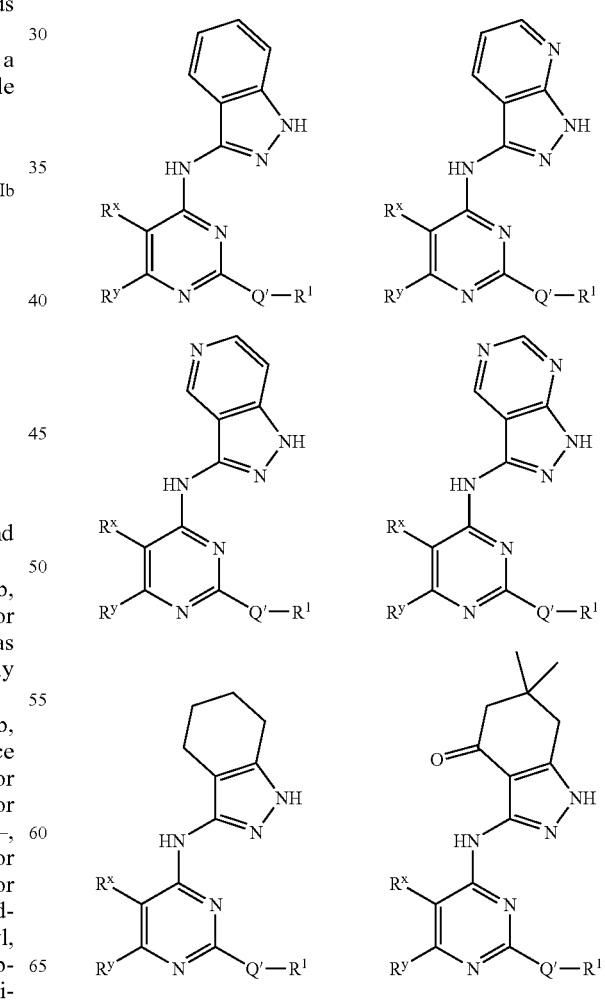

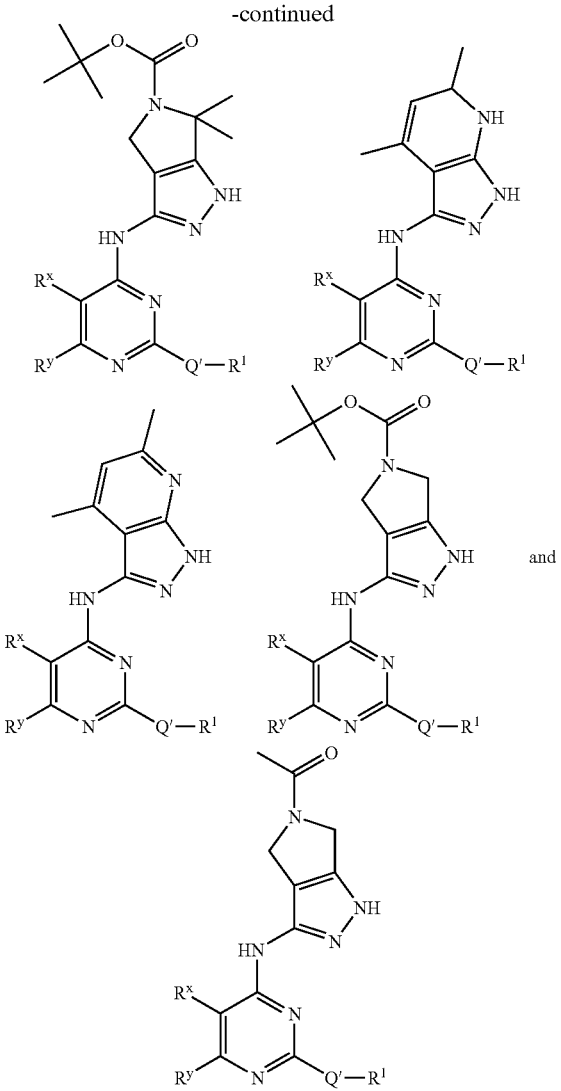

Preferred substituents on the $R^2/R^{2'}$ fused rings include one or more of the following: -halo, —$N(R^4)_2$, —$C_{1-3}$ alkyl, —$C_{1-3}$ haloalkyl, —$NO_2$, —$O(C_{1-3}$ alkyl), —$CO_2(C_{1-3}$ alkyl), —CN, —$SO_2(C_{1-3}$ alkyl), —$SO_2NH_2$, —$OC(O)NH_2$, —$NH_2SO_2(C_{1-3}$ alkyl), —$NHC(O)(C_{1-3}$ alkyl), —$C(O)NH_2$, and —$CO(C_{1-3}$ alkyl), wherein the ($C_{1-3}$ alkyl) is most preferably methyl.

When the pyrazole ring system is monocyclic, preferred $R^2$ groups include hydrogen, $C_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)_2$, $CON(Et)CH_2CH_2CH_3$, $CONHCH_2CH(CH_3)_2$, $CON(n-C_3H_7)_2$, CO(3-methoxymethylpyrrolidin-1-yl), CONH(3-tolyl), CONH(4-tolyl), $CONHCH_3$, CO(morpholin-1-yl), CO(4-methylpiperazin-1-yl), $CONHCH_2CH_2OH$, $CONH_2$, and CO(piperidin-1-yl). A preferred $R^{2'}$ group is hydrogen.

When Ring D of formula I, Ia, or Ib is monocyclic, preferred Ring D groups include optionally substituted phenyl, pyridyl, pyridazinyl, pyrimidinyl, and pyrazinyl.

When Ring D of formula I, Ia, or Ib is bicyclic, preferred optionally substituted bicyclic Ring D groups include naphthyl, tetrahydronaphthyl, indanyl, benzimidazolyl, quinolinyl, indolyl, isoindolyl, indolinyl, benzo[b]furyl, benzo[b]thiophenyl, indazolyl, benzothiazolyl, cinnolinyl, phthalazinyl, quinazolinyl, quinoxalinyl, 1,8-naphthyridinyl and isoquinolinyl.

On Ring D of formula I, Ia, or Ib, preferred $T-R^5$ or $V-Z-R^5$ substituents include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$N(R^4)CO_2R$, —$SO_2N(R^4)_2$, —$N(R^4)SO_2R$, —$N(R^6)COCH_2$ $N(R^4)_2$, —$N(R^6)COCH_2CH_2N(R^4)_2$, and —$N(R^6)COCH_2CH_2CH_2N(R^4)_2$, wherein R is selected from hydrogen, $C_{1-6}$ aliphatic, phenyl, a 5-6 membered heteroaryl ring, or a 5-6 membered heterocyclic ring. More preferred $R^5$ substituents include —Cl, —Br, —F, —CN, —$CF_3$, —COOH, —CONHMe, —CONHEt, —$NH_2$, —NHAc, —$NHSO_2Me$, —$NHSO_2Et$, —$NHSO_2(n\text{-propyl})$, —$NHSO_2(isopropyl)$, —NHCOEt, —$NHCOCH_2NHCH_3$, —$NHCOCH_2N(CO_2$ t-Bu)$CH_3$, —$NHCOCH_2N(CH_3)_2$, —$NHCOCH_2CH_2$ $N(CH_3)_2$, —$NHCOCH_2CH_2CH_2N(CH_3)_2$, —NHCO(cyclopropyl), —NHCO(isobutyl), —$NHCOCH_2$(morpholin-4-yl), —$NHCOCH_2CH_2$(morpholin-4-yl), —NHCO—$CH_2CH_2CH_2$(morpholin-4-yl), —$NHCO_2$(t-butyl), —NH($C_{1-4}$ aliphatic) such as —NHMe, —N($C_{1-4}$ aliphatic)$_2$ such as —$NMe_2$, OH, —O($C_{1-4}$ aliphatic) such as —OMe, $C_{1-4}$ aliphatic such as methyl, ethyl, cyclopropyl, isopropyl, or t-butyl, and —$CO_2$ ($C_{1-4}$ aliphatic).

Preferred formula I compounds have one, two, three, four, five, or all of the features selected from the group consisting of:

(a) $R^x$ is hydrogen, nitro, amino, alkyl- or dialkylamino, acetamido, or a $C_{1-4}$ aliphatic group;

(b) $R^y$ is -$T-R^3$ or -$L-Z-R^3$, wherein T is a valence bond or $AC(R^6)_2$— and $R^3$ is —R, —$N(R^4)_2$, —OR, or —$CO_2R$;

(c) $R^1$ is -T-(Ring D), wherein T is a valence bond or —$C(R^{6'})_2$—;

(d) Ring D is an optionally substituted 5-7 membered monocyclic or an 8-10 membered bicyclic aryl or heteroaryl ring;

(e) $R^2$ is —R or -T-W—$R^6$ and $R^{2'}$ is hydrogen, or $R^2$ and $R^{2'}$ are taken together to form an optionally substituted benzo ring; and (f) each $R^{6''}$ is independently hydrogen, a $C_{1-4}$ aliphatic group, halogen, optionally substituted aryl, or optionally substituted heteroaryl.

More preferred formula I compounds have one, two, three, four, five, six or all of the features selected from the group consisting of:

(a) $R^y$ is -$T-R^3$ or -$L-Z-R^3$ wherein T is a valence bond or —$C(R^{6'})_2$— and $R^3$ is —R, —OR, —$N(R^4)_2$ or —$CO_2R$, wherein R is hydrogen, $C_{1-6}$ aliphatic, 5-6 membered heterocyclyl, 6-membered aryl, or 5-6 membered heteroaryl;

(b) $R^1$ is -T-(Ring D), wherein T is a valence bond or —$C(R6')_2$—;

(c) Ring D is an optionally substituted 5-6 membered monocyclic or an 8-10 membered bicyclic aryl or heteroaryl ring;

(d) $R^2$ is —R and $R^{2'}$ is hydrogen, wherein —R is independently hydrogen or an optionally substituted group selected from the group consisting of $C_{1-6}$ aliphatic, $C_{6-10}$ aryl, a heteroaryl ring having 5-10 ring atoms, and a heterocyclyl ring having 5-10 ring atoms;

(e) L is —O—, —S—, —N($R^4$)—, or —C(O)N($R^6$)—;

(f) Q' is trans —$R^{6''}$=C$R^{6''}$— or —≡—; and (g) each $R^{6''}$ is independently hydrogen, methyl, halogen, optionally substituted aryl, or optionally substituted heteroaryl.

Even more preferred compounds of formula I have one, two, three, four, five, or all of the features selected from the group consisting of:

(a) $R^x$ is hydrogen, methyl, ethyl, propyl, cyclopropyl, isopropyl, amino, dimethylamino, methylamino, nitro, or acetamido;

(b) $R^y$ is selected from 2-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, 4-alkylpiperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, methoxymethyl, —CO$_2$R, and —C(O)N($R^6$)ZR;

(c) $R^1$ is -T-(Ring D), wherein T is a valence bond and Ring D is a 5-6 membered aryl or heteroaryl ring, wherein Ring D is optionally substituted with one to two groups selected from -halo, CF$_3$, —CN, —NO$_2$, —N($R^4$)$_2$, optionally substituted $C_{1-6}$ aliphatic group, —OR, —CO$_2$R, —CONH($R^4$), —N($R^4$)COR, —N($R^4$)SO$_2$R, —N($R^4$)COCH$_2$N($R^6$)$_2$, —N($R^4$)COCH$_2$CH$_2$N($R^6$)$_2$, and —N($R^4$)COCH$_2$CH$_2$CH$_2$N($R^6$)$_2$;

(d) $R^2$ is hydrogen or a substituted or unsubstituted $C_{1-6}$ aliphatic;

(e) Q' is trans —C$R^{6''}$=C$R^{6''}$— or —≡—; and (f) each $R^{6''}$ is independently hydrogen, methyl, chloro, or fluoro.

Particularly more preferred compounds of formula I have one, two, three, four, five, or all of the features selected from the group consisting of:

(a) $R^x$ is hydrogen or amino;

(b) $R^y$ is selected from 2-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, 4-alkylpiperazinyl, alkoxyalkylamino, alkoxyalkyl, alkyl- or dialkylamino, alkyl- or dialkylaminoalkoxy, optionally substituted phenyl, —CO$_2$R, and —C(O)NHZR;

(c) $R^1$ is T-(Ring D), wherein T is a valence bond and Ring D is a 5-6 membered aryl or heteroaryl ring, wherein Ring D is optionally substituted with one to two groups selected from -halogen, —CN, —CF$_3$, —NO$_2$, —N($R^4$)$_2$, optionally substituted $C_{1-6}$ aliphatic group, —OR, —CO$_2$R, —CONH($R^4$), —N($R^4$)COR, —N($R^4$)SO$_2$R, —N($R^4$)COCH$_2$N($R^6$), —N($R^4$)COCH$_2$CH$_2$N($R^6$), and —N($R^4$)COCH$_2$CH$_2$CH$_2$N($R^6$)$_2$;

(d) $R^2$ is hydrogen or a substituted or unsubstituted $C_{1-6}$ aliphatic, and L is —O—, —S—, —NH— or —C(O)NH—;

(e) Q' is trans —C$R^{6''}$=C$R^{6''}$—; and (f) each $R^{6''}$ is independently hydrogen or fluoro.

Preferred formula Ia or Ib compounds have one, two, three, four, five, or all of the features selected from the group consisting of:

(a) $R^x$ is hydrogen, nitro, amino, alkyl- or dialkylamino, acetamido, or a $C_{1-4}$ aliphatic group;

(b) $R^y$ is -T-$R^3$ or -L-Z-$R^3$, wherein T is a valence bond or —C($R^{6'}$)$_2$— and $R^3$ is —R, —N($R^4$)$_2$, —OR, or —CO$_2$R;

(c) $R^1$ is -T-(Ring D), wherein T is a valence bond or —C($R^{6'}$)$_2$—;

(d) Ring D is a 5-7 membered monocyclic or an 8-10 membered bicyclic aryl or heteroaryl ring;

(e) $R^2$ is —R or -T-W—$R^6$ and $R^{2'}$ is hydrogen, or $R^2$ and $R^{2'}$ are taken together to form an optionally substituted benzo ring; and (f) each $R^{6''}$ is independently hydrogen, a $C_{1-4}$ aliphatic group, halogen, optionally substituted aryl, or optionally substituted heteroaryl.

More preferred formula Ia or Ib compounds have one, two, three, four, five, or all of the features selected from the group consisting of:

(a) $R^y$ is -T-$R^3$ or -L-Z-$R^3$ wherein T is a valence bond or —C($R^{6'}$)$_2$— and $R^3$ is —R, —OR, —N($R^4$)$_2$ or —CO$_2$R, wherein R is hydrogen, $C_{1-6}$ aliphatic, 5-6 membered heterocyclyl, 6-membered aryl, or 5-6 membered heteroaryl;

(b) $R^1$ is -T-(Ring D), wherein T is a valence bond or —C($R^{6'}$)$_2$—;

(c) Ring D is a 5-6 membered monocyclic or an 8-10 membered bicyclic aryl or heteroaryl ring;

(d) $R^2$ is —R and $R^{2'}$ is hydrogen, wherein —R is independently hydrogen or an optionally substituted group selected from the group consisting of $C_{1-6}$ aliphatic, $C_{6-10}$ aryl, a heteroaryl ring having 5-10 ring atoms, and a heterocyclyl ring having 5-10 ring atoms;

(e) L is —O—, —S—, —N($R^4$)—, or C(O)N($R^6$)—; and (f) each $R^{6''}$ is independently hydrogen, methyl, halogen, optionally substituted aryl, or optionally substituted heteroaryl.

Even more preferred compounds of formula Ia or Ib have one, two, three, four, or all of the features selected from the group consisting of:

(a) $R^x$ is hydrogen, methyl, ethyl, propyl, cyclopropyl, isopropyl, amino, dimethylamino, methylamino, nitro, or acetamido;

(b) $R^y$ is selected from 2-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, 4-alkylpiperazinyl, methyl, ethyl, cyclopropyl, isopropyl, t-butyl, alkoxyalkylamino, alkoxyalkyl, alkyl- or dialkylamino, alkyl- or dialkylaminoalkoxy, acetamido, optionally substituted phenyl, methoxymethyl, —CO$_2$R, and —C(O)N($R^6$)ZR;

(c) $R^1$ is -T-(Ring D), wherein T is a valence bond and Ring D is a 5-6 membered aryl or heteroaryl ring, wherein Ring D is optionally substituted with one to two groups selected from -halo, CF$_3$, —CN, —NO$_2$, —N($R^4$)$_2$, optionally substituted $C_{1-6}$ aliphatic group, —OR, —CO$_2$R, —CONH($R^4$), —N($R^4$)COR, —N($R^4$)SO$_2$R, —N($R^4$)COCH$_2$N($R^6$)$_2$, —N($R^4$)COCH$_2$CH$_2$N($R^6$)$_2$, and —N($R^4$)COCH$_2$CH$_2$CH$_2$N($R^6$)$_2$;

(d) $R^2$ is hydrogen or a substituted or unsubstituted $C_{1-6}$ aliphatic; and (e) each $R^{6''}$ is independently hydrogen, methyl, chloro, or fluoro.

Particularly more preferred compounds of formula Ia or Ib have one, two, three, four, or all of the features selected from the group consisting of:

(a) $R^x$ is hydrogen or amino;

(b) $R^y$ is selected from 2-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, 4-alkylpiperazinyl, alkoxyalkylamino, alkoxyalkyl, alkyl- or dialkylamino, alkyl- or dialkylaminoalkoxy, optionally substituted phenyl, —CO$_2$R, and C(O)NHZR;

(c) $R^1$ is T-(Ring D), wherein T is a valence bond and Ring D is a 5-6 membered aryl or heteroaryl ring, wherein Ring D is optionally substituted with one to two groups selected from -halogen, —CN, —CF$_3$, —NO$_2$, —N(R$^4$)$_2$, optionally substituted C$_{1-6}$ aliphatic group, —OR, —CO$_2$R, —CONH(R$^4$), —N(R$^4$)COR, —N(R$^4$)SO$_2$R, —N(R$^4$)COCH$_{12}$N(R$^6$)$_2$, —N(R$^4$)COCH$_2$CH$_2$N(R$^6$)$_2$, and —N(R$^4$)COCH$_2$CH$_2$CH$_2$N(R$^6$)$_2$;

(d) R$^2$ is hydrogen or a substituted or unsubstituted C$_{1-6}$ aliphatic, and L is —O—, —S—, —NH— or —C(O)NH—; and (e) each R$^{6''}$ is independently hydrogen or fluoro.

In another embodiment, the present invention provides compounds of formula II or a pharmaceutically acceptable derivative or prodrug thereof:

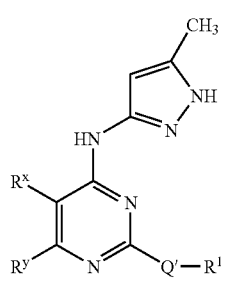

II wherein

R$^x$ is hydrogen, nitro, amino, alkyl- or dialkylamino, acetamido, or a C$_{1-4}$ aliphatic group;

R$^y$ is 2-pyridyl, 4-pyridyl, pyrrolidinyl, piperidinyl, morpholinyl, piperazinyl, 4-alkylpiperazinyl, alkoxyalkylamino, alkoxyalkyl, alkyl- or dialkylamino, alkyl- or dialkylaminoalkoxy, optionally substituted phenyl, —CO$_2$R, or —C(O)NHZR, wherein R is hydrogen, C$_{1-6}$ aliphatic, 5-6 membered heterocyclyl, phenyl, or 5-6 membered heteroaryl and Z is a C$_1$-C$_4$ alkylidene chain;

Q' is —CR$^{6''}$=CR$^{6''}$— or ═ wherein, the —CR$^{6''}$=CR$^{6''}$— may be a cis or trans double bond; and each R$^{6''}$ is independently hydrogen, methyl, halogen, optionally substituted aryl, or optionally substituted heteroaryl; and R$^1$ is phenyl optionally substituted with one to two groups selected from the group consisting of -halogen, —CN, —CF$_3$, —NO$_2$, —N(R$^4$)$_2$, optionally substituted C$_{1-6}$ aliphatic group, —OR, —CO$_2$R, —CONH(R$^4$), —N(R$^4$)COR, —N(R$^4$)SO$_2$R, —N(R$^4$)COCH$_2$N(R$^6$)$_2$, —N(R$^4$)COCH$_2$CH$_2$N(R$^6$)$_2$, and —N(R$^4$)COCH$_2$CH$_2$CH$_2$N(R$^6$)$_2$ wherein R, R$^4$, and R$^6$ are defined as in formula I.

In some embodiments, the invention provides compounds of formula I or II wherein Q' is trans —CH=CH—. In other embodiments, Q' is ═.

In other embodiments of the compounds of formula I or II, R$^x$ is hydrogen.

In still other embodiments, R$^y$ is selected from 2-pyridyl, 4-pyridyl, pyrrolidinyl, piperidinyl, morpholinyl, hydroxypiperidinyl, N-(4-hydroxypiperidin)-yl, O-(4-piperidinyl), piperazinyl, alkylpiperazinyl, 4-alkylpiperazinyl, alkoxyalkylamino, alkoxyalkyl, alkyl- or dialkylamino, alkyl- or dialkylaminoalkoxy, optionally substituted phenyl, —CO$_2$R, and —C(O)NHZR.

In some embodiments, R$^y$ is 4-alkylpiperazinyl. In other embodiments R$^y$ is 4-methylpiperazinyl.

In some embodiments R$^y$ is hydroxypiperidinyl. In other embodiments R$^y$ is N-(4-hydroxypiperidin)-yl or O-(4-piperidinyl).

In one embodiment, the present invention provides compounds of formula IIa or a pharmaceutically acceptable derivative or prodrug thereof:

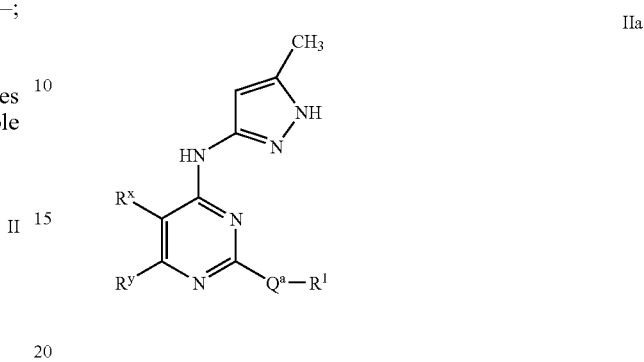

IIa wherein R$^x$, R$^y$, and R$^1$ are as defined as in formula II; Q$^a$ is cis or trans —CR$^{6''}$=CR$^{6''}$— or a mixture thereof; and each R$^{6''}$ is independently selected from hydrogen, methyl, halogen, optionally substituted aryl, and optionally substituted In some embodiments of compound of formula IIa, Q$^a$ is cis —CR$^{6''}$=CR$^{6''}$—.

In other embodiments, Q$^a$ is trans —CR$^{6''}$=CR$^{6''}$—.

In one embodiment, the present invention provides compounds of formula IIa or a pharmaceutically acceptable derivative or prodrug thereof:

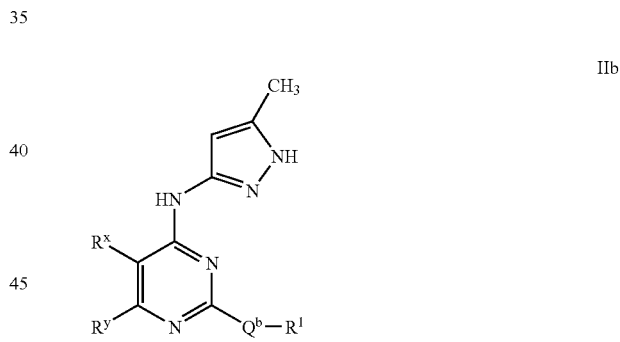

IIb wherein R$^x$, R$^y$, and R$^1$ are as defined as in formula II and Q$^b$ is ═.

In some embodiments, the invention provides compounds of formula I, Ia, Ib, II, IIa, or IIb wherein R$^1$ is selected from the following group:

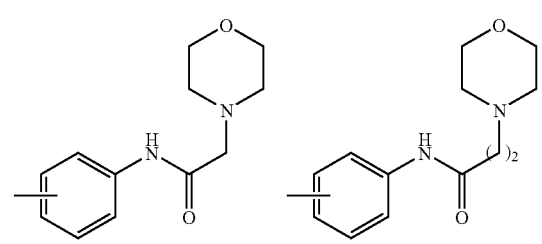

-continued
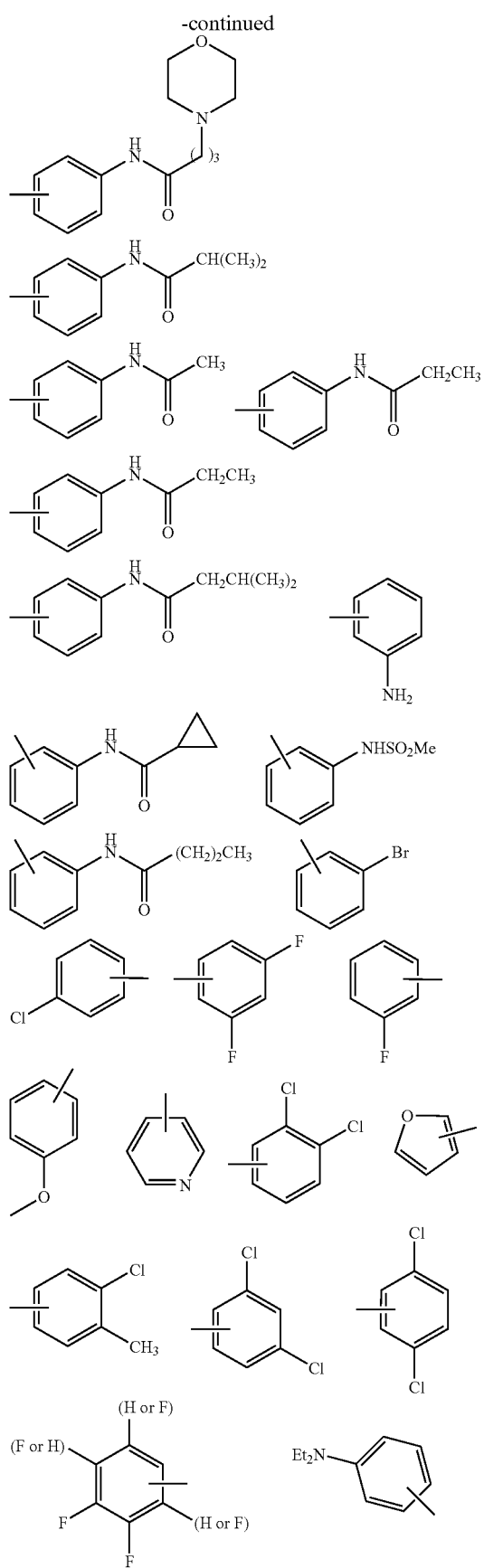
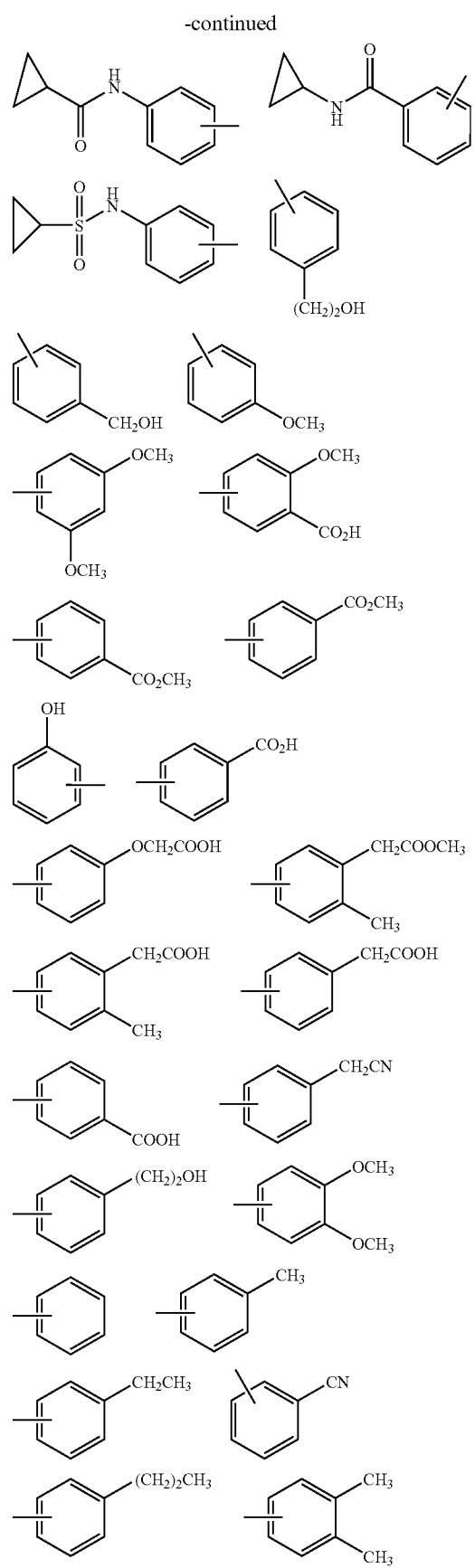

-continued

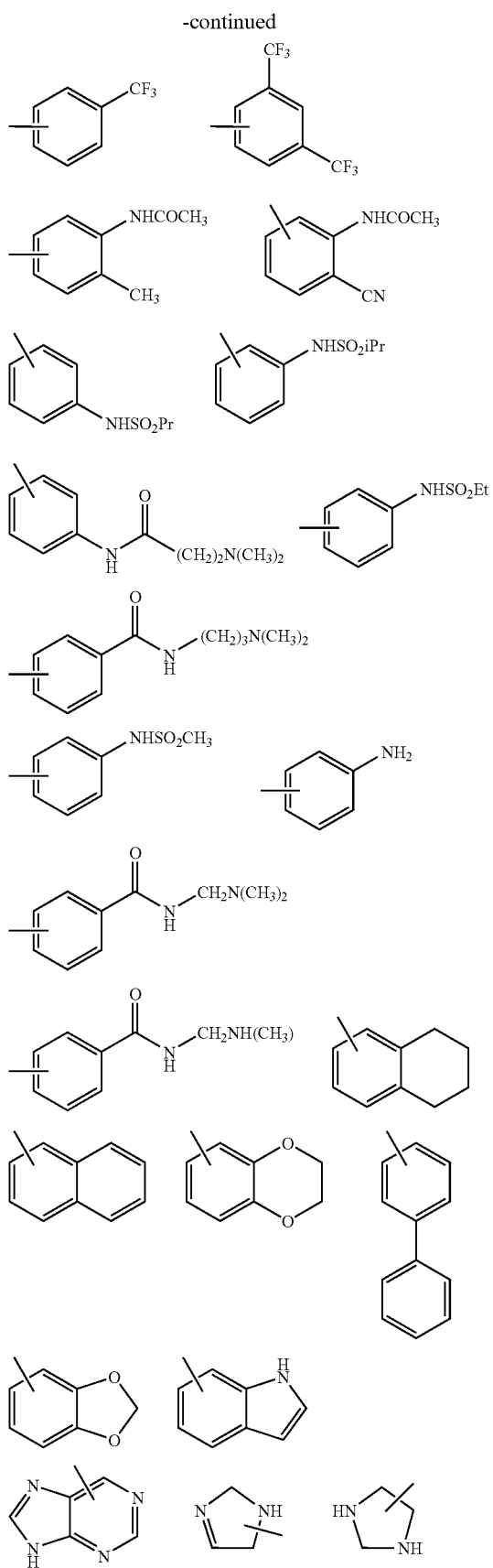

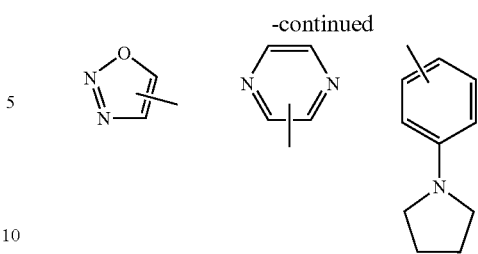

where the line drawn through the side of the substituent indicates that the substituent can be joined to the linker at any ring atom where there is a hydrogen available for replacement.

In some embodiments of the compounds of formula I, Ia, Ib, II, IIa, or IIb, $R^x$ is hydrogen.

In some embodiments of the compounds of formula I, Ia, Ib, II, IIa, or IIb, $R^y$ is 4-methylpiperazinyl.

In some embodiments of the compounds of formula I, Ia, Ib, II, IIa, or IIb, $R^y$ is N-(4-hydroxypiperidin)-yl or O-(4-piperidinyl).

In other embodiments of the compounds of formula I, Ia, Ib, II, IIa, or IIb, $R^1$ is phenyl.

In still other embodiments, the invention provides the compounds shown in Table 1, or a pharmaceutically acceptable salt, derivative or prodrug thereof.

TABLE 1

| Example No. | Structure |
|---|---|
| 4 | 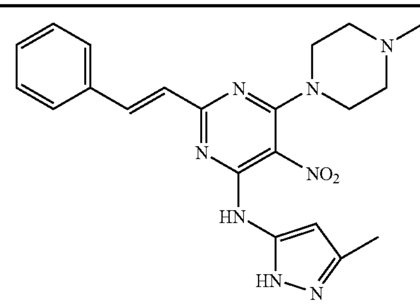 |
| 5 | 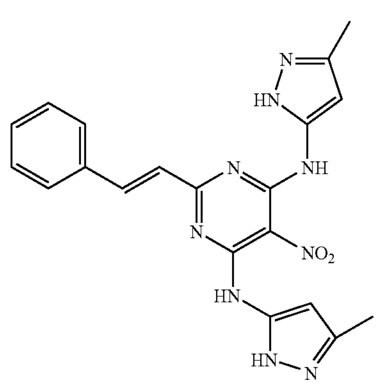 |

TABLE 1-continued

| Example No. | Structure |
|---|---|
| 6 | 2-styryl-4-morpholino-5-nitro-6-((5-methyl-1H-pyrazol-3-yl)amino)pyrimidine |
| 7 | 2-styryl-4-(piperazin-1-yl)-5-nitro-6-((5-methyl-1H-pyrazol-3-yl)amino)pyrimidine |
| 8 | 2-styryl-4-(piperidin-1-yl)-5-nitro-6-((5-methyl-1H-pyrazol-3-yl)amino)pyrimidine |
| 9 | 2-styryl-4-(pyrrolidin-1-yl)-5-nitro-6-((5-methyl-1H-pyrazol-3-yl)amino)pyrimidine |
| 10 | 2-styryl-4-(4-methylpiperazin-1-yl)-5-amino-6-((5-methyl-1H-pyrazol-3-yl)amino)pyrimidine |
| 11 | 2-styryl-4-((5-methyl-1H-pyrazol-3-yl)amino)-5-amino-6-((5-methyl-1H-pyrazol-3-yl)amino)pyrimidine |
| 12 | 2-styryl-4-morpholino-5-amino-6-((5-methyl-1H-pyrazol-3-yl)amino)pyrimidine |
| 13 | 2-styryl-4-(piperazin-1-yl)-5-amino-6-((5-methyl-1H-pyrazol-3-yl)amino)pyrimidine |
| 14 | 2-styryl-4-(piperidin-1-yl)-5-amino-6-((5-methyl-1H-pyrazol-3-yl)amino)pyrimidine |

TABLE 1-continued

| Example No. | Structure |
|---|---|
| 15 | (structure) |
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |

TABLE 1-continued

| Example No. | Structure |
|---|---|
| 26 | 4-((5-methyl-1H-pyrazol-3-yl)amino)-2-styryl-pyrimidine-6-carboxylic acid methyl ester |
| 29 | 6-chloro-N-(5-methyl-1H-pyrazol-3-yl)-2-(phenylethynyl)pyrimidin-4-amine |
| 30 | 6-(4-methylpiperazin-1-yl)-N-(5-methyl-1H-pyrazol-3-yl)-2-(phenylethynyl)pyrimidin-4-amine |
| 31 | 6-(4-methylpiperazin-1-yl)-N-(5-methyl-1H-pyrazol-3-yl)-2-styryl-pyrimidin-4-amine |
| 32 | 6-(4-methylpiperazin-1-yl)-N-(5-methyl-1H-pyrazol-3-yl)-2-((Z)-styryl)pyrimidin-4-amine |
| 34 | N-(5-methyl-1H-pyrazol-3-yl)-2-styryl-6-X-pyrimidin-4-amine, X = Cl, Br, I |
| 37 | methyl 4-((E)-2-(6-chloro-4-((5-methyl-1H-pyrazol-3-yl)amino)-5-nitropyrimidin-2-yl)vinyl)benzoate |
| 38 | methyl 4-((E)-2-(6-(4-methylpiperazin-1-yl)-4-((5-methyl-1H-pyrazol-3-yl)amino)-5-nitropyrimidin-2-yl)vinyl)benzoate |

TABLE 1-continued
| Example No. | Structure |
|---|---|
| 39 | 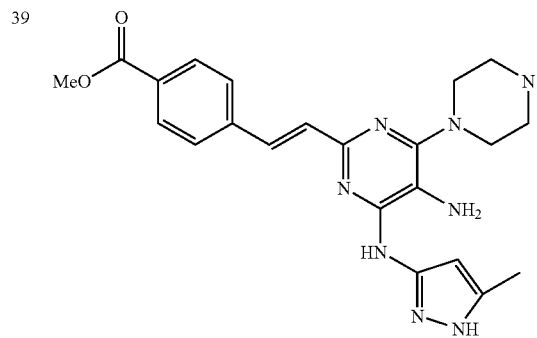 |
| 40 | 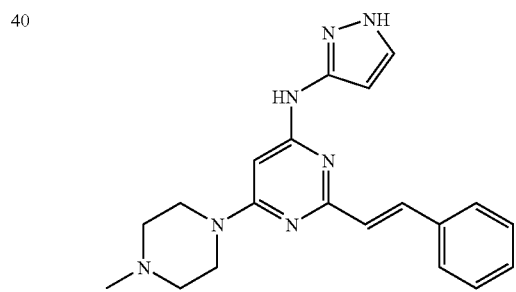 |
| 41 | 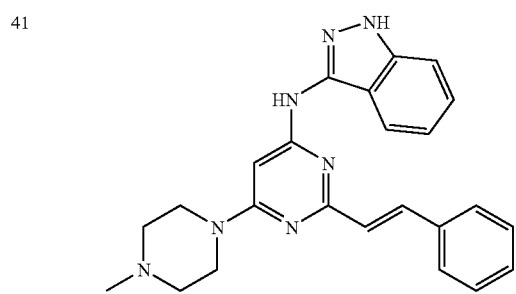 |
| 42 | 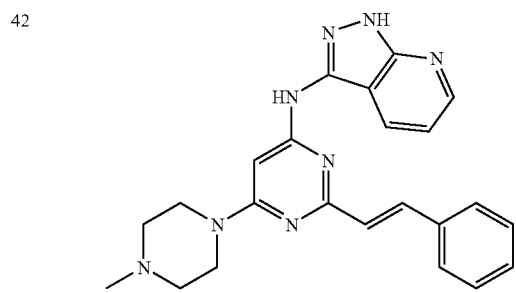 |
TABLE 1-continued
| Example No. | Structure |
|---|---|
| 43 | 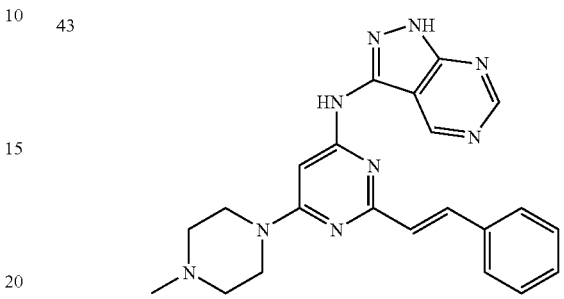 |
| 44 | 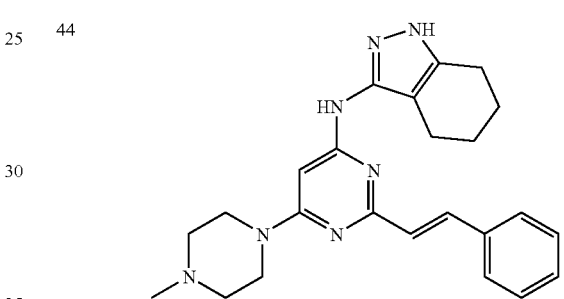 |
| 45 | 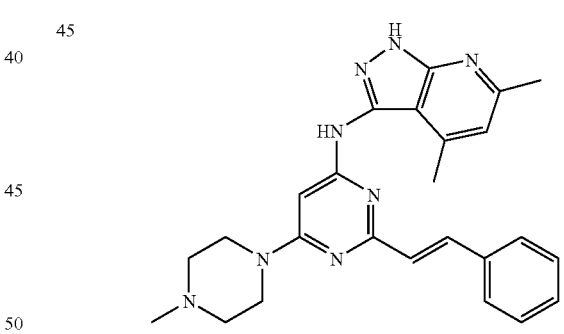 |
| 46 | 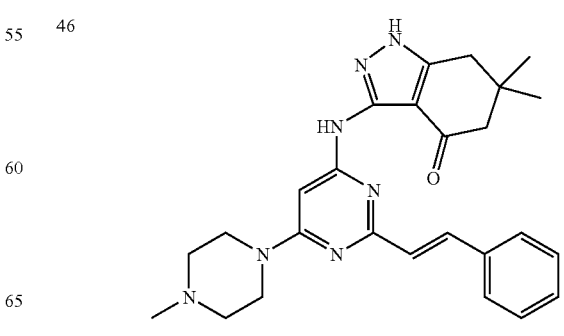 |

TABLE 1-continued

| Example No. | Structure |
|---|---|
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |

TABLE 1-continued

| Example No. | Structure |
|---|---|
| 56 | (structure) |
| 57 | (structure) |
| 58 | (structure) |
| 59 | (structure) |
| 60 | (structure) |
| 61 | (structure) |
| 62 | (structure) |
| 63 | (structure) |
| 64 | (structure) |

TABLE 1-continued
| Example No. | Structure |
|---|---|
| 65 | 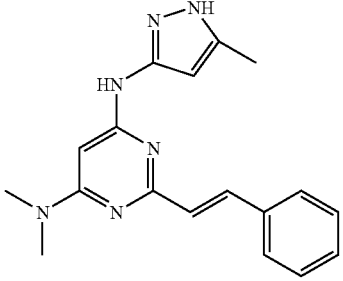 |
| 66 | 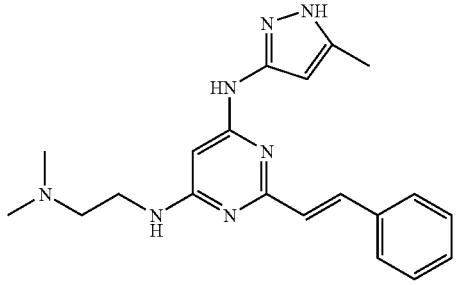 |
| 67 | 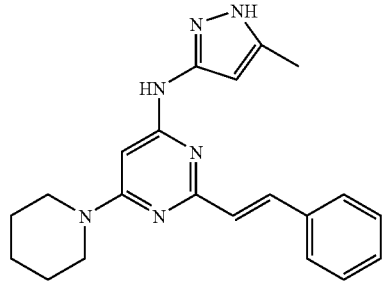 |
| 68 | 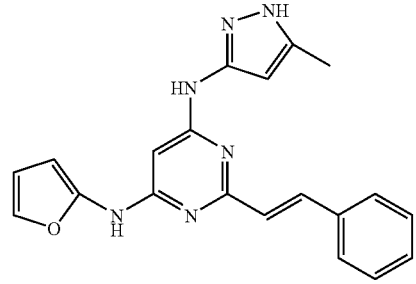 |
| 69 | 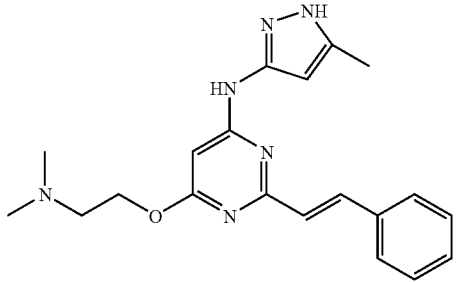 |
| 70 | 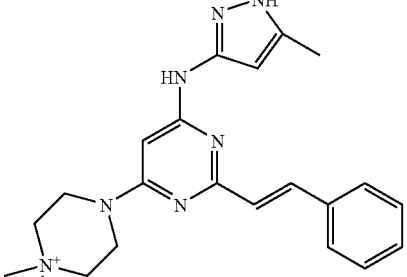 |
| 71 |  |
| 72 | 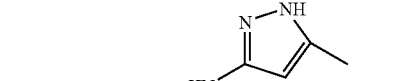 |
| 73 | 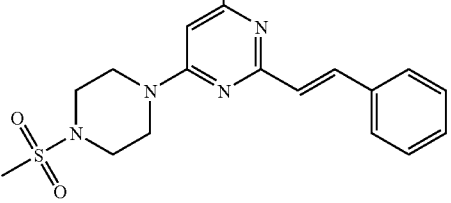 |

TABLE 1-continued

| Example No. | Structure |
|---|---|
| 74 | 4-pyridylamino, 5-methyl-1H-pyrazol-3-ylamino pyrimidine with styryl |
| 75 | 1-methylpiperidin-4-ylamino, 5-methyl-1H-pyrazol-3-ylamino pyrimidine with styryl |
| 76 | pyrrolidin-1-yl, 5-methyl-1H-pyrazol-3-ylamino pyrimidine with styryl |
| 77 | 2-(4-methylpiperazin-1-yl)ethylamino, 5-methyl-1H-pyrazol-3-ylamino pyrimidine with styryl |
| 78 | tetrahydrofuran-2-ylamino, 5-methyl-1H-pyrazol-3-ylamino pyrimidine with styryl |
| 79 | 2-morpholinoethylamino, 5-methyl-1H-pyrazol-3-ylamino pyrimidine with styryl |
| 80 | 2-(pyridin-4-yl)ethylamino, 5-methyl-1H-pyrazol-3-ylamino pyrimidine with styryl |
| 81 | tetrahydropyran-4-yloxy, 5-methyl-1H-pyrazol-3-ylamino pyrimidine with styryl |
| 82 | phenylamino, 5-methyl-1H-pyrazol-3-ylamino pyrimidine with styryl |
| 83 | thiomorpholin-4-yl, 5-methyl-1H-pyrazol-3-ylamino pyrimidine with styryl |

TABLE 1-continued

| Example No. | Structure |
|---|---|
| 84 | (structure) |
| 85 | (structure) |
| 86 | (structure) |
| 87 | (structure) |
| 88 | (structure) |
| 89 | (structure) |
| 90 | (structure) |
| 91 | (structure) |
| 92 | (structure) |

TABLE 1-continued

| Example No. | Structure |
|---|---|
| 93 | (morpholin-3-yl pyrimidine with pyrazolylamino and styryl substituents) |
| 94 | (6-ethyl pyrimidine with pyrazolylamino and styryl substituents) |
| 95 | (6-ethoxy pyrimidine with pyrazolylamino and styryl substituents) |
| 96 | (6-phenyl pyrimidine with pyrazolylamino and styryl substituents) |
| 97 | (6-methoxymethoxy pyrimidine with pyrazolylamino and styryl substituents) |
| 98 | (4-methylpiperazinyl pyrimidine with pyrazolylamino and 4-fluorostyryl substituents) |
| 99 | (tetrahydropyran-4-ylamino pyrimidine with pyrazolylamino and styryl substituents) |
| 100 | (piperidin-4-yloxy pyrimidine with pyrazolylamino and styryl substituents) |
| 101 | (4-hydroxypiperidin-1-yl pyrimidine with pyrazolylamino and styryl substituents) |
| 102 | (2-methoxyethylamino pyrimidine with pyrazolylamino and styryl substituents) |

TABLE 1-continued

| Example No. | Structure |
|---|---|
| 103 | (structure) |
| 104 | (structure) |
| 105 | (structure) |
| 106 | (structure) |
| 107 | (structure) |
| 108 | (structure) |
| 109 | (structure) |
| 110 | (structure) |
| 111 | (structure) |

TABLE 1-continued

| Example No. | Structure |
|---|---|
| 112 | 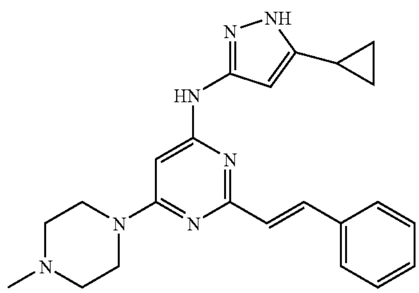 |
| 113 | 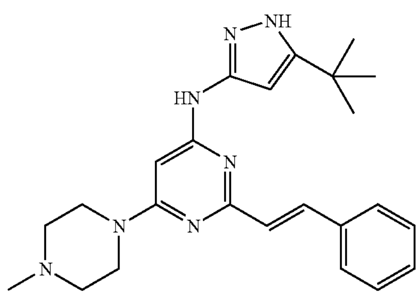 |
| 114 | 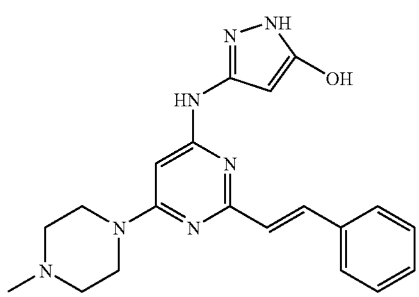 |
| 115 | 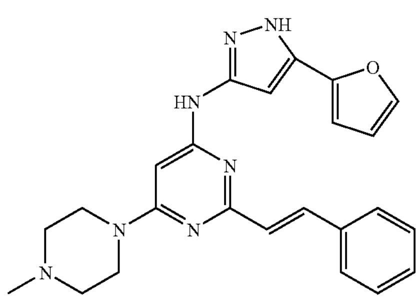 |
| 116 | 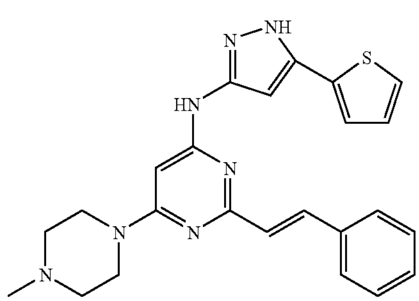 |
| 117 | |
| 118 | |
| 119 | |
| 120 | |
| 121 | |

TABLE 1-continued

| Example No. | Structure |
|---|---|
| 122 | (4-methylpiperazin-1-yl)ethylamino / pyrazolylamino pyrimidine / 4-methylstyryl |
| 123 | morpholinyl-acetamido / pyrazolylamino pyrimidine / 4-methylstyryl |
| 124 | morpholinyl-ethyl carboxamide / pyrazolylamino pyrimidine / 4-methylstyryl |
| 125 | piperidin-4-yloxy / pyrazolylamino pyrimidine / 4-fluorostyryl |
| 126 | 4-hydroxypiperidin-1-yl / pyrazolylamino pyrimidine / 4-fluorostyryl |
| 127 | 2-methoxyethylamino / pyrazolylamino pyrimidine / 4-fluorostyryl |
| 128 | tetrahydropyran-4-ylamino / pyrazolylamino pyrimidine / 4-fluorostyryl |
| 129 | dimethylaminoethylamino / pyrazolylamino pyrimidine / 4-fluorostyryl |
| 130 | (4-methylpiperazin-1-yl)ethylamino / pyrazolylamino pyrimidine / 4-fluorostyryl |
| 131 | morpholinyl-propanamido / pyrazolylamino pyrimidine / 4-fluorostyryl |

TABLE 1-continued
| Example No. | Structure |
|---|---|
| 132 | 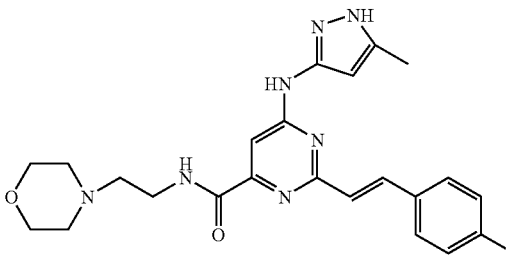 |
| 133 | 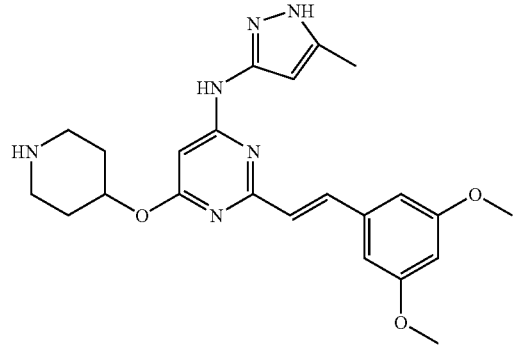 |
| 134 | 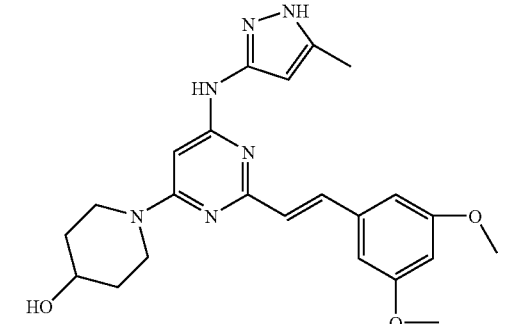 |
| 135 | 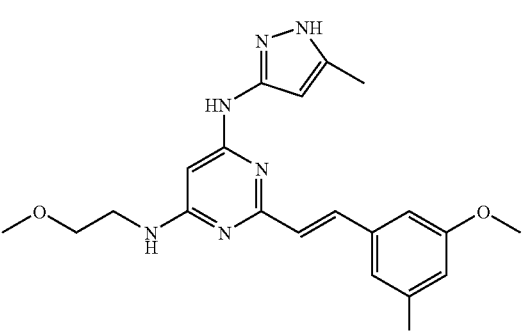 |
| 136 | 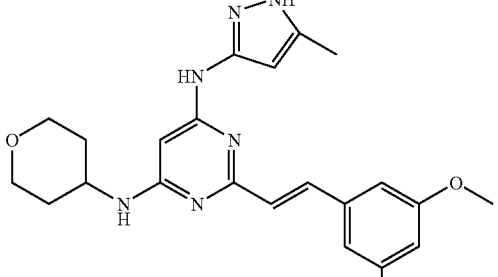 |
| 137 | 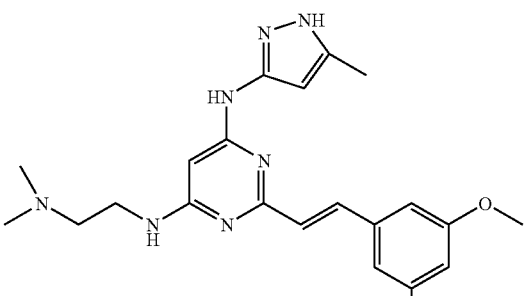 |
| 138 | 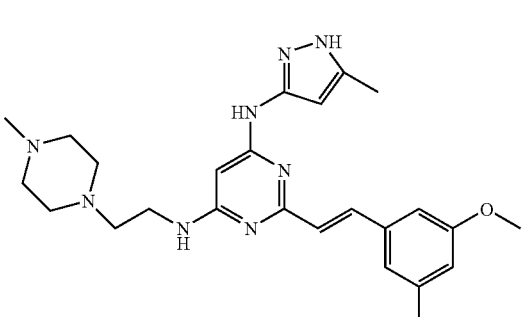 |
| 139 | 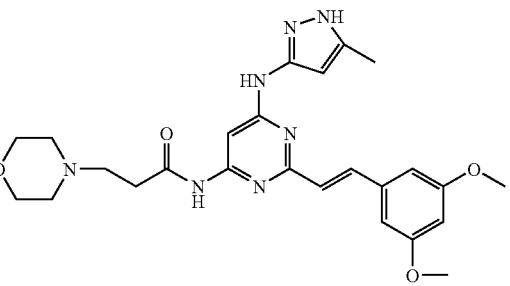 |

TABLE 1-continued
| Example No. | Structure |
|---|---|
| 140 | 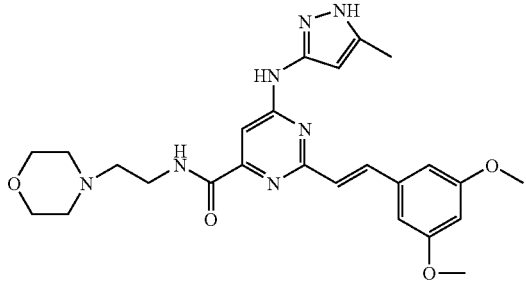 |
| 141 | 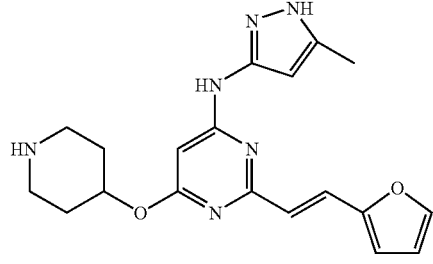 |
| 142 | 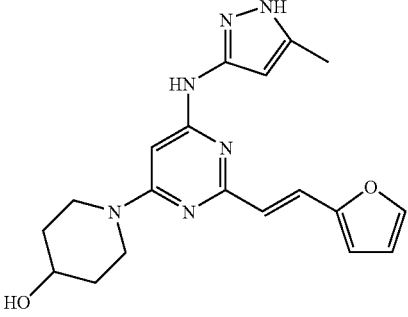 |
| 143 | 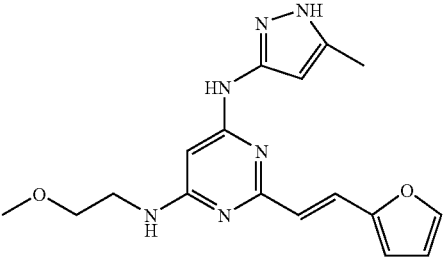 |
| 144 | 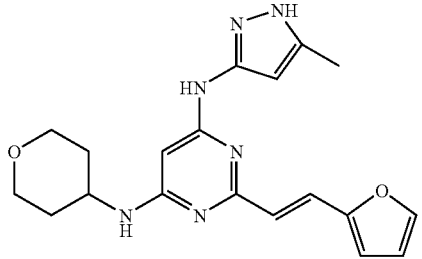 |
| 145 | 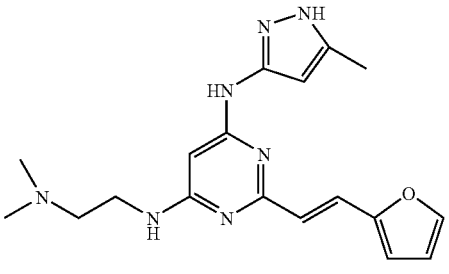 |
| 146 | 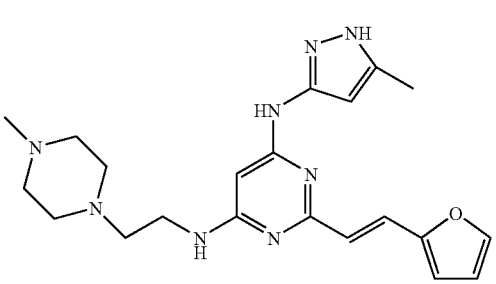 |
| 147 | 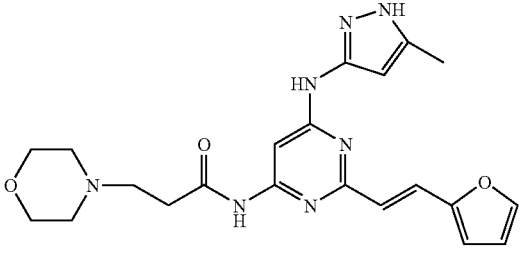 |
| 148 | 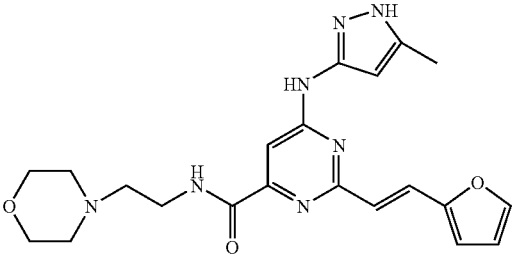 |
| 149 | 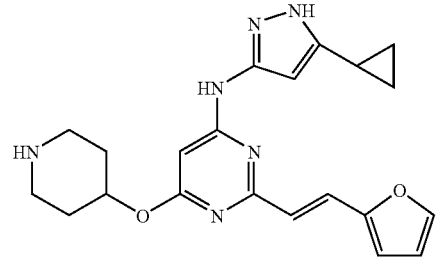 |

TABLE 1-continued

| Example No. | Structure |
|---|---|
| 150 | (structure) |
| 151 | (structure) |
| 152 | (structure) |
| 153 | (structure) |
| 154 | (structure) |
| 155 | (structure) |
| 156 | (structure) |
| 157 | (structure) |
| 158 | (structure) |
| 159 | (structure) |

TABLE 1-continued

| Example No. | Structure |
|---|---|
| 160 | 4-[(5-methyl-1H-pyrazol-3-yl)amino]-6-(4-methylpiperazin-1-yl)-2-[(E)-2-(4-methoxyphenyl)ethenyl]pyrimidine |
| 161 | 4-[(5-methyl-1H-pyrazol-3-yl)amino]-6-(4-methylpiperazin-1-yl)-2-[(E)-2-(3,4,5-trifluorophenyl)ethenyl]pyrimidine |
| 162 | 4-[(5-methyl-1H-pyrazol-3-yl)amino]-6-[(furan-2-ylmethyl)amino]-2-[(E)-2-phenylethenyl]pyrimidine |
| 163 | 4-[(5-methyl-1H-pyrazol-3-yl)amino]-6-[(2-methoxyethyl)amino]-2-[(E)-2-phenylethenyl]pyrimidine |
| 164 | 4-[(5-methyl-1H-pyrazol-3-yl)amino]-6-[(tetrahydrofuran-2-ylmethyl)amino]-2-[(E)-2-phenylethenyl]pyrimidine |
| 165 | 4-[(5-methyl-1H-pyrazol-3-yl)amino]-6-[(1-methylpiperidin-4-yl)oxy]-2-[(E)-2-phenylethenyl]pyrimidine |
| 166 | 4,6-dihydroxy-2-[(E)-2-phenylethenyl]pyrimidine |
| 167 | 4,6-dihalo-2-[(E)-2-phenylethenyl]pyrimidine; X = Cl, Br, I |
| 168 | 4-halo-6-(4-methylpiperazin-1-yl)-2-[(E)-2-phenylethenyl]pyrimidine; X = Cl, Br, I |
| 169 | 4-[(5-methyl-1H-pyrazol-3-yl)amino]-5-nitro-6-(4-methylpiperazin-1-yl)-2-[(E)-2-(4-methylphenyl)ethenyl]pyrimidine |

*Note: Structure names above are interpretive approximations of the drawn structures in the original table.*

TABLE 1-continued

| Example No. | Structure |
|---|---|
| 170 | (structure) |
| 171 | (structure) |
| 172 | (structure) |
| 173 | (structure) |
| 174 | (structure) |
| 175 | (structure) |
| 176 | (structure) |
| 177 | (structure) |
| 178 | (structure) |

TABLE 1-continued

| Example No. | Structure |
|---|---|
| 179 | 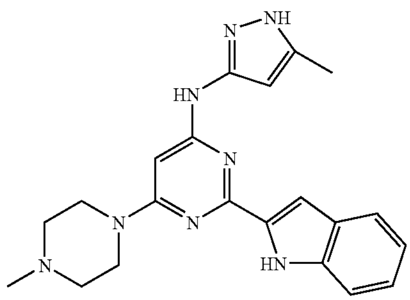 |

In one embodiment, this invention provides a composition comprising a compound of formula I, and a pharmaceutically acceptable carrier. In some such embodiments, the composition is for treating or preventing a kinase mediated disorder.

In another embodiment, this invention relates to a method of treating or preventing a kinase mediated disease, which method comprises administering to a patient in need of such a treatment a therapeutically effective amount of a compound of formula I, or a pharmaceutical composition thereof.

In some aspects of the aforementioned methods and compositions, the disorder is mediated by Aurora A, Aurora B, CDK-2, ERK-2, AKT, Src, Lck, Abl, cKit, Flt3, or KDR. In other aspects, the disorder is mediated by Aurora A, Src, Lck, Abl, cKit, Flt3, or KDR.

Another aspect of this invention relates to a method of inhibiting Aurora A activity in a patient, which method comprises administering to the patient a compound of formula I or a composition comprising said compound.

Another aspect of this invention relates to a method of treating or preventing a GSK-3-mediated disease with a GSK-3 inhibitor, which method comprises administering to a patient in need of such a treatment a therapeutically effective amount of a compound of formula I or a pharmaceutical composition thereof.

One aspect of this invention relates to a method of enhancing glycogen synthesis and/or lowering blood levels of glucose in a patient in need thereof, which method comprises administering to the patient a therapeutically effective amount of a compound of formula I, or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of beta-catenin, which is useful for treating schizophrenia.

Another aspect of this invention relates to a method of inhibiting GSK-3 activity in a patient, which method comprises administering to the patient a compound of formula I, or a composition comprising said compound.

Another aspect of this invention relates to a method of treating or preventing a Src-mediated disease with a Src inhibitor, which method comprises administering to a patient in need of such a treatment a therapeutically effective amount of a compound of formula I or a pharmaceutical composition thereof.

Another aspect of the invention relates to inhibiting Src activity in a patient, which method comprises administering to the patient a compound of formula I, or a composition comprising said compound.

Another method relates to inhibiting Aurora A, GSK-3, or Src activity in a biological sample, which method comprises contacting the biological sample with the Aurora A, GSK-3, or Src inhibitor of formula I, or a pharmaceutical composition thereof, in an amount effective to inhibit Aurora-2, GSK-3, or Src.

Each of the aforementioned methods directed to the inhibition of Aurora A, GSK-3, or Src, or the treatment of a disease alleviated thereby, is preferably carried out with a preferred compound of formula I, as described above.

The present invention also relates to the processes for preparing the compounds of the invention and to the synthetic intermediates useful in such process, as described below and in the Examples.

Scheme 1

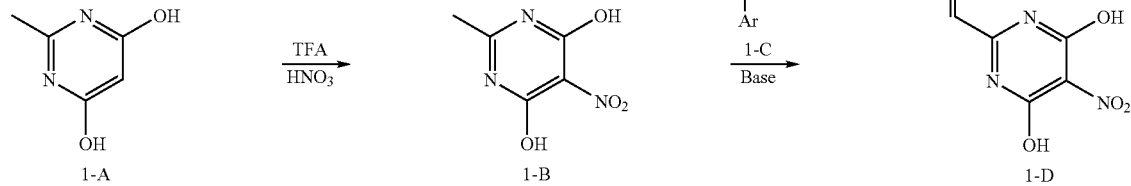

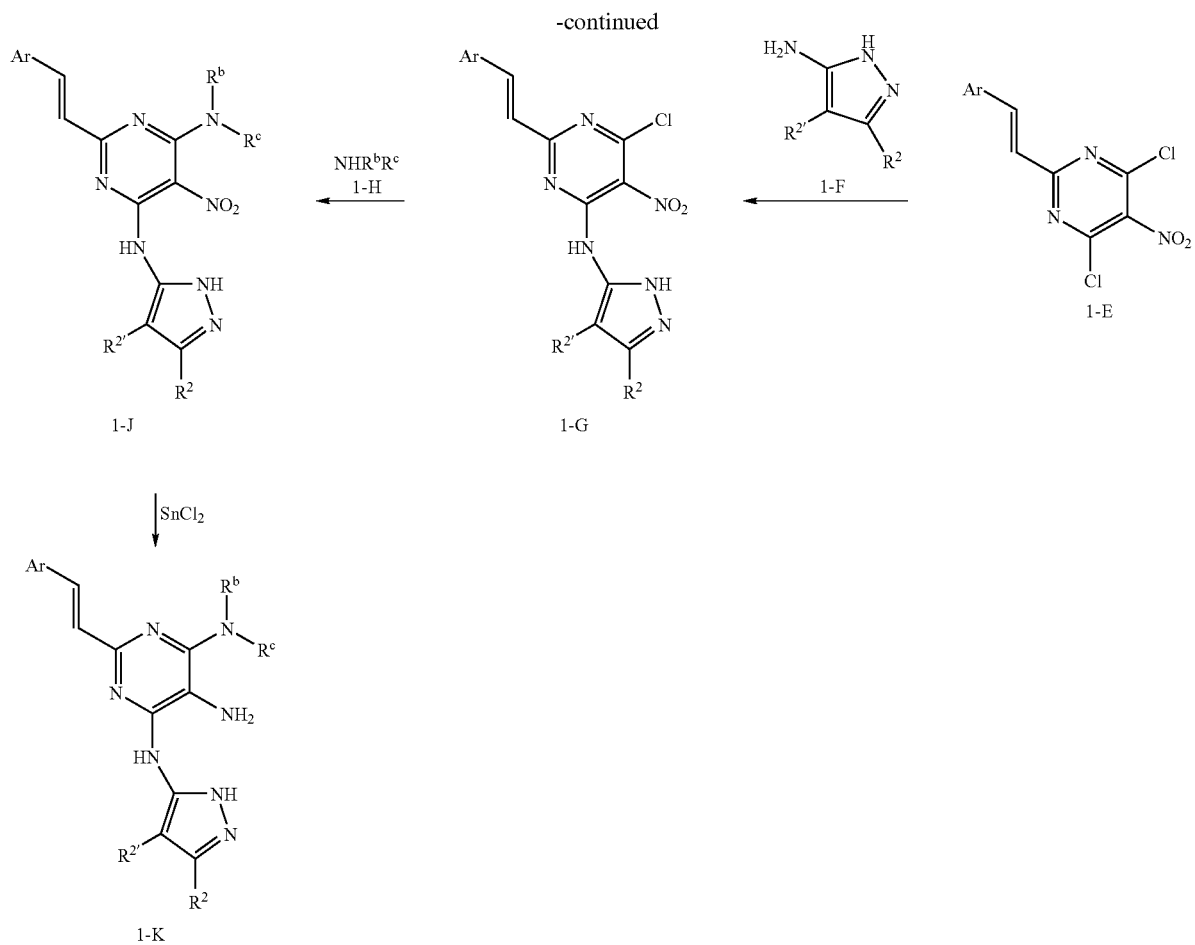

In another aspect of this invention, preferred embodiments of Formula 1-K can be synthesized as shown in Scheme 1 wherein the variable substituents are as described above and examples of which are indicated by Table 1 and —Ar is an optionally substituted aryl or heteroaryl group as defined and examples of which are indicated by Table 1. Dihydroxypyrimidine 1-A is dissolved in about one to 20 volumes of trifluoroacetic acid and treated with about one to five equivalents of nitric acid at about −20 to 30° C. for about 30 minutes to 24 hours. The resulting nitropyrimidine 1-B is treated with about one to 20 equivalents of an optionally substituted aromatic or heteroaromatic aldehyde 1-C and about one to 20 equivalents of an organic base, preferably piperidine, at about 20 to 120° C. for about 30 minutes to 24 hours to provide a vinylpyrimidine 1-D. A vinylpyrimidine 1-D is treated with about two to 20 equivalents of phosphorous oxychloride and about two to five equivalents of a tertiary organic base, preferably diethylaniline, at about 0 to 200° C. for about 30 minutes to 24 hours to give a dichoropyrimidine 1-E. A dichloropyrimidine 1-E in a suitable solvent such as, but not limited to, tetrahydrofuran is treated with about one to 10 equivalents of a tertiary organic base such as, but not limited to, triethylamine and about one equivalent of an aminopyrazole 1-F at about 0 to 65° C. for about 30 minutes to 24 hours to give a aminopyrimidine 1-G. Subsequently, 1-G, in a suitable solvent such as, but not limited to, tetrahydrofuran is treated with about one to 10 equivalents of a tertiary organic base such as, but not limited to, triethylamine and about one to five equivalents of a primary or secondary amine 1-H at about 0 to 65° C. for about 30 minutes to 24 hours to give a diaminopyrimidine 1-J. A diaminopyrimidines 1-J is dissolved in a suitable solvent such as, but not limited to, methanol and added to about two to 10 equivalents of a suitable chemical reducing agent such as, but not limited to, tin (II) chloride or titanium (III) chloride in dilute hydrochloric acid at about 0 to 65° C. for about 30 minutes to 24 hours to give a triaminopyrimidine 1-K.

In another aspect of this invention, preferred embodiments of Formula 2-F are prepared as shown in Scheme 2 wherein the variable substituents are as described above and examples of which indicated by Table 1. A solution of about one to five equivalents of an aminopyrazole 2-B in a suitable solvent such as, but not limited to, dioxane, is added to a solution of dichloropyrimidine 2-A and about one to 10 equivalents of a suitable organic base, preferably 2,6-lutidine, in a suitable solvent such as, but not limited to, dioxane at from about 0 to 60° C. for about 15 minutes to 24 hours to give a chloropyrimidine 2-C. A mixture of a chloropyrimidine 2-C, about one to five equivalents of an inorganic base such as, but not limited to, sodium, potassium or cesium carbonate, about one to five equivalents of an optionally substituted cis- or trans-aryl- or heteroaryl-vinylboronic acid 2-D, about 0.01 to 1 equivalents of a palladium catalyst such as, but not limited to, tetrakis(triphenylphosphine)-palladium in a suitable solvent such as, but not limited to, toluene or tetrahydrofuran at about 20 to 150° C. for about 30 minutes to 24 hours provides a vinylpyrimidine 2-E. A solution of a vinylpyrimidine 2-E in a suitable solvent such as, but not limited to, dimethylsulfoxide, acetic acid or acetonitrile is treated with about two to 20 equivalents of a chemical reducing agent such as, but not limited to, zinc dust and ammonium formate, tin (II) chloride or titanium(III) chloride to give an aminopyrimidine 2-F. The aminopyrimidine 2-F will be either cis or trans depending upon whether the cis or trans isomer, respectively, of the aryl- or heteroaryl-vinylboronic acid is used in the reaction sequence.

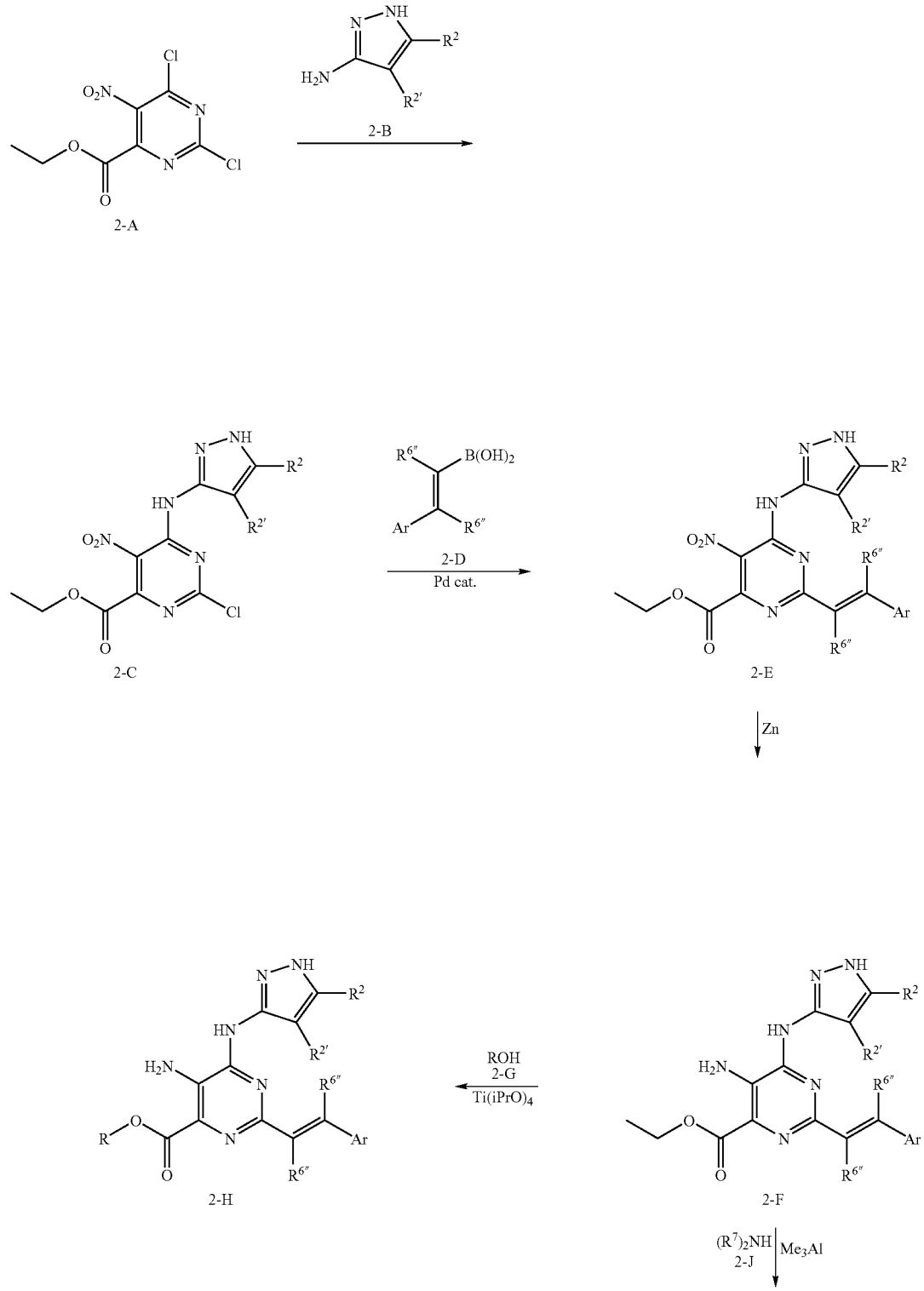

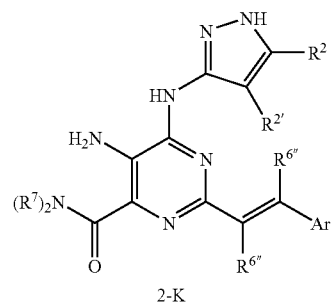

2-K

In another aspect of this invention, preferred embodiments 2-H are prepared as shown in Scheme 2 whereby an aminopyrimidine 2-F is treated with about one to 100 equivalents of an alcohol 2-G alone or in a suitable solvent and about 0.1 to 5 equivalents of titanium(IV) isopropoxide or potassium cyanide at about 0 to 150° C. for about one to 48 hours.

In another aspect of this invention, preferred embodiments 2-K are prepared as shown in Scheme 2 whereby an aminopyrimidine 2-F is treated with about one to 20 equivalents of an amine 2-J in a suitable solvent such as, but not limited to, dichloromethane, and about one to 20 equivalents of trimethylaluminum at 0 to 30° C. for about one to 48 hours.

-continued

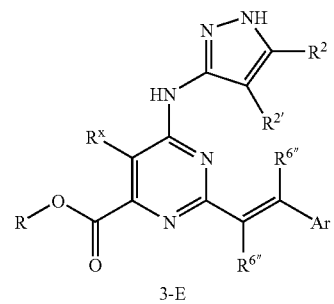

3-E

In another aspect of this invention, preferred embodiments of Formula 3-E are prepared as shown in Scheme 3 wherein the variable substituents are as described above. A solution of about one to five equivalents of an aminopyrazole 3-B in a suitable solvent such as, but not limited to, dioxane, is added to a solution of dichloropyrimidine 3-A and about one to 10 equivalents of a suitable organic base, preferably 2,6-lutidine, in a suitable solvent such as, but not limited to, dioxane, at from about 0 to 60° C. for about 15 minutes to 24 hours to give a chloropyrimidine 3-C. A mixture of a chloropyrimidine 3-C, about one to five equivalents of an inorganic base such as, but not limited to, sodium, potassium or cesium carbonate, about one to five equivalents of an optionally substituted cis- or trans- aryl- or heteroaryl-vinylboronic acid 3-D, about 0.01 to 1 equivalents of a palladium catalyst such as, but not limited to, tetrakis-(triphenyl-phosphine)-palladium in a suitable solvent such as, but not limited to, toluene or tetrahydrofuran, at about 20 to 150° C. for about 30 minutes to 24 hours provides a vinylpyrimidine 3-E. The vinylpyrimidine 3-E will be either cis or trans depending upon whether the cis or trans isomer, respectively, of the aryl- or heteroaryl-vinylboronic acid is used in the reaction.

Scheme 3

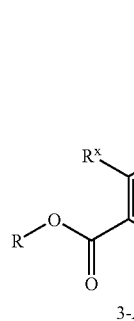 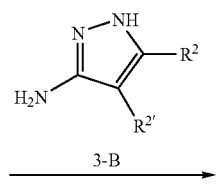

3-A

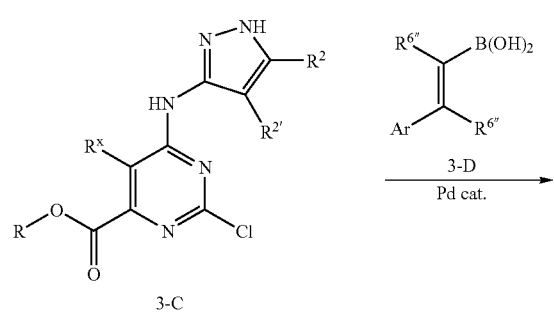 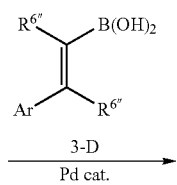

3-C

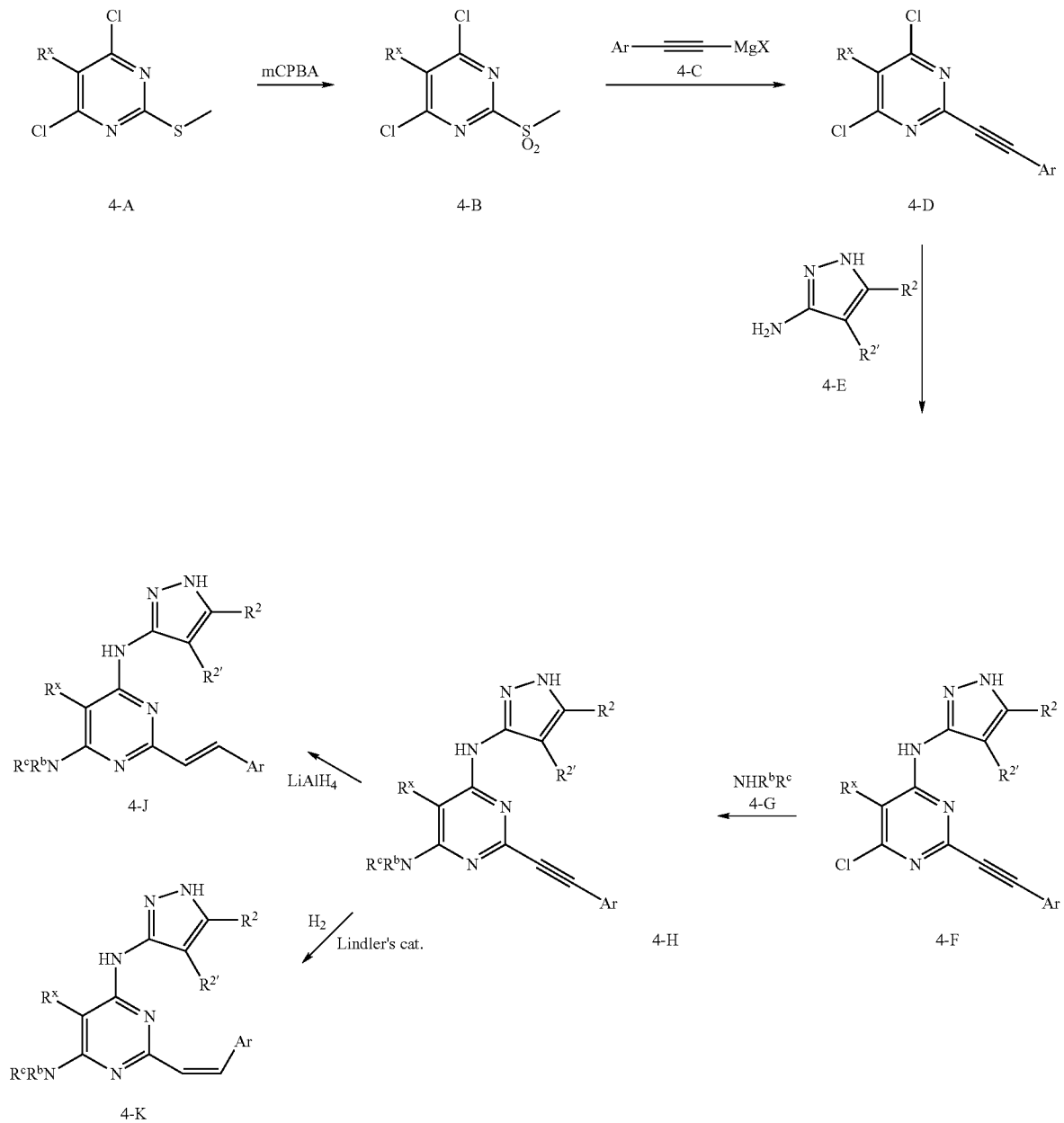

Scheme 4

In another aspect of this invention, preferred embodiments 4-H are prepared as shown in Scheme 4 wherein the variable substituents are as described above and examples are indicated by Table 1. A thiomethylpyrimidine 4-A in a suitable solvent such as, but not limited to, dichloromethane is treated with about two to 10 equivalents of an oxidizing agent such as, but not limited to, 3-chlorobenzoylperoxide (mCPBA). at about 0 to 30° C. for about 30 minutes to 24 hours to give a sulfonylpyrimidine 4-B. A sulfonylpyrimidine 4-B in a suitable solvent such as, but not limited to, tetrahydrofuran is treated with about one to five equivalents of an optionally substituted aryl or heteroaryl-acetylenyl magnesium halide 4-C at about −50 to 30° C. for about one to 24 hours to give a propargylpyrimidine 4-D. A propargylpyrimidine 4-D in a suitable solvent such as, but not limited to, dimethylacetamide is treated with about one to two equivalents of an aminopyrazole 4-E, one to five equivalents of sodium iodide, and about one to five equivalents of a tertiary organic base such as, but not limited to, di-isopropylethylamine at about 0 to 140° C. for about one to 24 hours to give a monochloropyrimidine 4-F. A monochloropyrimidine 4-F in a suitable solvent such as, but not limited to, dioxane is treated with one to five equivalents of a primary or secondary amine 4-G, about 0.01 to one equivalents of 4-dimethylaminopyridine, and about one to five equivalents of a tertiary organic base such as, but not limited to, di-isopropylethylamine, at about 20 to 110° C. for about one to 24 hours to give an aminopyrimidine 4-H.

In another aspect of this invention, preferred embodiments 4-J are prepared as shown in Scheme 4 wherein an aminopyrimidine 4-H in a suitable solvent such as, but not limited to, tetrahydrofuran, is treated with about 0.8 to 1.1 equivalents of lithium aluminum hydride at about −10 to 30° C. for about one to 24 hours to give a trans-styrylpyrimidine 4-J.

In another aspect of this invention, preferred embodiments 4-K are prepared as shown in Scheme 4 wherein an aminopyrimidine 4-H in a suitable solvent such as, but not limited to, ethyl acetate or methanol is treated with about 0.1 to 1 weight equivalents of Lindlar's catalyst, about 0.1 to 2 weight equivalents of quinoline and hydrogen gas at about one atmosphere to give a cis-styrylpyrimidine 4-K.

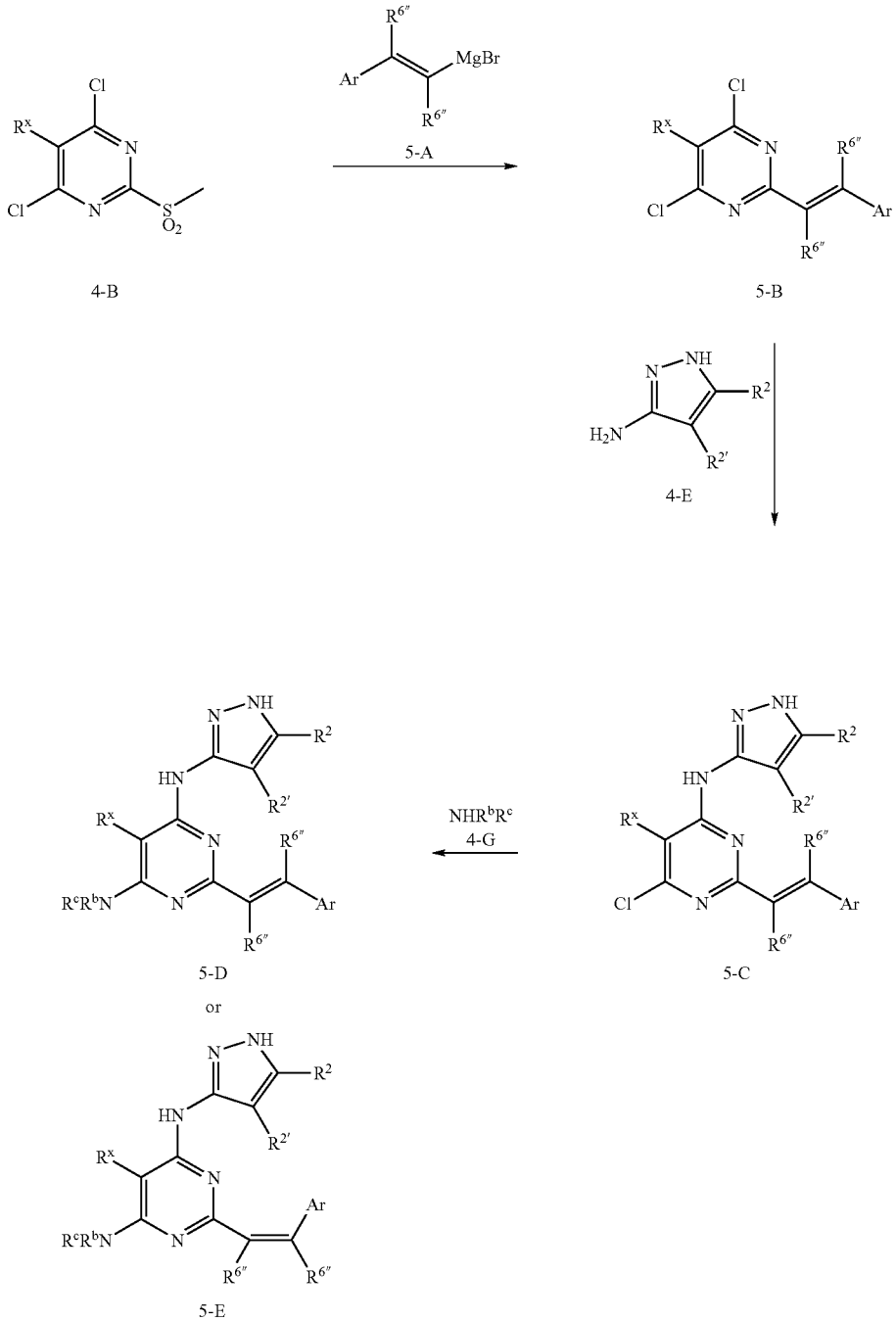

In another aspect of this invention, preferred embodiments 5-D and 5-E are prepared as shown in Scheme 5 wherein the variable substituents are as described above and examples of which are indicated by Table 1. A sulfonylpyrimidine 4-B in a suitable solvent such as, but not limited to, tetrahydrofuran is treated with about one to two equivalents of an optionally substituted cis- or trans-2-aryl- or heteroaryl-vinyl magnesium halide 5-A at about −50 to 30° C. for about 30 minutes to 24 hours to give a dichoropyrimidine 5-B. A dichloropyrimidine 5-B in a suitable solvent such as, but not limited to, dimethylacetamide is treated with about one to two equivalents of an aminopyrazole 4-E, about one to five equivalents of sodium iodide and about one to five equivalents of a tertiary organic base such as, but not limited to, di-isopropylethylamine at about 20 to 140° C. for about one to 24 hours to give a monochloropyrimidine 5-C. A monochloropyrimidine 5-C in a suitable solvent such as, but not limited to, dioxane is treated with about one to five equivalents of a primary or secondary amine 4-G, 0.05 to 1 equivalents of 4-dimethylaminopyridine, and about one to five equivalents of a tertiary organic base such as, but not limited to, di-isopropylethylamine at about 20 to 110° C. for about one to 72 hours to give either styrylpyrimidine 5-D or 5-E depending upon whether the vinyl magnesium halide 5-A used in the reaction sequence is the trans- or cis-isomer, respectively.

Scheme 6

In another aspect of this invention, preferred embodiments 6-G are prepared as shown in Scheme 6 wherein the variable substituents are as described above and examples of which are indicated in the accompanying figures. Selected examples of 6-G are indicated by Table 1.

R—X—H in Scheme 6 can for example be selected from the following structures:

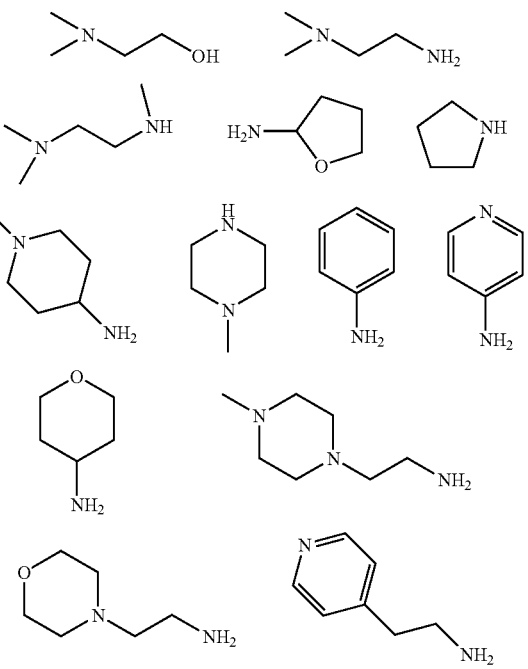

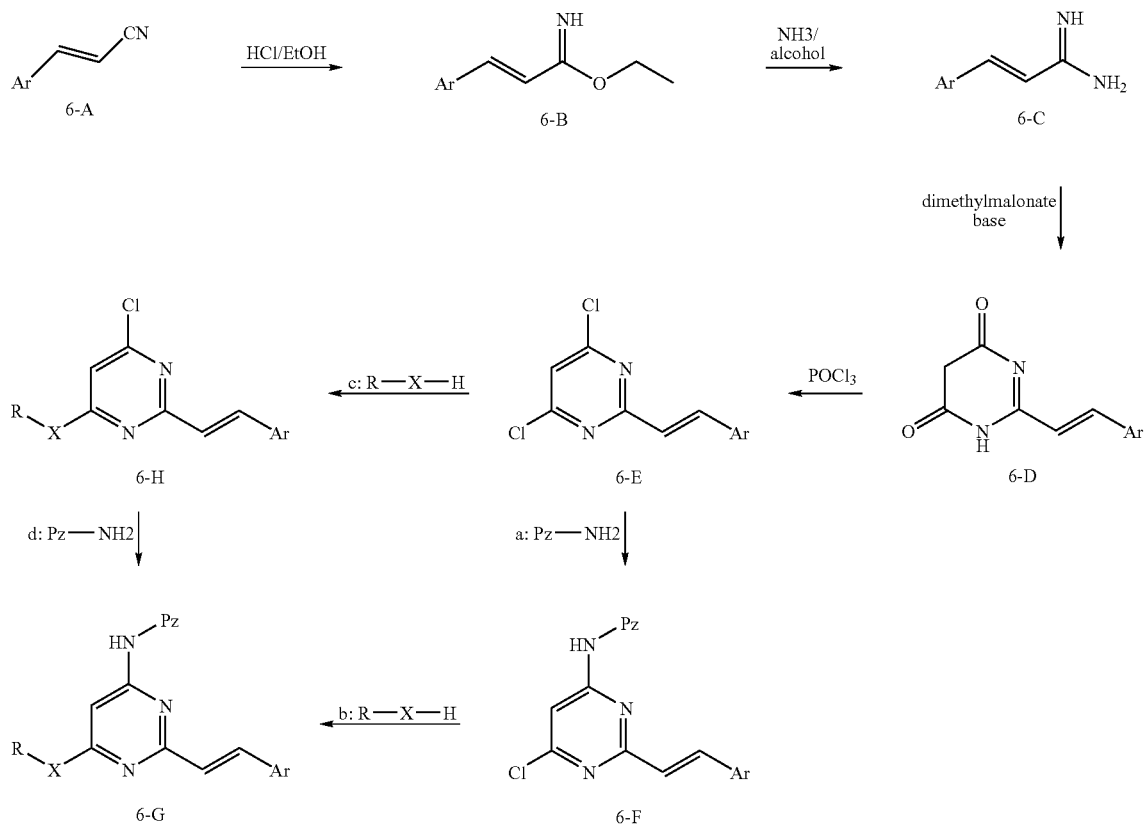

-continued
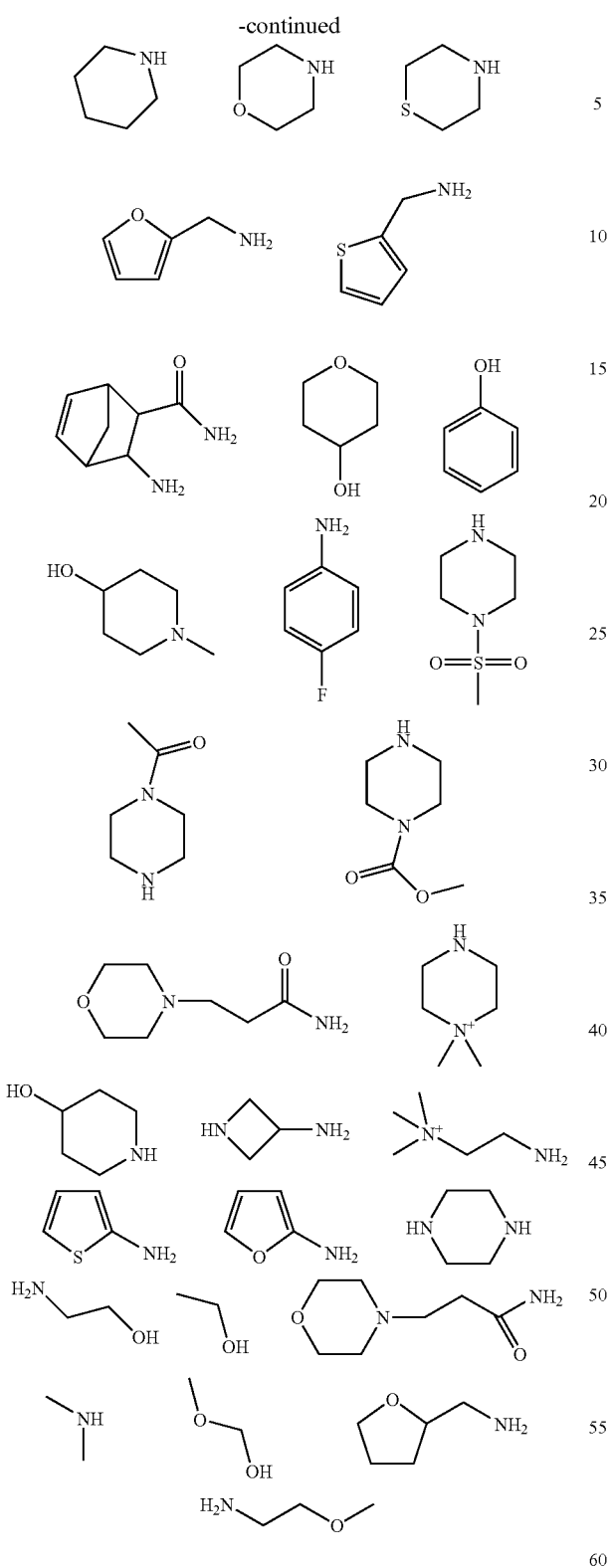
The moiety denoted "Ar" in Scheme 6 can for example be selected from the following structures, where the line drawn through the side of the substituent indicates that the "Ar" substituent can be joined to the linker alkene or linker alkyne at any ring atom where there is a hydrogen available for replacement:
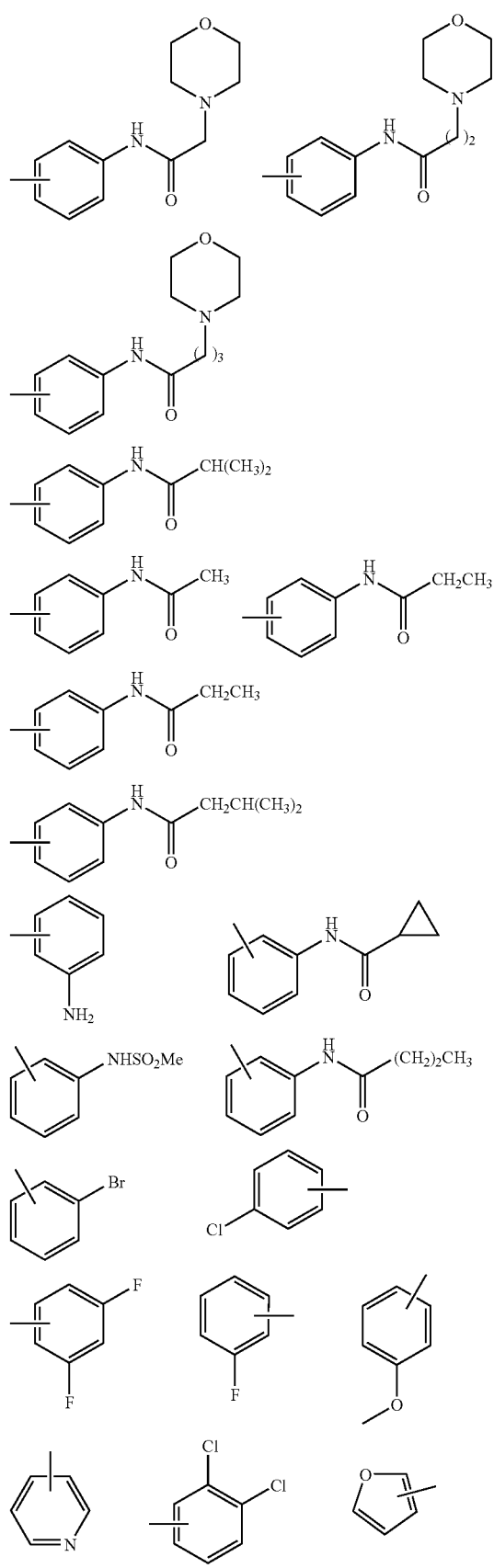

-continued
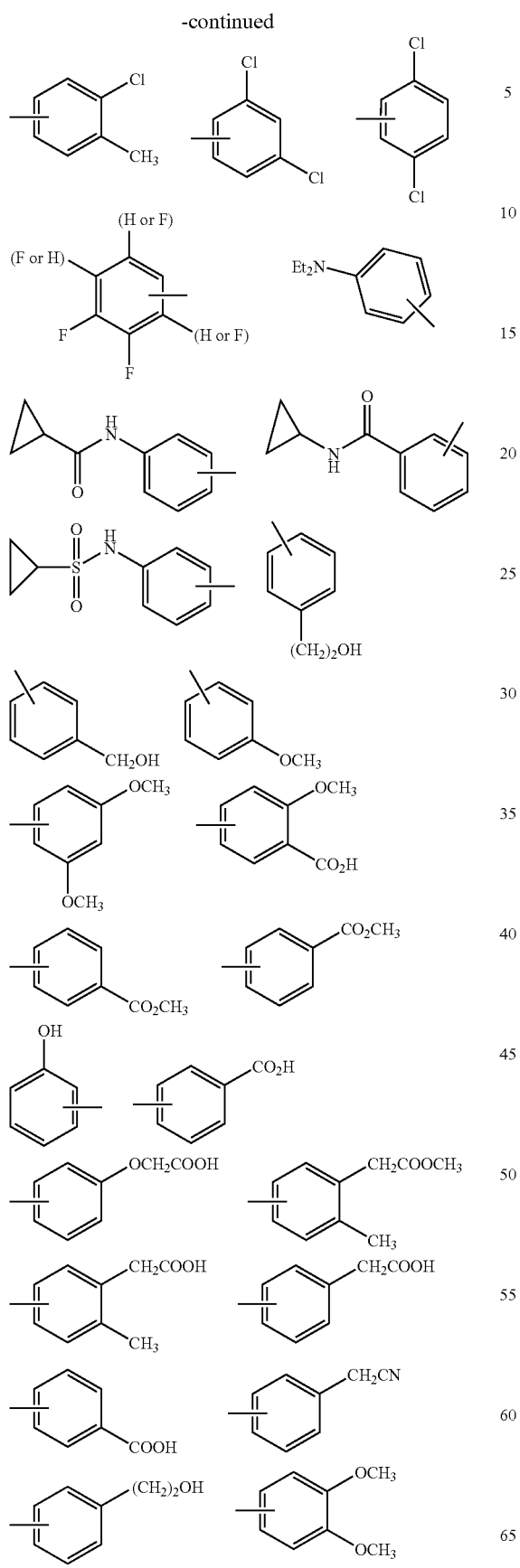
-continued
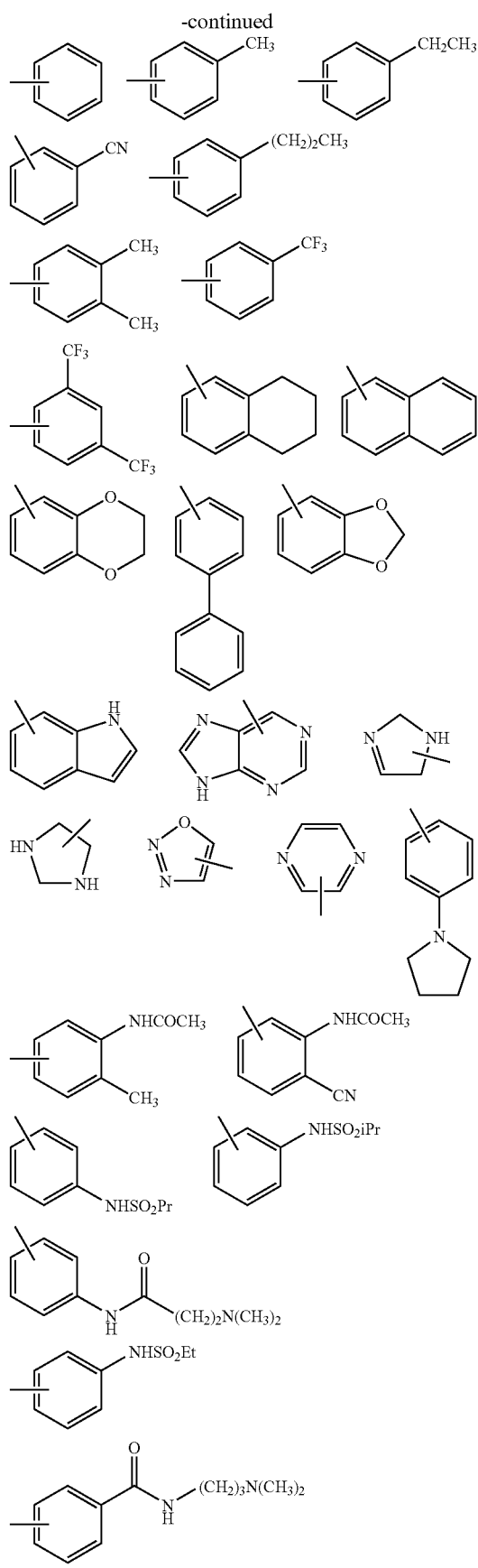

-continued

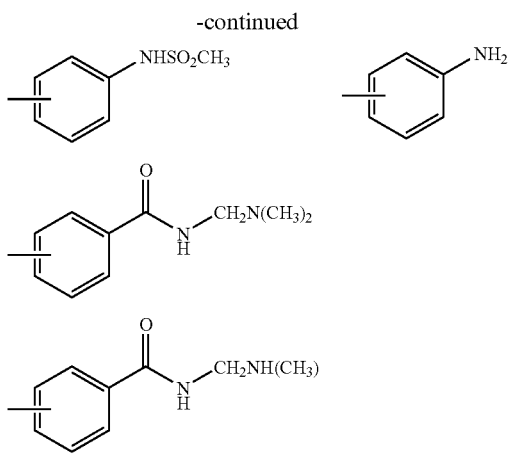

The optionally substituted or fused-ring amino-pyrazole "Pz-NH2" in Scheme 6 can for example be selected from the following structures:

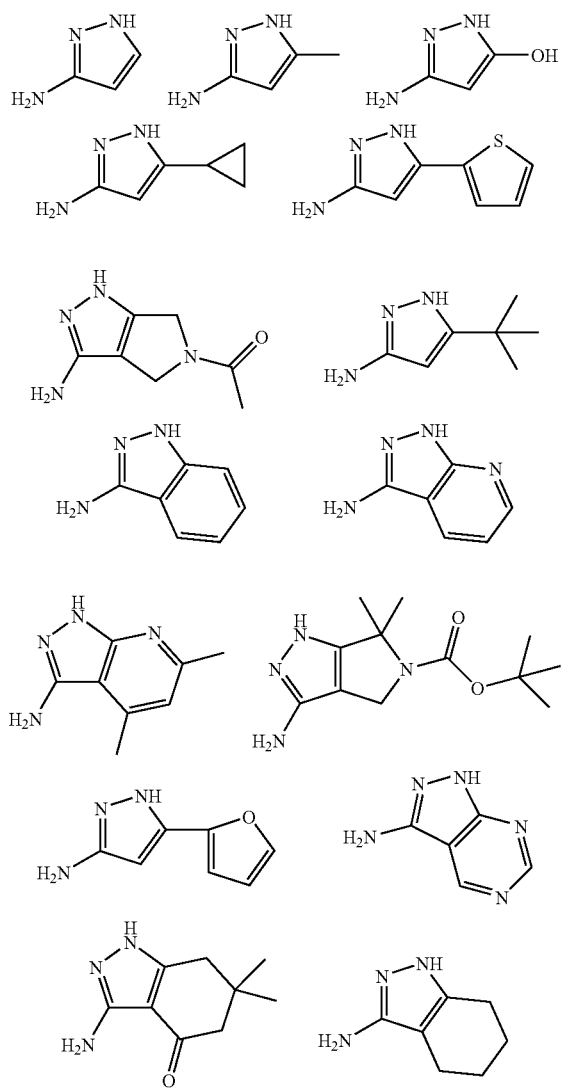

-continued

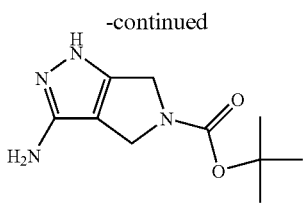

The product 6-G from Scheme 6 can be produced by selection of a nitrile with an Ar- substituent described above or selected from examples shown in the above figure. These nitriles are commercially available or can be produced by reactions known to one skilled in the art including for example by converting the appropriate aldehyde to the acrylonitrile using for examples but not limited to a Wittig reaction or related reactions such as the Peterson Olefination reaction. Generally the desired product will also be made by selecting an appropriate Pz-NH2, chosen for example based on the descriptions above or selected from the figure above showing examples of Pz-NH2, and selecting an R—X—H, chosen for example based on the descriptions above or selected from the figure above showing examples of R—X—H. Examples of some possible products are indicated in Table 1. The present invention also includes molecules 6-G for which reagents for both coupling reactions shown in Scheme 6 are chosen from Pz-NH2.

A nitrile 6-A Ar—CR$^{6''}$=CR6''—CN or Ar—CC—CN is dissolved in usually between 1 and 100 volumes of a solvent for example a mixture of anhydrous toluene and absolute ethanol. The solution is cooled to usually between 0° C. and −70° C. and dry HCl gas is bubbled for between 1 and 24 hours after which the reaction is closed and stirred for between 1 and 72 hours at a temperature usually between −20° C. and room temperature. Workup of the reaction mixture provides the O-ethyl imidate 6-B or the alkynyl analog which can be isolated as the HCl salt. 6-B or the alkynyl analog is dissolved in a solvent for example including but not limited to ethanol and cooled to usually between room temperature and −20° C. and solution of dry ammonia in an alcohol for example methanol or ethanol or a mixture is added. The dry ammonia solution can be purchased commercially or freshly prepared by bubbling ammonia gas through the appropriate solvent. The mixture is stirred at a temperature generally between 0° C. and 50° C. for usually between 1 and 24 hours. The mixture is worked up to provide 6-C or the alkynyl analog.

6-C or the alkynyl analog is dissolved in from 1 to 10 weight equivalents of a solvent including but not limited to methanol. A malonic ester derivative including but not limited to dimethyl malonate (generally from 0.75 to 5 molar equivalents) is added to the solution usually at a temperature between 0° C. and 50° C. The mixture is cooled to usually −20° C. to room temperature and a base for example including but not limited to NaOCH$_3$ (usually from 2 to 10 equivalents) is added slowly over generally between 1 and 120 minutes. The resulting solution is heated to a temperature appropriate to the solvent chosen and heated or refluxed for generally between 1 and 24 hours. Work up provides 6-D or the alkynyl analog.

6-D or the alkynyl analog is slowly added in portions to an excess of a chlorinating reagent including but not limited to POCl$_3$. One skilled in the art can optionally use the chlorinating agent for example POCl$_3$ as the solvent as well as reactant, or can use the chlorinating agent as reactant and optionally a solvent can be selected for example including but not limited to acetonitrile. One skilled in the art can use a base including for example but not limited to Hunig's base (diisopropylethylamine) or other amine bases to improve the effectiveness of the reaction. The mixture is stirred generally for from 1-24 hours at usually between 75° C. and 130° C. The reaction mixture is worked up and purified to give 6-E or the alkynyl analog.

6-E or the alkynyl analog is then coupled to the desired substituents. As illustrated in the Scheme, if the chosen substituents are for example a Pz-NH2 and an R—X—H chosen from the accompanying figures, either the Pz-NH2 can be coupled first followed by the R—X—H proceeding through 6-F, or the R—X—H can be coupled first followed by the Pz-NH2 proceeding through 6-H. If the desired product has two substituents selected from Pz-NH2 the appropriate reaction conditions as described below are used.

To couple Pz-NH$_2$, to a solution of 6-E or 6-H or the alkynyl analog in a solvent including for example but not limited to anhydrous DMA (usually from 1 to 100 equivalents) is added usually between 0.5 and 5 equivalents of an amino-pyrazole which can be chosen from the descriptions in this invention, and optionally a reagent including for example NaI or a catalyst and also optionally a base including but not limited to DIPEA. The mixture is stirred at a temperature generally from 50° C. to 90° C. for usually between 2 and 36 hours. Workup and purification give 6-F or 6-G, respectively, or the alkynyl analog.

To couple R—X—H, 6-E or 6-F or the alkynyl analog is dissolved in the desired R—X—H and heated between generally 50° C. to 110° C. for usually from 0.25 to 12 hours. Optionally a solvent can be chosen including but not limited to anhydrous DMA and also optionally a base including but not limited to DIPEA or TEA and also optionally a reagent including but not limited to NaI or a catalyst can be used to facilitate the reaction. Work up and purification provide the target compound 6-H or 6-G, respectively, or the alkynyl analog.

Alternative coupling methods to that shown in Scheme 6 may be used to increase the effectiveness or selectivity of reaction for certain RXH, for example the addition of a base including but not limited to TEA or DIPEA, and also for example replacement of one or both chlorine atoms by iodine or bromine, and also for example the use of catalysts including but not limited to heavy metal catalysts such as palladium complexes or Cu(I). These approaches are well known to one skilled in the art, and are reported for example in publications such as Gomtsyan et al (*J. Med. Chem.* 2002 45, 3639) and U.S. Pat. No. 5,453,414 which are incorporated herein by reference in their entirety. Additional modifications can be accomplished by use of coupling reactions including but not limited to Suzuki, Stille, Grignard, and Buchwald, as known to one skilled in the art. Optionally, appropriate protection groups can be added and removed to facilitate the reaction, as is known to one skilled in the art. Examples of other coupling reactions can be found in the literature including "Strategic Applications of Named Reactions in Organic Synthesis" (L. Kurti and B. Czako, Elesier Acedemic Press, New York, N.Y., 2005). Examples of protection groups can be found in the literature including "Protective Groups in Organic Synthesis—Third Edition" (T. W. Greene, P. G. M. Wuts, Wiley-Interscience, New York, N.Y., 1999).

The present invention will be understood more readily by reference to the following examples, which are provided by way of illustration and are not intended to be limiting of the present invention.

EXAMPLES

The following abbreviations are used in the examples:

ATP: adenosine triphosphate
Brij-35: polyoxyethyleneglycol dodecyl ether
° C.: degrees Celcius
DMEM: Dulbecco's Modified Eagle's Medium
DMSO: dimethylsulfoxide
DTT: dithiothreitol
g: gram
HEPES: 4-(2-hydroxyethyl)piperazine-1-ethanesulfonic acid
hplc: high performance liquid chromatography
IC$_{50}$ value: concentration of an inhibitor that causes a 50% reduction in a measured activity.
mg: milligram
mL: milliliter
mmol: millimole
MS: mass spectrum
m/z: mass to charge ratio
Pz: optionally modified or substituted or fused pyrazole ring system
Rf: ratio to front (ratio of distance traveled by substance/distance traveled by solvent)
SRB: sulphorhodamine-B
TCA: trichloracetic acid
THF: tetrahydrofuran
tlc thin layer chromatography
br broad
s singlet
d doublet
t triplet
q quartet
dd doublet of doublets
J coupling constant Example 1

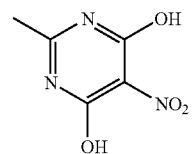

2-methyl-5-nitropyrimidine-4,6-diol

Powdered 4,6-dihydroxy-2-methylpyrimidine (9 g, 71 mmol) was dissolved in trifluoroacetic acid (54 mL). The reaction mixture was cooled in ice-water as nitric acid (4.3 mL) was added dropwise over a period of 30 minutes. During addition the internal temperature was maintained below 15° C. After the addition, the cooling was removed and the reaction stirred overnight. Water (50 mL) was added to the reaction mixture and the resulting solid was filtered and dried under vacuum to obtain 2-methyl-5-nitropyrimidine-4,6-diol (5.8 g). $^1$H NMR (400 MHz, DMSO-$d_6$): δ 12.97 (br, 2H), 2.32 (s, 3H). MS (m/z) 172 (M+1).

Example 2

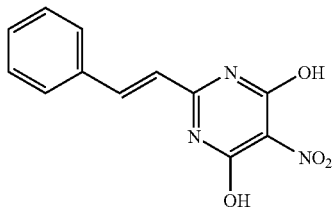

5-nitro-2-[(E)-2-phenylvinyl]pyrimidine-4,6-diol

A mixture of 2-methyl-5-nitropyrimidine-4,6-diol (4.7 g, 27.5 mmol) and benzaldehyde (42 mL, 414 mmol) was treated with piperidine (21.3 mL, 215.3 mmol). The reaction mixture was heated to 90° C. for 2 hrs. The temperature was then increased to 120° C. for 30 min. After cooling the reaction mixture to ambient, methanol (10 mL) and diethyl ether (200 mL) were added sequentially. The resulting solid was collected by filtration and washed with 5% aqueous hydrochloric acid to give 5-nitro-2-[(E)-2-phenylvinyl]pyrimidine-4,6-diol (4.5 g). $^1$H NMR (400 MHz, DMSO-$d_6$): δ 8.15 (d, 1H, J=16.4 Hz), 7.15 (m, 2H), 7.54 (m, 3H), 6.81 (d, 1H, J=16.4 Hz). MS (m/z) 260 (M+1).

Example 3

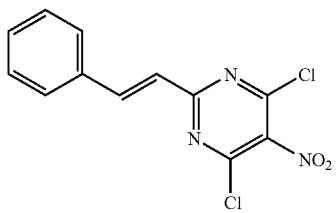

4,6-dichloro-5-nitro-2-[(E)-2-phenylvinyl]pyrimidine

5-Nitro-2-[(E)-2-phenylvinyl]pyrimidine-4,6-diol (2.4 g, 9.63 mmol) was treated with phosphorous oxychloride (10 mL, 106.6 mmol) followed by drop-wise addition of diethylaniline (4 mL, 25.1 mmol; slight exotherm was observed during addition). The reaction mixture was slowly heated at 200° C. After 1.5 hours, the reaction was cooled then poured into crushed ice with stirring. The resulting solid was collected by filtration and dried to give 4,6-dichloro-5-nitro-2-[(E)-2-phenylvinyl]pyrimidine (1.6 g). $^1$H NMR (400 MHz, DMSO-$d_6$): δ 8.15 (d, 1H, J=16.4 Hz), 7.89 (m, 2H), 7.47 (m, 3H), 7.37 (d, 1H, J=16.4 Hz). MS (m/z) 296 (M+1).

Example 4

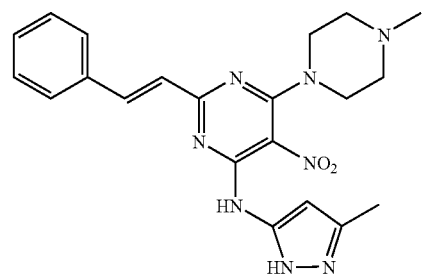

6-(4-methylpiperazin-1-yl)-N-(3-methyl-1H-pyrazol-5-yl)-5-nitro-2-[(E)-2-phenylvinyl]pyrimidin-4-amine To a solution of 4,6-dichloro-5-nitro-2-[(E)-2-phenylvinyl]pyrimidine (200 mg, 0.676 mmol) in THF (5 mL) was added triethylamine (204 mg, 2.03 mmol) and the reaction mixture was stirred for 15 minutes. 3-Amino-5-methyl-pyrazole (66 mg, 0.68 mmol) in THF (3 mL) was added dropwise to the reaction mixture. After 1 hour, N-methylpiperazine (74 mg, 0.74 mmol) in THF (3 mL) was added to the reaction mixture dropwise. The reaction mixture was stirred at room temperature for 1 hour followed by addition of water (10 mL). After stirring for 15 minutes, ethyl acetate (50 mL) was added. The organic layer was separated, dried and the solvent evaporated under reduced pressure. The residue was triturated with chloroform and hexane to obtain 6-(4-methylpiperazin-1-yl)-N-(3-methyl- 1H-pyrazol-5-yl)-5-nitro-2-[(E)-2-phenylvinyl]pyrimidin-4-amine (80 mg). $^1$H NMR (400 MHz, DMSO-$d_6$): δ 12.35 (br, 1H), 10.52 (br, 1H), 7.95 (d, 1H, J=16 Hz), 7.83 (d, 2H, J=6.8 Hz), 7.5 (m, 3H), 7.11 (d, 1H, J=16 Hz), 6.8 (s, 1H), 3.65 (br, 4H), 2.5 (br, 4H), 2.36 (s, 3H), 2.29 (s, 3H). MS (m/z) 421 (M+1).

Examples 5 to 9 were prepared in the same manner as Example 4 by replacing the N-methylpiperazine with the appropriate amine.

Example 5

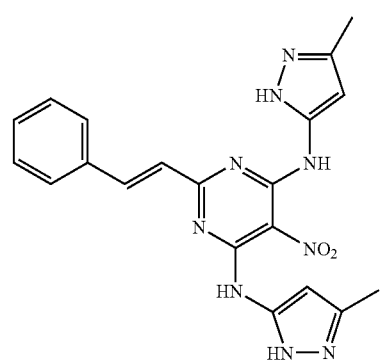

N,N'-bis(3-methyl-1H-pyrazol-5-yl)-5-nitro-2-[(E)-2-phenylvinyl]pyrimidin-4,6-diamine By replacing N-methylpiperazine with 3-amino-5-methylpyrazole was obtained N,N'-bis(3-methyl-1H-pyrazol-5-yl)-5-nitro-2-[(E)-2-phenylvinyl]-pyrimidin-4,6-diamine in 44% yield. $^1$H NMR (400 MHz, DMSO-d$_6$): δ 12.41 (br, 2H), 11.35 (br, 2H), 7.92 (d, 1H, J=16 Hz), 7.79 (d, 1H, J=6.8 Hz), 7.76 (m, 3H), 7.16 (d, 1H, J=16 Hz), 6.80 (s, 2H), 2.31 (s, 6H). MS (m/z) 418 (M+1).

Example 6

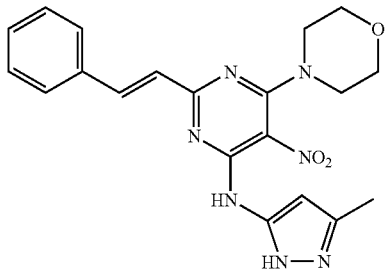

N-(3-methyl-1H-pyrazol-5-yl)-5-nitro-6-(morpholin-4-yl)-2-[(E)-2-phenylvinyl]pyrimidin-4-amine By replacing N-methylpiperazine with morpholine was obtained N-(3-methyl-1H-pyrazol-5-yl)-6-(morpholin-4-yl)-5-nitro-2-[(E)-2-phenylvinyl]-pyrimidin-4-amine in 15% yield after preparative hplc chromatography. $^1$H NMR (400 MHz, CDCl$_3$): δ 10.56 (br, 1H), 7.88 (d, 1H, J=16 Hz), 7.65 (d, 2H, J=6.8 Hz), 7.40 (m, 3H), 7.06 (d, 1H, J=16 Hz), 6.38 (s, 1H), 3.83 (m, 4H), 3.69 (m, 4H), 2.37 (s, 3H). MS (m/z) 408 (M+1).

Example 7

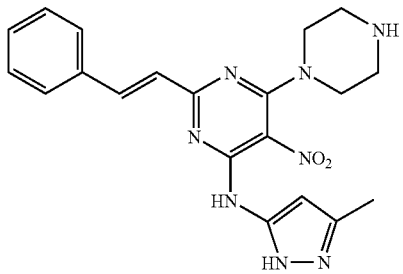

N-(3-methyl-1H-pyrazol-5-yl)-5-nitro-6-(piperazin-1-yl)-2-[(E)-2-phenylvinyl]pyrimidin-4-amine By replacing N-methylpiperazine with piperazine was obtained N-(3-methyl-1H-pyrazol-5-yl)-5-nitro-6-(piperazin-1-yl)-2-[(E)-2-phenylvinyl]-pyrimidin-4-amine in 17% yield after preparative hplc. $^1$H NMR (400 MHz, CDCl$_3$): δ 10.58 (br, 1H), 7.87 (d, 1H, J=16 Hz), 7.62 (m, 2H), 7.38 (m, 3H), 6.96 (d, 1H, J=16 Hz), 6.37 (s, 1H), 3.74 (m, 4H), 3.58 (m, 4H), 2.36 (s, 3H). MS (m/z) 407 (M+1).

Example 8

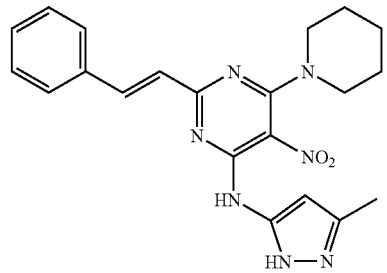

N-(3-methyl-1H-pyrazol-5-yl)-5-nitro-6-(piperidin-1-yl)-2-[(E)-2-phenylvinyl]pyrimidin-4-amine By replacing N-methylpiperazine with piperidine was obtained N-(3-methyl-1H-pyrazol-5-yl)-5-nitro-6-(piperidin-1-yl)-2-[(E)-2-phenylvinyl]-pyrimidin-4-amine in 16% yield after preparative hplc. $^1$H NMR (400 MHz, CDCl$_3$): δ 10.58 (br, 1H), 7.87 (d, 1H, J=16 Hz), 7.62 (m, 2H), 7.38 (m, 3H), 6.95 (d, 1H, J=16 Hz), 6.35 (s, 1H), 3.58 (m, 4H), 2.36 (s, 3H), 1.4-1.9 (m, 6H). MS (m/z) 406 (M+1).

Example 9

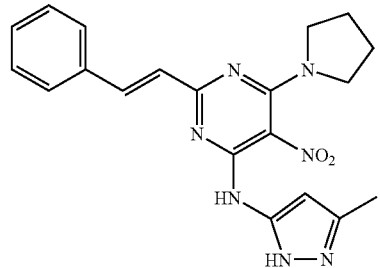

N-(3-methyl-1H-pyrazol-5-yl)-5-nitro-6-(pyrrolidin-1-yl)-2-[(E)-2-phenylvinyl]pyrimidin-4-amine By replacing N-methylpiperazine with pyrrolidine was obtained N-(3-methyl-1H-pyrazol-5-yl)-5-nitro-6-(pyrrolidin-1-yl)-2-[(E)-2-phenylvinyl]-pyrimidin-4-amine in 14% yield after preparative chromatography. $^1$H NMR (400 MHz, CDCl$_3$): δ 10.5 (br, 1H), 7.9 (d, 1H, J=16 Hz), 7.65 (m, 2H), 7.39 (m, 3H), 7.13 (d, 1H, J=16 Hz), 6.29 (s, 1H), 2.5-3.5 (m, 4H), 2.37 (s, 3H), 2.02 (m, 4H). MS(m/z) 392 (M+1).

Example 10

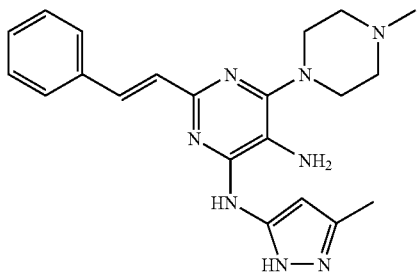

6-(4-methylpiperazin-1-yl)-N-(3-methyl-1H-pyrazol-5-yl)-2-[(E)-2-phenylvinyl]pyrimidin-4,5-diamine A solution of tin (II) chloride dihydrate (600 mg, 4.43 mmol) in concentrated hydrochloric acid (1 mL), 9.04 mmol) was cooled below 10° C. A solution of 6-(4-methylpiperazin-1-yl)-N-(3-methyl-1H-pyrazol-5-yl)-5-nitro-2-[(E)-2-phenylvinyl]pyrimidin-4-amine (Example 4, 400 mg, 0.95 mmol) in methanol (20 mL) was added dropwise to the reaction mixture. The reaction was allowed to come to ambient temperature and was then heated to 60° C. for 3 hours. Progress of the reaction was monitored by TLC. The reaction mixture was reduced to $\frac{1}{3}^{rd}$ volume of the original volume under vacuum. The residue was diluted with ethyl acetate (40 mL) and 1N NaOH (20 mL) was added to the reaction mixture. The organic layer was separated, dried and the solvent evaporated under reduced pressure. The residue was then triturated with ethyl acetate and hexane to afford 6-(4-methylpiperazin-1-yl)-N-(3-methyl-1H-pyrazol-5-yl)-2-[(E)-2-phenylvinyl]pyrimidin-4,5-diamine as a yellow solid (200 mg). $^1$H NMR (400 MHz, DMSO-d$_6$): δ 7.94 (br, 1H), 7.70 (d, 1H, J=16 Hz), 7.59 (m, 2H) 7.38 (m, 2H), 7.29 (m, 1H), 7.05 (d, 1H, J=16 Hz), 6.36 (br, 1H), 3.44 (br, 2H), 3.3 (br, 4H), 2.59 (br, 4H), 2.36 (s, 3H), 2.33 (s, 3H). MS (m/z) 391 (M+1).

Examples 11 to 15 were prepared in the same manner as Example 10 from the appropriate starting material.

Example 11

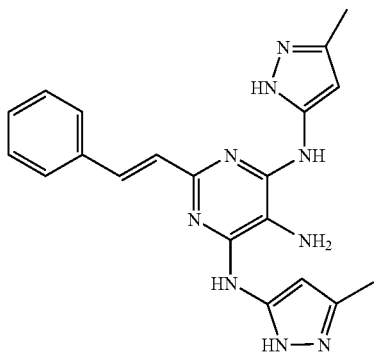

N,N'-bis(3-methyl-1H-pyrazol-5-yl)-2-[(E)-2-phenylvinyl]pyrimidin-4,5,6-triamine From Example 5, N,N'-bis(3-methyl-1H-pyrazol-5-yl)-5-nitro-2-[(E)-2-phenylvinyl]pyrimidin-4,6-diamine, was obtained NN'-bis(3-methyl-1H-pyrazol-5-yl)-2-[(E)-2-phenylvinyl]pyrimidin-4,5,6-triamine in 43% yield. $^1$H NMR (400 MHz, DMSO-d$_6$): δ 11.86 (br, 2H), 8.41 (br, 2H), 7.2-7.8 (m, 6H), 7.0-7.1 (br, 1H), 6.5 (br, 1H), 2.11 (s, 6H). MS (m/z) 388 (M+1).

Example 12

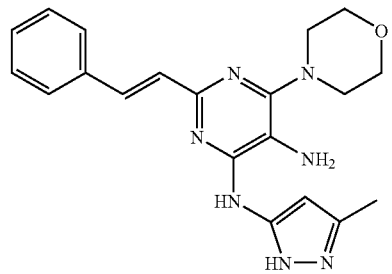

N-(3-methyl-1H-pyrazol-5-yl)-6-(morpholin-4-yl)-2-[(E)-2-phenylvinyl]pyrimidin-4,5-diamine From Example 6, N-(3-methyl-1H-pyrazol-5-yl)-5-nitro-6-(morpholin-4-yl)-2-[(E)-2-phenylvinyl]pyrimidin-4-amine, was obtained N-(3-methyl-1H-pyrazol-5-yl)-6-(morpholin-4-yl)-2-[(E)-2-phenylvinyl]pyrimidin-4,5-diamine in 21% yield after preparative hplc. $^1$H NMR (400 MHz, CDCl$_3$): δ 11.35 (br, 1H), 7.58 (m, 2H), 7.42 (m, 4H), 6.74 (d, 1H, J=16 Hz), 5.82 (s, 1H), 3.67 (m, 4H), 3.27 (m, 4H), 2.17 (s, 3H). MS (m/z) 378 (M+1).

Example 13

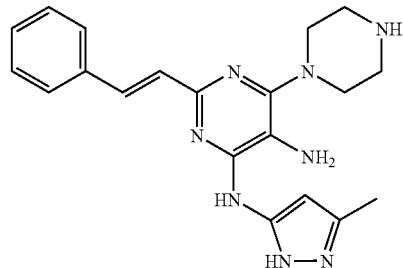

N-(3-methyl-1H-pyrazol-5-yl)-6-(piperazin-1-yl)-2-[(E)-2-phenylvinyl]pyrimidin-4,5-diamine From Example 7, N-(3-methyl-1H-pyrazol-5-yl)-5-nitro-6-(piperazin-1-yl)-2-[(E)-2-phenylvinyl]pyrimidin-4-amine, was obtained N-(3-methyl-1H-pyrazol-5-yl)-6-(piperazin-1-yl)-2-[(E)-2-phenylvinyl]pyrimidin-4,5-diamine in 17% yield after preparative hplc. $^1$H NMR (400 MHz, CDCl$_3$): δ

11.3 (br, 1H), 7.31-7.63 (m, 6H), 6.82 (d, 1H, J=16 Hz), 5.85 (s, 1H), 3.28 (m, 4H), 2.22 (s, 3H), 1.65 (m, 4H). MS (m/z) 377 (M+1).

Example 14

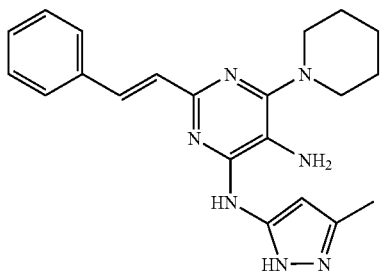

N-(3-methyl-1H-pyrazol-5-yl)-6-(piperidin-1-yl)-2-[(E)-2-phenylvinyl]pyrimidin-4,5-diamine From Example 8, N-(3-methyl-1H-pyrazol-5-yl)-5-nitro-6-(piperidin-1-yl)-2-[(E)-2-phenylvinyl]pyrimidin-4-amine, was obtained N-(3-methyl-1H-pyrazol-5-yl)-6-(piperidin-1-yl)-2-[(E)-2-phenylvinyl]pyrimidin-4,5-diamine in 18% yield. $^1$H NMR (400 MHz, CDCl$_3$): δ 7.73 (d, 1H, J=16 Hz), 7.62 (d, 2H, J=7.2 Hz), 7.39 (t, 2H, J=7.2 Hz), 7.32 (m, 1H), 7.09 (d, 1H, J=16 Hz), 6.3 (s, 1H), 3.29 (br, 2H), 3.22 (br, 4H), 2.36 (s, 3H), 1.4-1.9 (m, 6H). MS (m/z) 376 (M+1).

Example 15

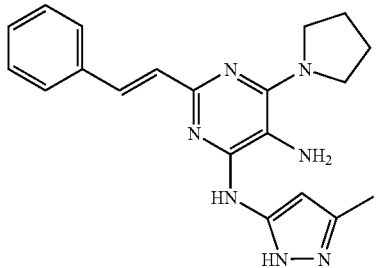

N-(3-methyl-1H-pyrazol-5-yl)-6-(pyrrolidin-1-yl)-2-[(E)-2-phenylvinyl]pyrimidin-4,5-diamine From Example 9, N-(3-methyl-1H-pyrazol-5-yl)-5-nitro-6-(pyrrolidin-1-yl)-2-[(E)-2-phenylvinyl]pyrimidin-4-amine, was obtained N-(3-methyl-1H-pyrazol-5-yl)-6-(pyrrolidin-1-yl)-2-[(E)-2-phenylvinyl]pyrimidin-4,5-diamine in 20% yield. $^1$H NMR (400 MHz, CDCl$_3$): δ 7.88 (br, 1H), 7.71 (d, 1H, J=16 Hz), 7.59 (d, 2H, J=7.2 Hz), 7.39 (t, 2H, J=7.2 Hz), 7.29 (m, 1H), 7.00 (d, 1H, J=16 Hz), 5.95 (s, 1H), 3.73 (m, 4H), 2.67 (br, 2H), 2.30 (s, 3H), 1.97 (m, 4H). MS (m/z) 362 (M+1).

Example 16

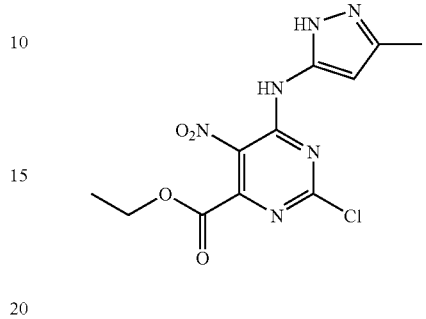

ethyl 2-chloro-6-[(3-methyl-1H-pyrazol-5-yl)amino]-5-nitropyrimidine-4-carboxylate To a solution of commercially available ethyl 2,6-dichloro-5-nitropyrimidine-4-carboxylate (Matrix Scientific, 1.00 g, 3.76 mmol, 1.0 equiv) and 2,6-lutidine (0.65 mL, 5.60 mmol, 1.5 equiv) in anhydrous 1,4-dioxane (5 mL) at room temperature was added drop-wise a solution of 5-methyl-3-aminopyrazole (0.38 g, 3.95 mmol, 1.05 equiv) in anhydrous 1,4-dioxane (5 mL). The solution was stirred at room temperature for 30 min, diluted with ethyl acetate (100 mL), washed with 1 N hydrochloric acid (50 mL×3) and brine (50 mL×1), dried over Na$_2$SO$_4$, and concentrated to dryness to yield a light-brown solid as Example 16 (1.16 g, 95%): R$_f$ 0.55 (60% ethyl acetate/hexane); MS m/z 327, calcd 327 (C$_{11}$H$_{11}$ClN$_6$O$_4$+H).

Example 17

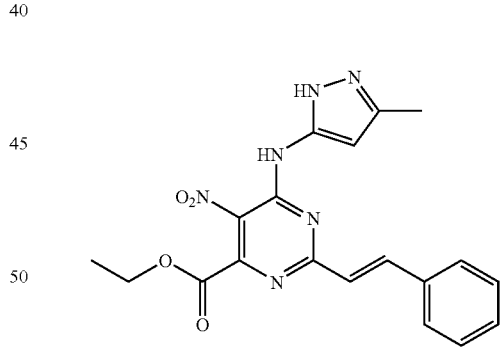

ethyl 6-[(3-methyl-1H-pyrazol-5-yl)amino]-5-nitro-2-[(E)-2-phenylvinyl]pyrimidine-4-carboxylate To a glass vessel containing Example 16 (100 mg, 0.31 mmol, 1.0 equiv), anhydrous potassium carbonate (64 mg, 0.46 mmol, 1.5 equiv), trans-2-phenylvinylboronic acid (69 mg, 0.46 mmol, 1.5 equiv), and tetrakis(triphenylphosphine)palladium(0) (18 mg, 0.015 mmol, 0.05 equiv) was added anhydrous toluene (3 mL) under nitrogen atmosphere. The suspension was de-gassed by bubbling nitrogen through for 2-3 minutes. The suspension was then heated with rapid stirring at 70° C. for 8 hours, cooled to room temperature, diluted with water (50 mL), and extracted with dichloromethane (50 mL×3). The combined extracts were and concentrated under reduced pressure. The residue was purified on a silica gel flash column with 0-50% ethyl acetate/hexane to yield Example 17 as an orange solid (62 mg, 51%): $R_f$ 0.40 (60% ethyl acetate/hexane); MS m/z 395, calcd 395 ($C_{19}H_{18}N_6O_4$+H).

Example 18

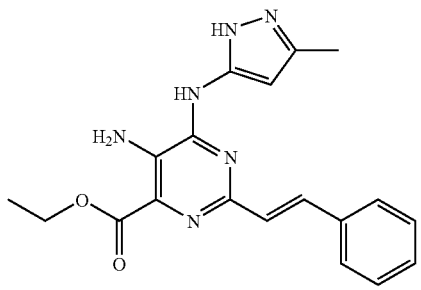

ethyl 5-amino-6-[(3-methyl-1H-pyrazol-5-yl)amino]-2-[(E)-2-phenylvinyl]pyrimidine-4-carboxylate To a solution of Example 16 (0.40 g, 1.02 mmol, 1 equiv) in dimethylsulfoxide (5 mL) and acetonitrile (20 mL) was added zinc dust (0.66 g, 10.09 mmol, 10 equiv), followed by the addition of ammonium formate (0.63 g, 10.00 mmol, 10 equiv). The suspension was stirred at room temperature for 30 minutes. The solid was filtered off with a celite pad and the filtrate was concentrated under reduced pressure to yield the crude product that was purified by column chromatography on silica gel using 5% methanol in chloroform, yielding Example 18 as a yellow solid (70 mg, 19%): $R_f$ 0.55 (10% methanol/dichloromethane); $^1$H NMR (300 MHz, DMSO-$d_6$) δ 12.19 (br s, 1H), 9.60 (br s, 1H), 7.63 (d, J=7.5 Hz, 12H), 7.53 (d, J=15.9 Hz, 1H), 7.35-7.45 (m, 2H), 7.26-7.34 (m, 1H), 7.07 (d, J=16.0 Hz, 1H), 7.04 (br s, 2H), 6.75 (s, 1H), 4.38 (q, J=7.8 Hz, 2H), 2.32 (s, 3H), 1.34 (t, J=7.8 Hz, 3H); MS m/z 365, calcd 365 ($C_{19}H_{20}N_6O_2$+H).

Examples 19 to 23 were prepared in the same manner as Example 17 starting from Example 16 by subsituting the appropriate vinylboronic acid for trans-2-phenylvinylboronic acid in the synthetic sequence.

Example 19

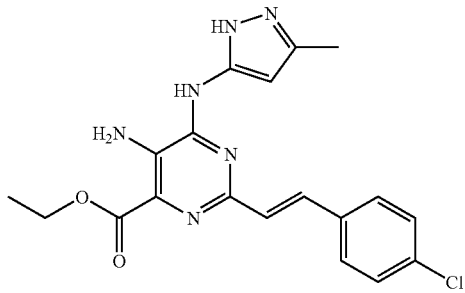

ethyl 5-amino-2-[(E)-2-(4-chlorophenyl)vinyl]-6-[(3-methyl-1H-pyrazol-5-yl)amino]pyrimidine-4-carboxylate By substituting trans-2-(4-chlorophenyl)vinylboronic acid for trans-2-phenylvinylboronic acid was obtained a light-yellow solid (14 mg): $^1$H NMR (400 MHz, DMSO-$d_6$) δ 12.12 (br s, 1H), 9.52 (s, 1H), 7.69 (d, J=8.3 Hz, 1H), 7.49 (d, J=16.0 Hz, 1H), 7.44 (d, J=8.3 Hz, 2H), 7.09 (d, J=16.0 Hz, 1H), 7.04 (s, 2H), 6.75 (s, 1H), 4.34 (q, J=7.0 Hz, 2H), 2.32 (s, 3H), 1.34 (t, J=7.0 Hz, 3H); MS m/z 399, calcd 399 ($C_{19}H_{19}ClN_6O_2$+H).

Example 20

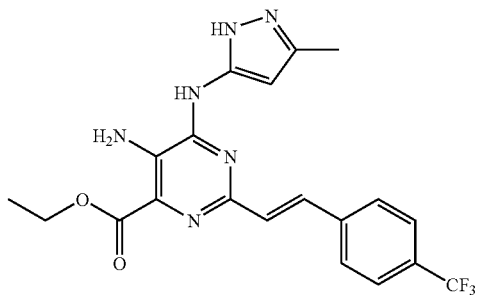

ethyl 5-amino-6-[(3-methyl-1H-pyrazol-5-yl)amino]-2-{(E)-2-[4-(trifluoromethyl)phenyl]vinyl}pyrimidine-4-carboxylate By substituting trans-2-(4-(trifluoromethyl)phenyl)vinylboronic acid for trans-2-phenylvinylboronic acid was obtained a light-yellow solid (60 mg): $^1$H NMR (400 MHz, DMSO-$d_6$) δ 10.20 (br s, 1H), 7.89 (d, J=8.0 Hz, 2H), 7.77 (d, J=8.0 Hz, 2H), 7.66 (d, J=16.0 Hz, 1H), 7.41-7.37 (m, 3H), 6.76 (s, 1H), 4.40 (q, J=6.9 Hz, 2H), 2.34 (s, 3H), 1.37 (t, J=6.9 Hz, 3H); MS m/z 433, calcd 433 ($C_{20}H_{19}F_3N_6O_2$+H).

Example 21

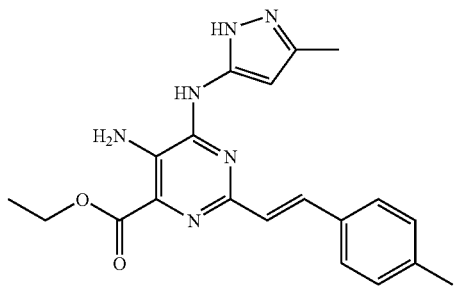

ethyl 5-amino-2-[(E)-2-(4-methylphenyl)vinyl]-6-[(3-methyl-1H-pyrazol-5-yl)amino]pyrimidine-4-carboxylate By substituting trans-2-(4-methylphenyl)vinylboronic acid for trans-2-phenylvinylboronic acid was obtained a light-yellow solid (22 mg): $^1$H NMR (400 MHz, DMSO-$d_6$) δ 12.13 (br s, 1H), 9.49 (s, 1H), 7.55-7.48 (m, 3H), 7.21 (d, J=7.9 Hz, 2H), 7.02-7.00 (m. 3H), 6.78 (s, 1H), 4.34 (q, J=7.1 Hz, 2H), 2.33 (s, 6H), 1.34 (t, J=7.1 Hz, 3H); MS m/z 379, calcd 379 ($C_{20}H_{22}N_6O_2$+H).

Example 22

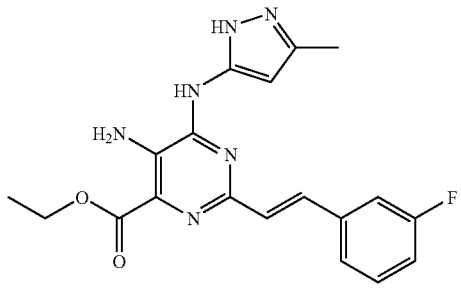

ethyl 5-amino-2-[(E)-2-(3-fluorophenyl)vinyl]-6-[(3-methyl-1H-pyrazol-5-yl)amino]pyrimidine-4-carboxylate By substituting trans-2-(3-fluorophenyl)vinylboronic acid for trans-2-phenylvinylboronic acid was obtained a light-yellow solid (13 mg): $^1$H NMR (400 MHz, DMSO-$d_6$) δ 12.11 (br s, 1H), 9.51 (s, 1H), 7.56-7.38 (m, 4H), 7.14-7.04 (m, 4H), 6.76 (s, 1H), 4.33 (q, J=7.1 Hz, 2H), 2.31 (s, 3H), 1.32 (t, J=7.1 Hz, 3H); MS m/z 383, calcd 383 ($C_{19}H_{19}FN_6O_2$+H).

Example 23

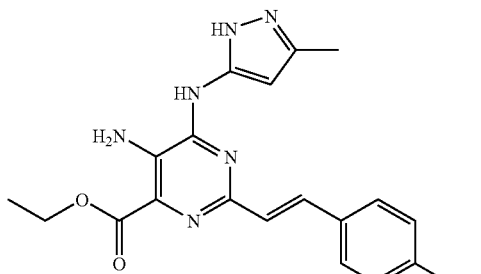

ethyl 5-amino-2-[(E)-2-(4-methoxyphenyl)vinyl]-6-[(3-methyl-1H-pyrazol-5-yl)amino]pyrimidine-4-carboxylate By substituting trans-2-(4-methoxyphenyl)vinylboronic acid for trans-2-phenylvinylboronic acid was obtained a light-yellow solid (76 mg): $^1$H NMR (400 MHz, DMSO-$d_6$) δ 7.70 (d, J=15.7 Hz, 1H), 7.59 (d, J=8.7 Hz, 2H), 7.22 (d, J=15.7 Hz, 1H), 7.02 (d, J=8.7 Hz, 2H), 6.48 (br s, 4H), 4.42 (q, J=7.1 Hz, 2H), 3.79 (s, 3H), 2.32 (s, 3H), 1.35 (t, J=7.1 Hz, 3H); MS m/z 395, calcd 395 ($C_{20}H_{22}N_6O_3$+H).

Example 24

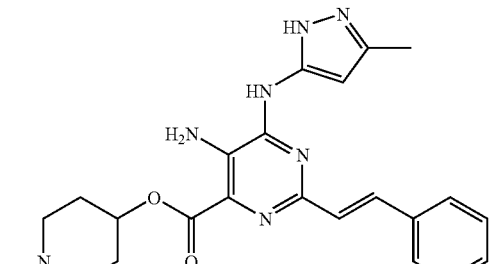

1-methylpiperidin-4-yl 5-amino-6-[(3-methyl-1H-pyrazol-5-yl)amino]-2-[(E)-2-phenylvinyl]pyrimidine-4-carboxylate A mixture of Example 18 (4.5 g, 12.3 mmol, 1 equiv) and 4-hydroxy-N-methyl piperidine (40 mL) was slowly added titanium isopropoxide (1 mL). The reaction was heated to reflux overnight. The excess of the alcohol was distilled off and the resultant solid was purified by column chromatography on silica gel using 3% methanol in dichloromethane to afford Example 24 as a yellow solid (1.55 g, 29%): $^1$H NMR (400 MHz, DMSO-$d_6$) δ 12.11 (s, 1H), 9.49 (s, 1H), 7.64-7.62 (m, 2H), 7.53 (d, J=16.0 Hz, 1H), 7.40-7.27 (m, 3H), 7.05-6.98 (m, 3H), 6.76 (s, 1H), 4.88 (m, 1H), 2.73-2.49 (m, 2H), 2.30 (s, 3H), 2.15 (m, 5H), 1.97-1.93 (m, 2H), 1.77-1.69 (m, 2H); MS m/z 434, calcd 434 ($C_{23}H_{27}N_7O_2$+H).

Example 25

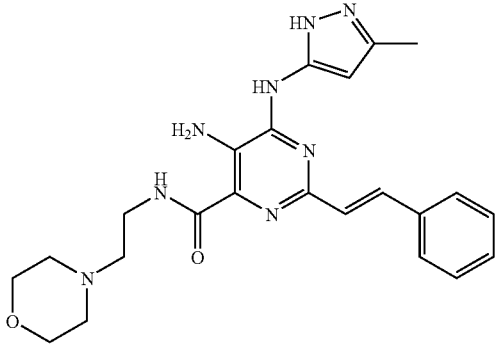

N-(2-morphholin-4-ylethyl)-5-amino-6-[(3-methyl-1H-pyrazol-5-yl)amino]-2-[(E)-2-phenylvinyl]pyrimidine-4-carboxamide To a mixture of Example 18 (2.5 g, 6.9 mmol, 1 equiv) in dry dichloromethane and 2-morpholin-4-ylethylamine (1.8 g, 13.7 mmol, 2 equiv) at 0° C. was added trimethylaluminium (28 mL, 54.8 mmol, 8 equiv) dropwise in about one hour. The reaction was brought to room temperature and stirred for another 4 hours. The reaction was carefully quenched with 1.5 N hydrochloric acid (20 mL). The resultant solid was collected and purified by column chromatography on silica gel using 4% methanol in dichloromethane to yield Example 25 as a yellow solid (1.1 g, 36%): $^1$H NMR (400 MHz, DMSO-$d_6$) δ 12.08 (s, 1H), 9.34 (s, 1H), 8.75 (s, 1H), 7.64-7.60 (m, 3H), 7.42-7.39 (m, 2H), 7.30 (m, 1H), 7.14 (s, 2H), 7.02 (d, J=16.0 Hz, 1H), 6.77 (s, 1H), 3.61-3.59 (m, 4H), 3.41-3.38 (m, 2H), 2.53-2.49 (m, 6H), 2.29 (s, 3H); MS m/z 449, clcad 449 ($C_{23}H_{28}N_8O_2$+H).

Example 26

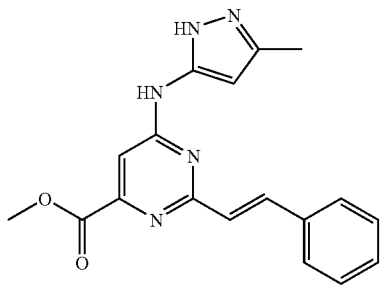

methyl 6-[(3-methyl-1H-pyrazol-5-yl)amino]-2-[(E)-2-phenylvinyl]pyrimidine-4-carboxylate By substituting commercially available methyl 2,4-dichloropyrimidine-6-carboxylate for ethyl 2,6-dichloro-5-nitropyrimidine-4-carboxylate in the reaction sequence used to produced Example 17 was obtained Example 26 as a light-yellow solid (30 mg): $^1$H NMR (300 MHz, DMSO-$d_6$) δ 10.30 (br s, 1H), 7.85 (d, J=16.0 Hz, 1H), 7.65-7.75 (m, 2H), 7.33-7.48 (m, 4H), 7.19 (d, J=16.0 Hz, 1H), 6.40 (br s, 1H), 3.89 (s, 3H), 2.27 (s, 3H); MS m/z 336, calcd 336 ($C_{18}H_{17}N_5O_2$+H).

Example 27

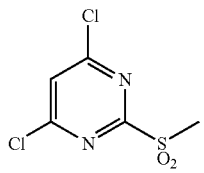

4,6-dichloro-2-(methylsulfonyl)pyrimidine

Commercially available 4,6-dichloro-2-methylthiopyrimidine (Aldrich, 21.0 g, 107.0 mmol, 1 equiv) was dissolved in dichloromethane and cooled with an ice-bath. 3-chlorobenzoyl peroxide (60.0 g, 77% wt, 268.0 mmol, 2.5 equiv) was added in small portions. The resulting white suspension was stirred at room temperature for 4 hours, washed with 1 M sodium thiosulfate/saturated sodium bicarbonate (1:1, v/v, 200 mL×3) and saturated sodium bicarbonate (100 mL×3), and brine (100 mL×1). The organic solution was dried and concentrated under reduced pressure. After drying under high vacuum for overnight Example 27 was obtained as a white solid: (22.0 g, 91%): $R_f$ 0.20 (20% ethyl acetate/hexane); MS m/z 227, calcd 227 ($C_5H_4Cl_2N_2O_2S$+H).

Example 28

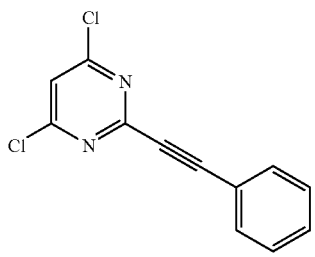

4,6-dichloro-2-(phenylethynyl)pyrimidine

Example 27 (4.54 g, 20.00 mmol, 1 equiv) was dissolved in anhydrous tetrahydrofuran (50 mL) and cooled to −20° C. Phenylacetylenylmagnesium bromide (22.00 mL, 1.0 M in tetrahydrofuran, 22.00 mmol, 1.1 equiv) was added dropwise with vigorous stirring. The solution was stirred from −20° C. to room temperature for overnight, diluted with ethyl acetate (300 mL), and added to 1 N hydrochloric acid (200 mL). The mixture was vigorously stirred for 5 minutes. The organic layer was collected, and the aqueous layer was extracted with more ethyl acetate (100 mL×2). The combined organic solution was dried over $Na_2SO_4$, concentrated under reduced pressure, and dried under high vacuum for overnight to afford the Example 28 as an off-white solid (5.00 g, quantitative): $R_f$ 0.75 (20% ethyl acetate/hexane); MS m/z 249, calcd 249 ($C_{12}H_6N_2Cl_2$+H).

Example 29

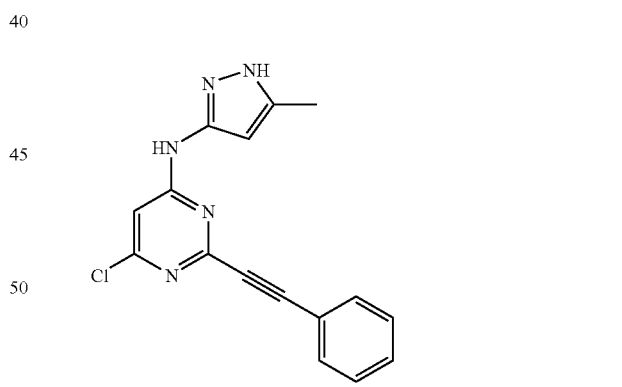

6-chloro-N-(3-methyl-1H-pyrazol-5-yl)-2-(phenylethynyl)pyrimidin-4-amine

Example 28 (5.00 g, 20.00 mmol, 1 equiv) was dissolved in anhydrous dimethylacetamide (20 mL). 5-Methyl-2-aminopyrazole (2.14 g, 22.00 mmol, 1.1 equiv), sodium iodide (3.60 g, 24.00 mmol, 1.2 equiv), and di-isopropylethylamine (4.18 mL, 24.00 mmol, 1.2 equiv) were added. The solution was heated at 90° C. for overnight, cooled to room temperature, diluted with ethyl acetate (200 mL), washed with saturated sodium bicarbonate (200 mL×3), dried and concentrated under reduced pressure. The resulting crude product was purified with flash chromatography on silica gel using 0%~4% methanol/dichloromethane to yield Example 29 as a yellow solid (5.51 g, 89%): $R_f$ 0.40 (5% methanol/dichloromethane); $^1$H NMR (300 MHz, DMSO-d$_6$) δ 12.13 (br s, 1H), 10.39 (s, 1H), 7.63 (d, J=7.5 Hz, 2H), 7.7.40-7.60 (m, 4H), 5.95 (br s, 1H), 2.22 (s, 3H); MS m/z 310, calcd 310 ($C_{16}H_{12}ClN_5$+H).

Example 30

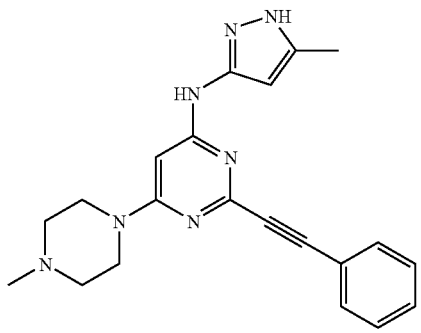

6-(4-methylpiperazin-1-yl)-N-(3-methyl-1H-pyrazol-5-yl)-2-(phenylethynyl)pyrimidin-4-amine Example 29 (2.80 g, 9.04 mmol, 1 equiv) was dissolved in anhydrous 1,4-dioxane (10 mL). N-methylpiperazine (1.10 mL, 9.92 mmol, 1.1 equiv), 4-dimethylaminopyridine (0.055 g, 0.45 mmol, 0.05 equiv), and di-isopropylethylamine (1.89 mL, 10.85 mmol, 1.2 equiv) were added. The solution was stirred at 100° C. for 2 hours, cooled to room temperature, and concentrated under reduced pressure. The residue was purified with flash chromatography on silica gel using 0%~10% methanol/dichloromethane to give the Example 30 as a light-yellow solid (3.00 g, 89%): $R_f$ 0.10 (5% methanol/dichloromethane); $^1$H NMR (300 MHz, DMSO-d$_6$) δ 11.90 (br s, 1H), 9.43 (s, 1H), 7.57 (d, J=7.5 Hz, 2H), 7.40-7.50 (m, 3H), 6.80 (br s, 1H), 5.82 (s, 1H), 3.51 (br s, 4H), 2.43 (br s, 4H), 2.27 (s, 3H), 2.18 (s, 3H); MS m/z 374, calcd 374 ($C_{21}H_{23}N_7$+H).

Example 31

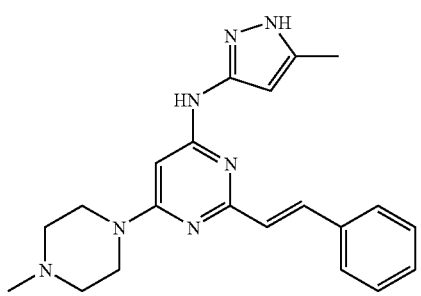

6-(4-methylpiperazin-1-yl)-N-(3-methyl-1H-pyrazol-5-yl)-2-[(E)-2-phenylvinyl]pyrimidin-4-amine Example 30 (2.54 g, 6.80 mmol, 1 equiv) was dissolved in anhydrous tetrahydrofuran (50 mL) and cooled with an ice-water bath. Lithium aluminum hydride (5.61 mL, 1.0 M in tetrahydrofuran, 5.61 mmol, 0.83 equiv) was added dropwise with rapid stirring. The solution was stirred from 0° C. to room temperature for 12 hours. The reaction was cooled to 0° C. and slowly quenched with methanol (5 mL). Saturated sodium potassium tartrate (500 mL) was added to the reaction mixture. The resulting suspension was rapidly stirred at room temperature until a clear solution was obtained. The solution was then extracted with ethyl acetate (100 mL×5). The combined extracts were dried and concentrated under reduced pressure. Flash chromatography on silica gel with 0%~8% methanol/dichloromethane afforded Example 31 as an off-white solid (1.55 g, 61%): $R_f$ 0.30 (10% methanol/dichloromethane); $^1$H NMR (300 MHz, DMSO-d$_6$) δ 11.80 (br s, 1H), 9.08 (s, 1H), 7.72 (d, J=15.9 Hz, 1H), 7.63 (d, J=7.2 Hz, 2H), 7.28-7.45 (m, 3H), 6.92 (d, J=15.9 Hz, 1H), 6.62 (br s, 1H), 5.95 (s, 1H), 3.56 (br s, 4H), 2.45 (br s, 4H), 2.26 (s, 3H), 2.20 (s, 3H); MS m/z 376, calcd 376 ($C_{21}H_{25}N_7$+H).

Example 31 was also made via Scheme 6 as described below.

Example 32

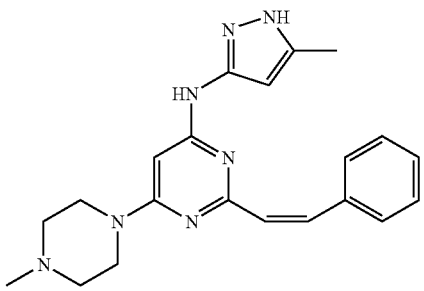

6-(4-methylpiperazin-1-yl)-N-(3-methyl-1H-pyrazol-5-yl)-2-[(Z)-2-phenylvinyl]pyrimidin-4-amine Example 30 (38 mg, 0.10 mmol) was dissolved in ethyl acetate/methanol (2:1, v/v, 1.5 mL). Quinoline (0.04 mL) and Lindlar's catalyst (20 mg) were added. The suspension was de-gassed with hydrogen and rapidly stirred under an hydrogen atmosphere (1 atm) for overnight. The catalyst was filtered off with a small celite pad. The filtrate was concentrated and the residue was purified with preparative thin-layer chromatography on silica gel using 10% methanol/dichloromethane to yield Example 32 as an off-white solid (32 mg, 85%): $R_f$ 0.45 (10% methanol/dichloromethane); $^1$H NMR (300 MHz, DMSO-d$_6$) δ 11.78 (br s, 1H), 9.19 (s, 1H), 7.38 (d, J=7.2 Hz, 2H), 7.15-7.30 (m, 3H), 6.77 (d, J=12.5 Hz, 1H), 6.50 (br s, 1H), 6.36 (d, J=12.5 Hz, 1H), 5.74 (s, 1H), 3.35-3.50 (m, 4H), 2.65-2.80 (m, 4H), 2.56 (s, 3H), 2.13 (s, 3H); LRMS m/z 376, calcd 376 ($C_{21}H_{25}N_7$+H).

Example 33

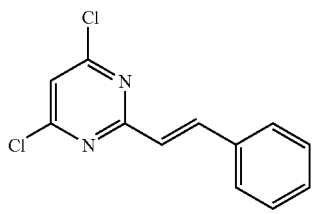

4,6-dichloro-2-[(E)-2-phenylvinyl]pyrimidine

To a rapidly stirred suspension of Rieke Mg (4.81 g, 200 mmol, 1.5 equiv) in tetrahydrofuran under nitrogen was added a tetrahydrofuran solution of β-bromostyrene (mixture of cis and trans, 29.00 g, 160 mmol, 1.2 equiv) dropwise in such a rate that the reaction temperature was maintained between 40-60° C. throughout the entire addition process. After the addition, the resulting deep-red solution was stirred at room temperature for 30 minutes and slowly added via a double-ended needle into a cooled (−20° C.) tetrahydrofuran solution of Example 27 (30.00 g, 132 mmol, 1 equiv) within 45 minutes. The reaction was stirred from −20° C. to room temperature for 4 hours, cooled to −20° C., and quenched with the dropwise addition of 1 N hydrochloric acid (200 mL). The mixture was concentrated at room temperature under reduced pressure and extracted with ethyl acetate (500 mL). The ethyl acetate layer was separated, washed with 1 N hydrochloric acid (200 mL×3), dried, and concentrated under reduced pressure. The crude product was purified with flash chromatography on silica gel with 0-2% ethyl acetate/hexane to yield Example 33 as a light-yellow solid (14.20 g, ~9:1 trans/cis, 43%): $R_f$ 0.60 (5% ethyl acetate/hexane); MS m/z 251, calcd 251 ($C_{12}H_8Cl_2N_2$+H).

Example 33 was also synthesized via Scheme 6 as indicated below.

Example 34

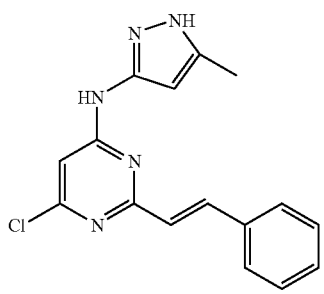

6-chloro-N-(3-methyl-1H-pyrazol-5-yl)-2-[(E)-2-phenylvinyl]pyrimidin-4-amine

Example 33 (14.20 g, 56.55 mmol, 1 equiv) was dissolved in anhydrous dimethylacetamide (100 mL). 5-Methyl-3-aminopyrazole (6.60 g, 68.00 mmol, 1.2 equiv), sodium iodide (12.70 g, 84.73 mmol, 1.5 equiv), and di-isopropylethylamine (14.76 mL, 84.73 mmol, 1.5 equiv) were added. The solution was stirred at 90° C. for 12 hours, cooled to room temperature, diluted with ethyl acetate (500 mL), washed with water (500 mL×1), saturated sodium bicarbonate (200 mL×3), and brine (100 mL×1), dried, and concentrated under reduced pressure. The resulting semi-solid was suspended in minimum dichloromethane (15 mL) with rapid swirling, and the fine precipitates were collected by filtration, washed with dichloromethane/hexane (1:1, v/v, 10 mL×4), and dried under high vacuum for overnight to yield Example 34 as an off-white solid (8.75 g, 50%, trans only): $R_f$ 0.75 (10% methanol/dichloromethane); $^1$H NMR (300 MHz, DMSO-$d_6$) δ 12.20 (s, 1H), 10.16 (s, 1H), 7.83 (d, J=12.0 Hz, 1H), 7.73 (d, J=5.1 Hz, 2H), 7.36-7.48 (m, 4H), 7.07 (d, J=12.0 Hz, 1H), 5.78 (s, 1H), 2.24 (s, 3H); MS m/z 312, calcd 312 ($C_{16}H_{14}ClN_5$+H).

Example 34 was also synthesized via Scheme 6 as indicated below.

Example 35

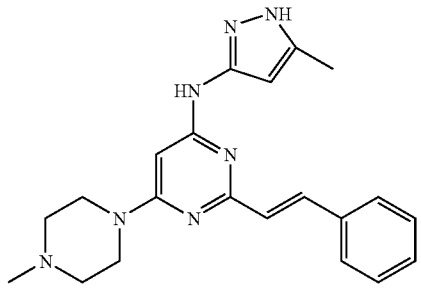

6-(4-methylpiperazin-1-yl)-N-(3-methyl-1H-pyrazol-5-yl)-2-[(E)-2-phenylvinyl]pyrimidin-4-amine Example 34 (7.79 g, 25.00 mmol, 1 equiv) was dissolved in 1,4-dioxane (15 mL). N-Methylpiperazine (4.16 mL, 37.50 mmol, 1.5 equiv), 4-dimethylaminopyridine (0.15 g, 1.25 mmol, 0.05 equiv), and di-isopropylethylamine (6.97 mL, 40.00 mmol, 1.6 equiv) were added. The solution was stirred at 100° C. for 48 hours, cooled to room temperature, and concentrated under reduced pressure. The residue was purified with flash chromatography on silica gel using 0-8% methanol/dichloromethane to give Example 31 as a light-yellow solid (3.56 g, 38%): Example 35 was also synthesized via Scheme 6 as indicated below. All analytical data were identical to those of Example 31 prepared by the alternate routes described.

Example 36

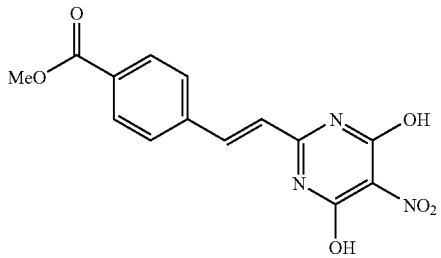

methyl 4-[(E)-2-(3,5-dihydroxy-4-nitrophenyl)vinyl]benzoate

To Example 1 (2 g, 11.69 mmol) was added 4-formylbenzoic acid methyl ester (7.69 g, 46.76 mmol) followed by piperidine (10 mL, 93.52 mmol). The reaction mixture was heated at 90° C. for 4 hours. The reaction mixture was then cooled to room temperature and methanol (10 mL) was added followed by diethyl ether (100 mL). The solid obtained was filtered and washed with 5% hydrochloric acid to afford Example 36 (2.0 g). $^1$H NMR (400 MHz, DMSO-$d_6$): δ 8.3 (br, 1H), 8.0-8.2 (m, 3H), 7.4 (d, 2H, J=8 Hz), 6.9 (d, 1H, J=16.4 Hz), 3.88 (s, 3H).

Example 36A

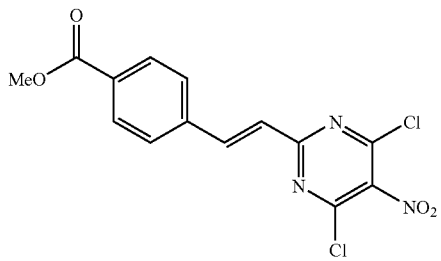

methyl 4-[(E)-2-(3,5-dichloro-4-nitrophenyl)vinyl]benzoate

Example 36 (6 g, 19.8 mmol) was treated with phosphorous oxychloride (21 mL, 229 mmol) followed by drop-wise addition of diethylaniline (9.5 mL, 59.6 mmol). The reaction mixture was heated to 80° C. overnight. The reaction mixture was then poured into crushed ice and the resulting solid collected and dried. The compound was then purified by column chromatography. 10% ethyl acetate:hexane was used as the eluent to give Example 36A (1.7 g). $^1$H NMR (400 MHz, CDCl3): δ 8.0-8.2 (m, 3H), 7.70 (m, 2H), 7.47 (d, 2H, J=8 Hz), 7.22 (d, 1H, J=16.4 Hz), 3.95 (s, 3H).

Example 37

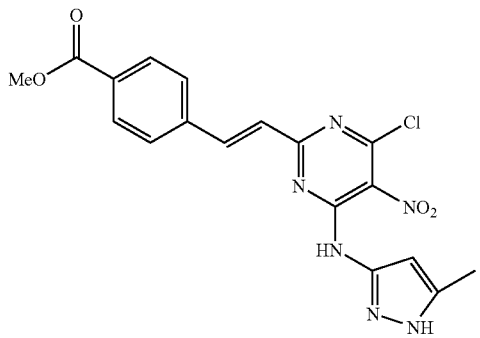

methyl 4-((E)-2-{4-chloro-6-[(3-methyl-1H-pyrazol-5-yl)amino]-5-nitropyrimidin-2-yl}vinyl)benzoate To a solution of Example 36A (1.55 g, 4.39 mmol) in tetrahydrofuran (30 mL) was added triethylamine (1.1 mL, 7.9 mmol) under nitrogen atmosphere at room temperature (30° C.). After 15 minutes, 5-amino-2-methyl-pyrazzole (426 mg, 4.39 mmol) in tetrahydrofuran (10 mL) was added drop-wise to the reaction mixture. After 5 hours the reaction mixture was evaporated to dryness. The solid obtained was triturated with ethyl acetate and hexane to obtain Example 37 (1.8 g). $^1$H NMR (400 MHz, DMSO-$d_6$): δ 12.1 (br, 1H), 9.75 (br, 1H), 8.08 (m, 3H), 7.69 (d, 1H, J=8.4 Hz), 7.13 (d, 1H, J=16 Hz), 6.66 (s, 1H), 3.94 (s, 3H), 2.17 (s, 3H). MS (m/z) 415 (M+1).

Example 38

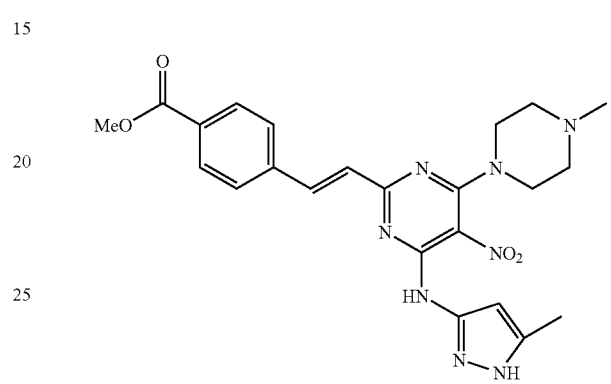

methyl 4-((E)-2-{4-(4-methylpiperazin-1-yl)-6-[(3-methyl-1H-pyrazol-5-yl)amino]-5-nitropyrimidin-2-yl} vinyl)benzoate To a solution of Example 37 (2.0 g, 4.83 mmol) in tetrahydrofuran (30 mL) was added triethylamine (1.0 mL, 7.3 mmol) under nitrogen atmosphere at room temperature (30° C.). After 15 min, N-methylpiperazine (483 mg, 4.83 mmol) in tetrahydrofuran (10 mL) was added drop-wise to the reaction mixture. After 0.5 hours, the reaction mixture was evaporated to dryness. The solid obtained was triturated with ethyl acetate and hexane to obtain Example 38 (2.2 g). A 500 mg of the crude compound was purified by preparative HPLC to give pure Example 38 (150 mg). $^1$H NMR (400 MHz, DMSO-$d_6$): δ 10.53 (br, 1H), 10.00 (br, 1H), 7.9-8.1 (m, 5H), 7.4 (m, 1H, J=16 Hz), 6.75 (s, 1H), 3.88 (s, 3H), 3.0-3.2 (m, 4H), 2.9 (m, 4H), 2.3 (s, 3H), 2.09 (s, 3H). MS (m/z) 479 (M+1)

Example 39

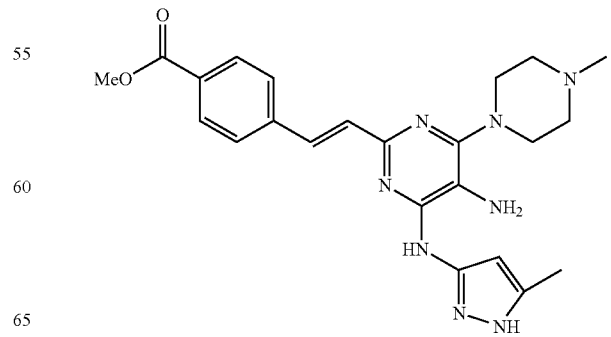

methyl 4-((E)-2-{5-amino-4-(4-methylpiperazin-1-yl)-6-[(3-methyl-1H-pyrazol-5-yl)amino]-pyrimidin-2-yl} vinyl)benzoate Tin (II) chloride dihydrate (1.0 g, 4.4 mmol) was dissolved in conc. hydrochloric acid (1 mL, 9.04 mmol). The reaction mixture was stirred for 10 minutes and was then cooled to <10° C. Example 38 (250 mg, 0.52 mmol) in methanol (20 mL) was added drop-wise to the reaction mixture. The cooling was removed and the reaction was stirred overnight. The reaction mixture was evaporated to ⅓$^{rd}$ volume then diluted with 40 mL of ethyl acetate. A solution of 1N NaOH (20 mL) was added to the reaction mixture. The organic layer was then separated, dried and evaporated under reduced pressure. The crude solid obtained was then purified by preparative HPLC to give 30 mg of Example 39. $^1$H NMR (400 MHz, DMSO-d$_6$) δ 9.89 (br, 1H), 8.93 (br, 1H), 7.96 (d, 2H, J=8 Hz), 7.77 (d, 2H, J=8 Hz), 7.57 (d, 1H, J=16 Hz), 7.24 (br, 1H), 7.17 (d, 1H, J=16 Hz), 7.11 (br, 1H), 6.99 (br, 1H), 6.58 (s, 1H), 3.88 (s, 3H), 3.1-3.8 (m, 8H), 2.88 (s, 3H), 2.31 (s, 3H). MS (m/z) 449 (M+1).

Example 31 Via Scheme 6

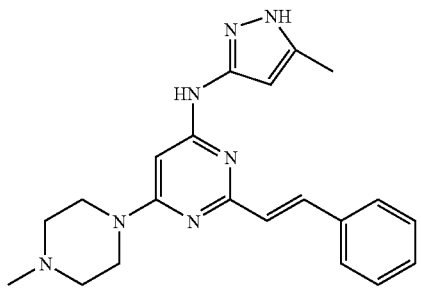

Synthesis of 6-(4-methylpiperazin-1-yl)-N-(3-methyl-1H-pyrazol-5-yl)-2-[(E)-2-phenylvinyl]pyrimidin-4-amine via Scheme 6

Following the general narrative described above for Scheme 6, commercially-available cinnamonitrile (70g) was dissolved in anhydrous toluene (1.19L) and absolute ethanol (287 ml, 0.91 mol, 9 eq). The clear solution obtained was cooled to −5° C. and dry HCl gas was gently bubbled for 2 hours after which the reaction was closed to seal and stirred for 15 hours at 0° C., workup of the reaction mixture provided O-ethyl imidate HCl salt (100 gm); $^1$HNMR (200 MHz, DMSO-D$_6$): 11.63 (2H, bs), 7.98 (1H, d, J=16.2 Hz), 7.73-7.32 (5H, m), 7.01 (1H, d, J=16.2 Hz), 4.46 (2H,q), 1.41 (3H, t, J=5.2 Hz). O-Ethyl imidate HCl salt (100 g) in ethanol (500 ml) was cooled to 0° C. and a methanol solution of dry ammonia (204 ml, 7N, 0.30 mol) was added. The mixture was stirred at room temperature for 12 hours. The mixture was worked up to provide intermediate-1 (80g, 89%); $^1$H-NMR (200 MHz, DMSO-D$_6$): 9.32 (2H, bs), 8.84 (2H, bs), 7.97 (1H, d, J=16.2 Hz), 7.62-7.44 (5H, m), 6.81 (1H, d, J=16.2 Hz); M+147 (100%, m/z).

Intermediate-1 (80 g) in methanol (80 ml) had dimethyl malonate (80 ml, 1.1 eq) added to it at room temperature. The mixture was cooled to 0° C. and NaOCH3 (44g, 4.4 eq) was added slowly over 10 minutes. The light yellow-white solution was heated to 90° C. and refluxed for 4 hours. Work up provided intermediate-2 (70g, 60%); $^1$H-NMR (200 MHz, DMSO-D$_6$): 11.62 (2H, bs), 7.87 (1H, d, J=16.2 Hz), 7.60-7.41 (5H, m), 6.85 (1H, d, J=16.2 Hz), 5.22 (1H, s); M+215 (100%, m/z).

Intermediate-2 (70g) was slowly added in portions to 600 ml of POCl$_3$. The mixture was stirred for 4-6 hrs at 100° C. The reaction mixture was concentrated under reduced pressure at 60° C. until dryness. Work up gave intermediate-3 (70 g, 85%); $^1$H-NMR (200 MHz, DMSO-D$_6$): 7.96 (1H, d, J=16.2 Hz), 7.80 (2H, m), 7.45-7.21 (5H, m); M+250.9, 252.9 (100%, m/z).

To a solution of intermediate-3 (70 g, 0.2278 mole) in anhydrous DMA (400 ml) was added 5-methyl-3aminopyrazole (32.50 g, 0.334 mol), NaI (62.33 g, 0.418 mole) and DIPEA (54 g, 1.48 mol) and the mixture was stirred at 90° C. for 12h. Work up and chromatographic purification gave compound-4 (50 g, 57%); $^1$H-NMR (200 MHz, DMSO-D$_6$): 12.12 (1H, s), 10.18 (1H, s), 7.83 (1H, d, J=16.2 Hz), 7.71 (3H, m), 7.45-7.33 (3H, m), 7.12 (1H, d, J=16.2 Hz), 6.22 (1H, bs), 2.21 (3H, s); M+312 (100%, m/z).

Intermediate-4 (50 g) was dissolved in N-methyl piperazine (150 ml) and heated at 110° C. for 1 hour. Work up and crystallization provided the target Example (25 g, 41.4%); $^1$H-NMR (200 MHz, DMSO-D$_6$): 11.92 (1H, s), 9.18 (1H, s), 7.76 (1H, d, J=16.2 Hz), 7.62 (2H, m), 7.41-7.35 (3H, m), 6.91 (1H, d, J=16.2 Hz), 6.61 (1H, bs), 6.01 (1H, bs), 3.57 (4H, m), 2.41 (4H, m), 2.22 (3H, s), 2.20 (3H, s); HPLC (98.1% pure, RT 24.36 min, Gradient, 0.1% TFA in Acetonitrile and 0.1% TFA in Water, Hypersil BDS C-18, 4.6×150 mm, 5.0 u).

Example 49

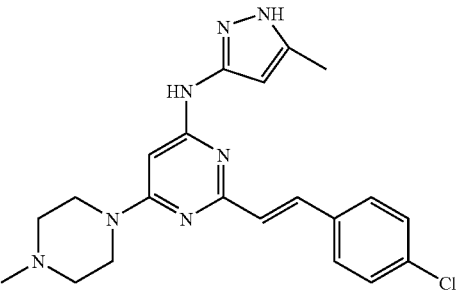

2-(4-chlorostyryl)-N-(5methyl-1H-pyrazol-3-yl)-6-(4-methylpiperazin-1-yl)pyrimidin-4-amine Example 49 was synthesized via Scheme 6 according to the general scheme provided above with the appropriate starting materials 3-(4-chlorophenyl)acrylonitrile, 5-methyl-1H- pyrazole-3-amine, and 1-methylpiperazine. Structure of the target was confirmed by ¹H-NMR. The 1H-NMR is attached.

Example 50

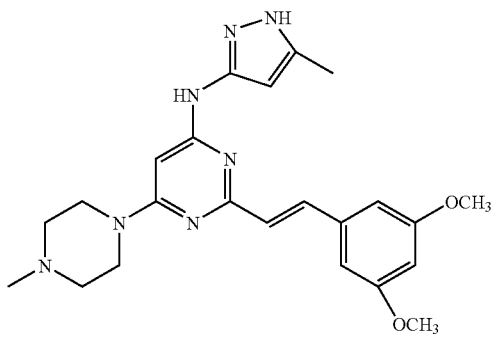

2-(3,5-dimethoxystyryl)-N-(5-methyl-1H-pyrazol-3-yl)-6-(4-methylpiperazin-1-yl)pyrimidin-4-amine Example 50 was synthesized via Scheme 6 according to the general scheme provided above with the appropriate starting materials 3-(3,5-dimethoxyphenyl)acrylonitrile, 5-methyl-1H-pyrazole-3-amine, and 1-methyl-piperazine. Structure of the target was confirmed by ¹H-NMR. The ¹H-NMR is attached.

Example 60

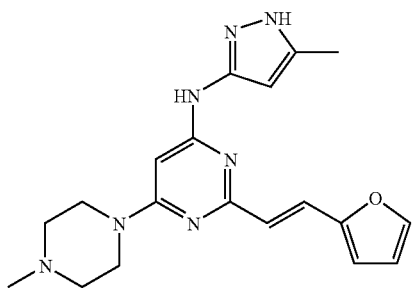

2-((E)-2-(furan-2-yl)vinyl)-N-(5-methyl-1H-pyrazol-3-yl)-6-(4-methylpiperazin-1-yl)pyrimidin-4-amine Example 60 was synthesized via Scheme 6 according to the general scheme provided above with the appropriate starting materials 3-(furan-2-yl)acrylonitrile, 5-methyl-1H-pyrazole- 3-amine, and 1-methylpiperazine. Structure of the target was confirmed by ¹H-NMR. The ¹H-NMR is attached.

Example 64

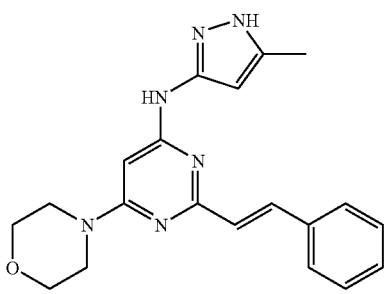

N-(5-methyl-1H-pyrazol-3-yl)-6-morpholino-2-styrylpyrimidin-4-amine

Example 64 was synthesized via Scheme 6 according to the general scheme provided above with the appropriate starting materials cinnamonitrile, 5-methyl-1H-pyrazole-3-amine, and morpholine. Structure of the target was confirmed by ¹H-NMR. The ¹H-NMR is attached.

Example 66

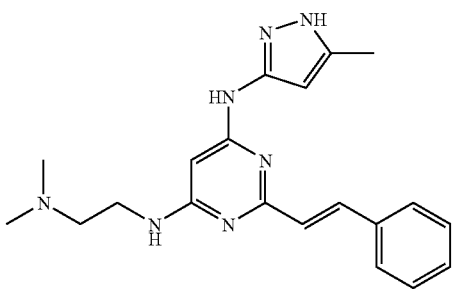

$N^4$-(2-(dimethylamino)ethyl)-$N^6$-(5-methyl-1H-pyrazol-3-yl)-2-styrylpyrimidine-4,6-diamine Example 66 was synthesized via Scheme 6 according to the general scheme provided above with the appropriate starting materials cinnamonitrile, 5-methyl-1H-pyrazol-3-amine, and N[1],N[1]-dimethylethane-1,2-diamine. Structure of the target was confirmed by $^1$H-NMR. The $^1$H-NMR is attached.

Example 67

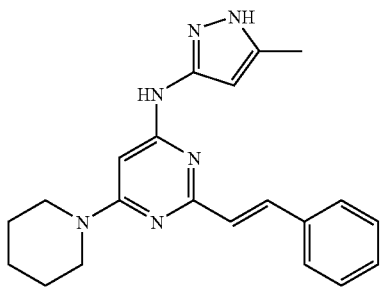

N-(5-methyl-1H-pyrazol-3-yl)-6-(piperidin-1-yl)-2-styrylpyrimidin-4-amine

Example 67 was synthesized via Scheme 6 according to the general scheme provided above with the appropriate starting materials cinnamonitrile, 5-methyl-1H-pyrazole-3-amine, and piperidine. Structure of the target was confirmed by $^1$H-NMR. The $^1$H-NMR is attached.

Example 69

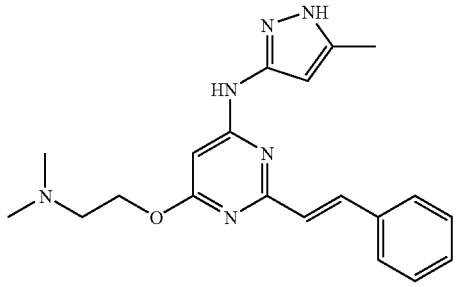

6-2-(dimethylamino)ethoxy)-N-(5-methyl-1H-pyrazol-3-yl)-2-styrylpyrimidin-4-amine Example 69 was synthesized via Scheme 6 according to the general scheme provided above with the appropriate starting materials cinnamonitrile, 5-methyl-1H-pyrazole-3-amine, and (2-dimethyl)aminoethanol. Structure of the target was confirmed by $^1$H-NMR. The $^1$H-NMR is attached.

Example 71

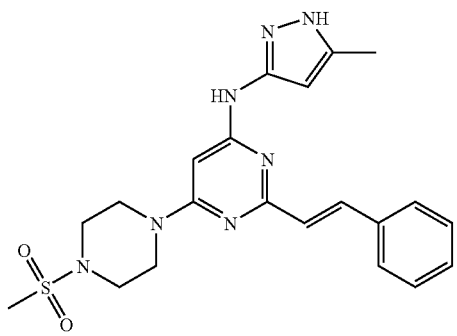

N-(5-methyl-1H-pyrazol-3-yl)-6-(4-methylsulfonylpiperazin-1-yl)-2-styrylpyrimidin-4-amine Example 71 was synthesized via Scheme 6 according to the general scheme provided above with the appropriate starting materials cinnamonitrile, 5-methyl-1H-pyrazole-3-amine, and 4-methylsulfonylpiperazine. Structure of the target was confirmed by $^1$H-NMR. The $^1$H-NMR is attached.

Example 76

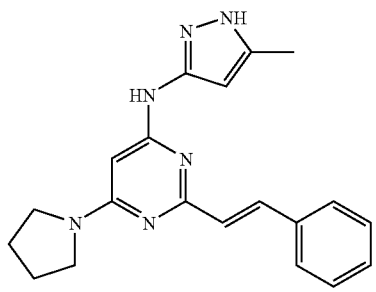

N-(5-methyl-1H-pyrazol-3-yl)-6-(pyrrolidin-1-yl)-2-styrylpyrimidin-4-amine

Example 76 was synthesized via Scheme 6 according to the general scheme provided above with the appropriate starting materials cinnamonitrile, 5-methyl-1H-pyrazole-3-amine, Example 77

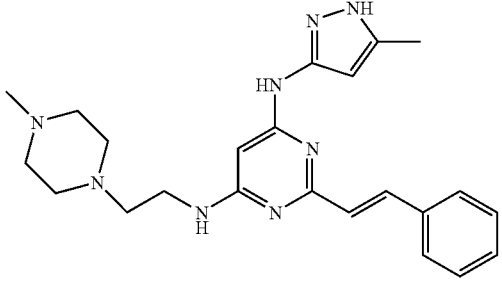

$N^4$-(5-methyl-1H-pyrazol-3-yl)-$N^6$-(2-(4-methylpiperazin-1-yl)ethyl)-2-styrylpyrimidine-4,6-diamine Example 77 was synthesized via Scheme 6 according to the general scheme provided above with the appropriate starting materials cinnamonitrile, 5-methyl-1H-pyrazole-3-amine, and 2-(4'-methylpiperazin-1'-yl)-aminoethane. Structure of the target was confirmed by $^1$H-NMR. The $^1$H-NMR is attached.

Example 82

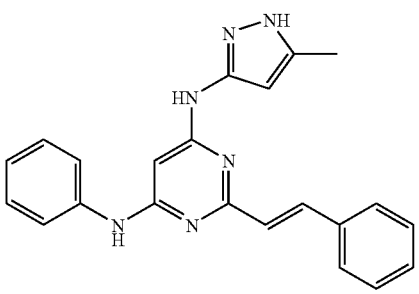

$N^4$-(5-methyl-1H-pyrazol-3-yl)-$N^6$-phenyl-2-styrylpyrimidine-4,6-diamine

Example 82 was synthesized via Scheme 6 according to the general scheme provided above with the appropriate starting materials cinnamonitrile, 5-methyl-1H-pyrazole-3-amine, and aniline. Structure of the target was confirmed by $^1$H-NMR. The $^1$H-NMR is attached.

Example 83

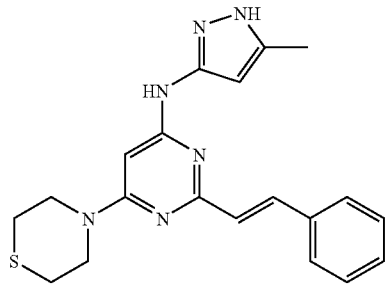

N-(5methyl-1H-pyrazol-3-yl)-2-styryl-6thiomorpholinopyrimidin-4-amine

Example 83 was synthesized via Scheme 6 according to the general scheme provided above with the appropriate starting materials cinnamonitrile, 5-methyl-1H-pyrazole-3-amine, and thiomorpholine. Structure of the target was confirmed by $^1$H-NMR. The $^1$H-NMR is attached.

Example 86

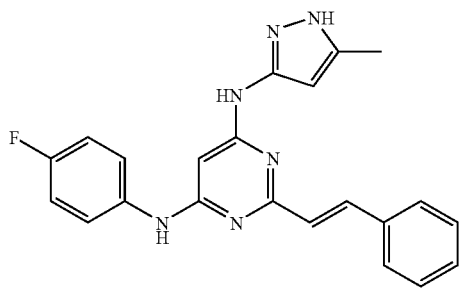

$N^4$-(4-fluorophenyl)-$N^6$-(5methyl-1H-pyrazol-3-yl)-2-styrylpyrimidine-4,6-diamine Example 86 was synthesized via Scheme 6 according to the general scheme provided above with the appropriate starting materials cinnamonitrile, 5-methyl-1H-pyrazole-3-amine, and 4-fluoroaniline. Structure of the target was confirmed by $^1$H-NMR. The $^1$H-NMR is attached.

Example 87

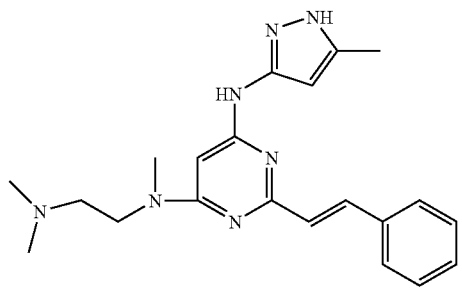

121

$N^4$-(2-(dimethylamino)ethyl)-$N^4$-methyl-$N^6$-(5-methyl-1H-pyrazol-3-yl)-2-styrylpyrimidine-4,6-diamine Example 87 was synthesized via Scheme 6 according to the general scheme provided above with the appropriate starting materials cinnamonitrile, 5-methyl-1H-pyrazole-3-amine, and $N^1,N^1,N^2$-trimethylethane-1,2-diamine. Structure of the target was confirmed by $^1$H-NMR. The $^1$H-NMR is attached.

Example 99

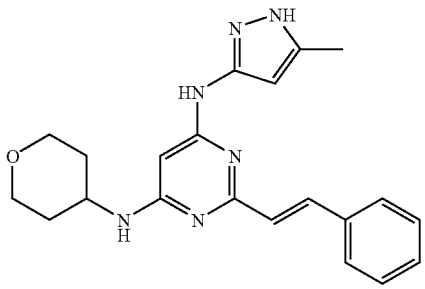

$N^4$-(tetrahydro-2H-pyran-4-yl)-$N^6$-(5-methyl-1H-pyrazol-3-yl)-2-styrylpyrimidine-4,6-diamine Example 99 was synthesized via Scheme 6 according to the general scheme provided above with the appropriate starting materials cinnamonitrile, 5-methyl-1H-pyrazole-3-amine, and tetrahydro-2H-pyran-4-amine. Structure of the target was confirmed by $^1$H-NMR. The $^1$H-NMR is attached.

Example 101

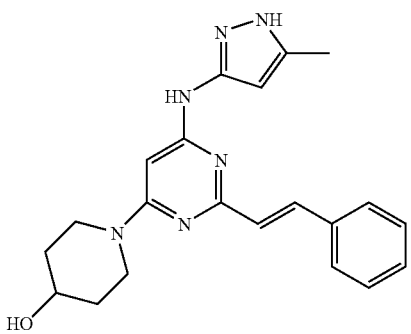

122

1-(6-(5-methyl-1H-pyrazol-3-ylamino)-2-styrylpyrimidin-4-yl)piperidin-4-ol

Example 101 was synthesized via Scheme 6 according to the general scheme provided above with the appropriate starting materials cinnamonitrile, 5-methyl-1H-pyrazole-3-amine, and O-protected piperidin-4-ol. Structure of the target was confirmed by $^1$H-NMR. The $^1$H-NMR is attached.

Example 103

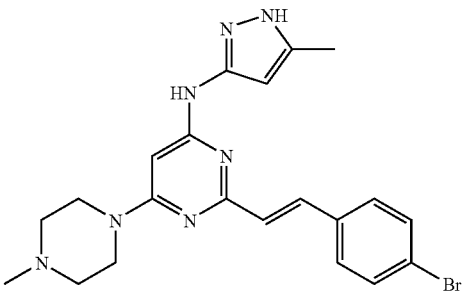

2-(4-bromostyryl)-N-(5-methyl-1H-pyrazol-3-yl)-6-(4-methylpiperazin-1-yl)pyrimidin-4-amine Example 103 was synthesized via Scheme 6 according to the general scheme provided above with the appropriate starting materials 3-(4-bromophenyl)-acrylonitrile, 5-methyl-1H-pyrazole-3-amine, and 4-methyl-piperizine. Structure of the target was confirmed by $^1$H-NMR. The $^1$H-NMR is attached.

Example 160

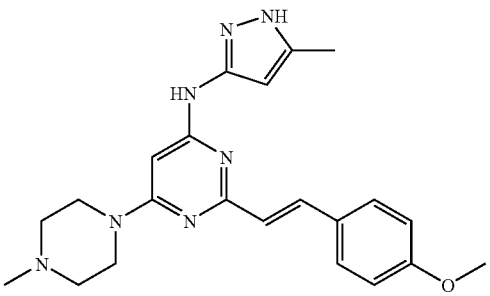

2-(4-methoxystyryl)-N-(5-methyl-1H-pyrazol-3-yl)-6-(4-methylpiperazin-1-yl)pyrimidin-4-amine Example 160 was synthesized via Scheme 6 according to the general scheme provided above with the appropriate starting materials 3-(4-methoxyphenyl)-acrylonitrile, 5-methyl-1H-pyrazole-3-amine, and 4-methyl-piperizine. Structure of the target was confirmed by $^1$H-NMR. The $^1$H-NMR is attached.

Example 161

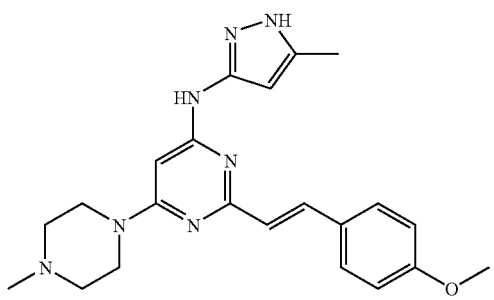

2-(4-methoxystyryl)-N-(5-methyl-1H-pyrazol-3-yl)-
6-(4-methylpiperazin-1-yl)pyrimidin-4-amine Example 161 was synthesized via Scheme 6 according to the general scheme provided above with the appropriate starting materials 3-(4-methoxyphenyl)-acrylonitrile, 5-methyl-1H-pyrazole-3-amine, and 4-methyl-piperizine. Structure of the target was confirmed by $^1$H-NMR. The $^1$H-NMR is attached.

Example 162

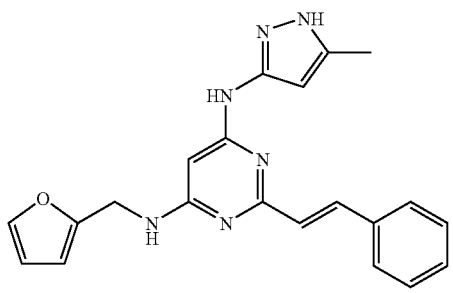

$N^4$-((furan-2-yl)methyl)-$N^6$-(5methyl-1H-pyrazol-3-yl)-2-styrylpyrimidine-4,6-diamine Example 162 was synthesized via Scheme 6 according to the general scheme provided above with the appropriate starting materials 3-(4-methoxyphenyl)acrylonitrile, 5-methyl-1H-pyrazole-3-amine, and (furan-2-yl)methanamine. Structure of the target was confirmed by $^1$H-NMR. The $^1$H-NMR is attached.

Example 163

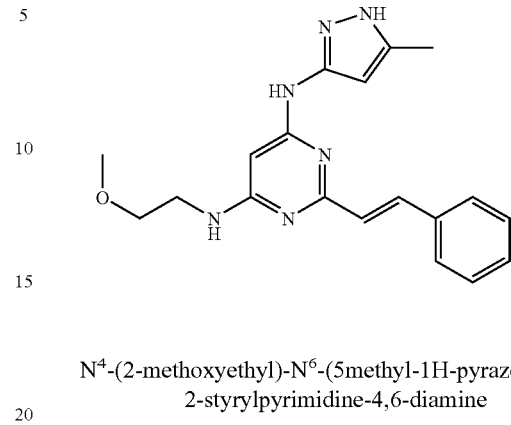

$N^4$-(2-methoxyethyl)-$N^6$-(5methyl-1H-pyrazol-3-yl)-
2-styrylpyrimidine-4,6-diamine Example 163 was synthesized via Scheme 6 according to the general scheme provided above with the appropriate starting materials cinnamonitrile, 5-methyl-1H-pyrazole-3-amine, and 2-methoxyethanamine. Structure of the target was confirmed by $^1$H-NMR. The $^1$H-NMR is attached.

Example 164

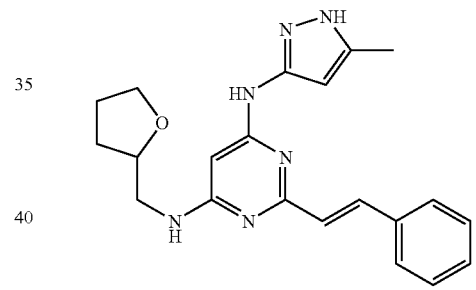

$N^4$-((tetrahydrofuran-2-yl)methyl)-$N^6$-(5-methyl-1H-pyrazol-3-yl)-2-styrylpyrimidine-4,6-diamine Example 164 was synthesized via Scheme 6 according to the general scheme provided above with the appropriate starting materials cinnamonitrile, 5-methyl-1H-pyrazole-3-amine, and (tetrahydrofuran-2-yl)methanamine. Structure of the target was confirmed by $^1$H-NMR. The $^1$H-NMR is attached.

Biological Testing

Biological Testing Example 1

Aurora A (Aurora 2) Inhibition Assay

Compounds were tested for their potency against recombinant Aurora A (Upstate, Lake Placid, N.Y.) using the PanVera Z'-Lyte kinase assay kit—Ser/Thr 1 peptide (Invitrogen, Carlsbad, Calif.). Assays were carried out in kinase assay buffer (50 mM HEPES, pH 7.5, 10 mM MgCl$_2$, 5 mM EGTA, 0.05% Brij-35, 2 mM DTT). Test compounds were initially dissolved in DMSO at 100× the highest tested concentration, then serially diluted to 4× test concentrations in kinase assay buffer. Next, Aurora A (final concentration 200-500 ng/mL), Z'-Lyte Ser/Thr 1 peptide (final concentration 2 μM) and ATP (final concentration 10 μM) were added according to the manufacturer's instructions. Assays were carried out in half-area 96-well white polystyrene assay plates (Corning, Corning, N.Y.) in a final volume of 20 μl. The reaction was allowed to proceed for 1 h at room temperature in the dark, at which point the development reagent and stop reagent were added according to the manufacturer's instructions. Coumarin (Ex. 400 nm, Em. 465 nm) and fluorescein (Ex. 400 nm, Em. 565 nm) fluorescence values were measured on a SpectraFluor Plus plate reader (Tecan, Durham, N.C.). The emission ratio (coumarin/fluorescein) was determined and used to calculate the percent phosphorylation for each well. Wells containing substrate but no kinase and wells containing a phosphopeptide control were used to set 0% and 100% phosphorylation values, respectively. Typically 20-40% of the substrate was phosphorylated in wells without inhibitor. Dose-response curves of relative Aurora A activity vs. inhibitor concentration were plotted with Grafit (Erithacus Software, Horley, Surrey, UK).

Table 2 shows representative data for the inhibition of Aurora A by the compounds of this invention at a concentration of 100 μM.

TABLE 2

| Example No. | % Inhibition of Aurora A @ 100 μM |
|---|---|
| 4 | 91 |
| 10 | 100 |
| 11 | 98 |
| 12 | 100 |
| 13 | 93 |
| 14 | 98 |
| 15 | 100 |
| 17 | 62 |
| 18 | 100 |
| 19 | 99 |
| 20 | 77 |
| 21 | 100 |
| 22 | 97 |
| 23 | 99 |
| 24 | 100 |
| 25 | 100 |
| 26 | 99 |
| 30 | 100 |
| 31 | 100 |
| 32 | 100 |
| 34 | 99 |
| 37 | 80 |
| 38 | 99 |
| 39 | 100 |
| 49 | 100 |
| 50 | 100 |
| 60 | 100 |
| 64 | 100 |
| 66 | 100 |
| 67 | 100 |
| 69 | 100 |
| 71 | 100 |
| 77 | 100 |
| 82 | 100 |
| 83 | 100 |
| 86 | 100 |
| 99 | 100 |
| 100 | 100 |
| 103 | 100 |
| 160 | 100 |
| 161 | 100 |

TABLE 2-continued

| Example No. | % Inhibition of Aurora A @ 100 μM |
|---|---|
| 162 | 100 |
| 163 | 100 |
| 164 | 100 |
| 169 | 95 |
| 170 | 100 |
| 171 | 89 |
| 172 | 99 |
| 173 | 100 |

Biological Testing Example 2

Aurora B (Aurora 1) Inhibition Assay

Assays for Aurora B kinase inhibition were carried out similarly to those for Aurora A kinase (see above) with the following modifications. Aurora B kinase (BPS Biosciences, San Diego, Calif.) was used as the enzyme, at a concentration was 2.5 μg/mL. The ATP concentration was 50 μM, and the kinase reaction was allowed to proceed for 16 h. Sodium orthovanadate (20 μM) was added to the buffer to inhibit contaminating phosphatases. Table 3 shows data for the inhibition of Aurora B by the compounds of this invention at a concentration of 100 μM.

TABLE 3

| Example No. | % Inhibition of Aurora B @ 100 μM |
|---|---|
| 10 | 97 |
| 18 | 100 |
| 26 | 95 |
| 30 | 97 |
| 31 | 100 |
| 32 | 99 |
| 60 | 99 |
| 100 | 100 |
| 163 | 100 |
| 164 | 100 |

Biological Testing Example 3

Ab1 Kinase Inhibition Assay

Compounds were assayed for Ab1 kinase inhibitory activity using N-terminal His$_6$-tagged recombinant human Ab1, residues 27-end (Upstate USA Inc, 706 Forest Street, Charlottesville, Va.). Serial dilutions of compound were assayed in a final reaction volume of 25 μL by incubating a solution of the above Ab1 kinase (5-10 mU), 8 mM MOPS (3-(N-morpholino) propanesulfonic acid) pH 7.0, 0.2 mM EDTA (ethylenediamine tetracetic acid), 50 μM of amino acid sequence EAIYAAPFAKKK (SEQ ID NO: 1) (Upstate USA Inc., Charlottesville, Va.), and 10 mM magnesium acetate and [γ-$^{33}$P-ATP] (specific activity of about 500 cpm/pmol, concentration as required). The reaction was initiated by the addition of the magnesium acetate and [γ-$^{33}$P-ATP] mixture. After incubation for 40 minutes at room temperature, the reaction was stopped by the addition of 5 μL of a 3% phosphoric acid solution. A 10 μL aliquote of the reaction was then spotted onto a P30 filtermat (PerkinElmer, Wellesley, Mass.) and washed three times for five minutes in 75 mM phosphoric acid and once in methanol prior to drying and scintillation counting. Inhibition of Ab1 activity was determined by comparison to assays that contained no inhibitor. Under these conditions, Example 31 produced about 77% inhibition of Ab1 at a concentration of 1 µM.

Biological Testing Example 4 cKit Kinase Inhibition Assay

Compounds were assayed for Src kinase inhibitory activity using N-terminal His-tagged human Src (Upstate USA mc, 706 Forest Street, Charlottesville, Va.). Serial dilutions of compound were assayed in a final reaction volume of 25 µL by incubating a solution of the above Src kinase (5-10 mU), 8 mM MOPS (3-(N-morpholino) propanesulfonic acid) pH 7.0, 0.2 mM EDTA (ethylenediamine tetracetic acid), 250 µM amino acid sequence KVEKIGEGTYGVVYK (SEQ ID NO: 2) (Upstate USA mc, 706 Forest Street, Charlottesville, Va.), and 10 mM magnesium acetate and [$\gamma$-$^{33}$P-ATP] (specific activity of about 500 cpmlpmol, concentration as required). The reaction was initiated by the addition of the magnesium acetate and [$\gamma$-$^{33}$P-ATP] mixture. After incubation for 40 minutes at room temperature, the reaction was stopped by the addition of 5 µL of a 3% phosphoric acid solution. A 10 µL aliquote of the reaction was then spotted onto a P30 filtermat (PerkinElmer, Wellesley, Mass.) and washed three times for five minutes in 75 mM phosphoric acid and once in methanol prior to drying and scintillation counting. Inhibition of Src activity was determined by comparison to assays that contained no inhibitor. Under these conditions, Example 31 produced about 95% inhibition of Src at a concentration of 1 µM.

Biological Testing Example 5

Src Kinase Inhibition Assay

Compounds were assayed for Src kinase inhibitory activity using N-terminal His-tagged human Src (Upstate USA Inc, 706 Forest Street, Charlottesville, Va.). Serial dilutions of compound were assayed in a final reaction volume of 25 µL by incubating a solution of the above Src kinase (5-10 mU), 8 mM MOPS (3-(N-morpholino) propanesulfonic acid) pH 7.0, 0.2 mM EDTA (ethylenediamine tetracetic acid), 250 µM amino acid sequence KVEKIGEGTYGVVYK (Upstate USA Inc, 706 Forest Street, Charlottesville, Va.), and 10 mM magnesium acetate and [$\gamma$-$^{33}$P-ATP] (specific activity of about 500 cpm/pmol, concentration as required). The reaction was initiated by the addition of the magnesium acetate and [$\gamma$-$^{33}$P-ATP] mixture. After incubation for 40 minutes at room temperature, the reaction was stopped by the addition of 5 µL of a 3% phosphoric acid solution. A 10 µL aliquote of the reaction was then spotted onto a P30 filtermat (PerkinElmer, Wellesley, Mass.) and washed three times for five minutes in 75 mM phosphoric acid and once in methanol prior to drying and scintillation counting. Inhibition of Src activity was determined by comparison to assays that contained no inhibitor. Under these conditions, Example 31 produced about 95% inhibition of Src at a concentration of 1 µM.

Biological Testing Example 6

Flt3 Kinase Inhibition Assay

Compounds were assayed for Flt3 kinase inhibitory activity using N-terminal GST-tagged recombinant human Flt3, residues 564-end (Upstate USA Inc, 706 Forest Street, Charlottesville, Va.). Serial dilutions of compound were assayed in a final reaction volume of 25 µL by incubating a solution of the above Flt3 kinase (5-10 mU), 8 mM MOPS (3-(N-morpholino) propanesulfonic acid) pH 7.0, 0.2 mM EDTA (ethylenediamine tetracetic acid), 50 µM amino acid sequence EAIYAAPFAKKK (SEQ ID NO: 1)(Upstate USA Inc, 706 Forest Street, Charlottesville, Va.), and 10 mM magnesium acetate and [$\gamma$-$^{33}$P-ATP] (specific activity of about 500 cpm/pmol, concentration as required). The reaction was initiated by the addition of the magnesium acetate and [$\gamma$-$^{33}$P-ATP] mixture. After incubation for 40 minutes at room temperature, the reaction was stopped by the addition of 5 µL of a 3% phosphoric acid solution. A 10 µL aliquote of the reaction was then spotted onto a P30 filtermat (PerkinElmer, Wellesley, Mass.) and washed three times for five minutes in 75 mM phosphoric acid and once in methanol prior to drying and scintillation counting. Inhibition of Flt3 activity was determined by comparison to assays that contained no inhibitor. Under these conditions, Example 31 produced about 96% inhibition of Flt3 at a concentration of 1 µM.

Biological Testing Example 7

KDR Kinase Inhibition Assay

Compounds were assayed for KDR kinase inhibitory activity using N-terminal His$_6$-tagged recombinant human KDR, residues 790-end (Upstate USA Inc, 706 Forest Street, Charlottesville, Va.). Serial dilutions of compound were assayed in a final reaction volume of 25 µL by incubating a solution of the above KDR kinase (5-10 mU), 8 mM MOPS (3-(N-morpholino) propanesulfonic acid) pH 7.0, 0.2 mM EDTA (ethylenediamine tetracetic acid), 0.33 mg/mL myelin basic protein (Upstate USA Inc, 706 Forest Street, Charlottesville, Virginia), and 10 mM magnesium acetate and [$\gamma$-$^{33}$P-ATP] (specific activity of about 500 cpm/pmol, concentration as required). The reaction was initiated by the addition of the magnesium acetate and [$\gamma$-$^{33}$P-ATP] mixture. After incubation for 40 minutes at room temperature, the reaction was stopped by the addition of 5 µL of a 3% phosphoric acid solution. A 10 µL aliquote of the reaction was then spotted onto a P30 filtermat (PerkinElmer, Wellesley, Mass.) and washed three times for five minutes in 75 mM phosphoric acid and once in methanol prior to drying and scintillation counting. Inhibition of KDR activity was determined by comparison to assays that contained no inhibitor. Under these conditions, Example 31 produced about 94% inhibition of KDR at a concentration of 1 µM.

Biological Testing Example 8

Lck Kinase Inhibition Assay

Compounds were assayed for Lck kinase inhibitory activity using recombinant, full-length human N-terminal His-tagged Lck, residues 790-end (Upstate USA Inc, 706 Forest Street, Charlottesville, Va.). Serial dilutions of compound were assayed in a final reaction volume of 25 µL by incubating a solution of the above Lck kinase (5-10 mU), 50 mM Tris- pH 7.0, 0.1 mM EGTA (ethylene glycol bis[2-aminoethyl ether]tetracetic acid), 0.1 mM Na$_3$VO$_4$, 0.1% β-mercaptoethanol, 0.1 mg/mL poly-glutamate-tyrosine 4:1, and 10 mM magnesium acetate and [$\gamma$-$^{33}$P-ATP] (specific activity of about 500 cpm/pmol, concentration as required). The reaction was initiated by the addition of the magnesium acetate and [$\gamma$-$^{33}$P-ATP] mixture. After incubation for 40 minutes at room temperature, the reaction was stopped by the addition of 5 µL of a 3% phosphoric acid solution. A 10 µL aliquote of the reaction was then spotted onto a Filtermat A and washed three times for five minutes in 75 mM phosphoric acid and once in methanol prior to drying and scintillation counting. Inhibition of Lck activity was determined by comparison to assays that contained no inhibitor. Under these conditions, Example 31 produced about 98% inhibition of Lck at a concentration of 1 µM.

Biological Testing Example 9

Kinase Selectivity Assay

Compounds were assayed for inhibitory activity against a panel of different kinase enzymes at a concentration of 1 µM. Where appropriate, full-length enzymes or catalytically active fragments, with N-terminal or C-terminal His- or GST-tags, were used (Invitrogen, Carlsbad, Calif.). Test compounds were initially diluted to 100× test concentration in 100% DMSO. This 100× concentration was then diluted to a 4× working concentration in Kinase Buffer (50 mM HEPES pH 7.5, 0.01% Brij-35, 10 mM $MgCl_2$, 1 mM EGTA) and 2.5 µL was then added to a low volume NBS, 384-well plate (Corning, Corning, N.Y.). Five µL of a 2× peptide/kinase mixture (Invitrogen, Carlsbad, Calif.), as appropriate (listed in Table 3), was then added and the reaction was then initiated by addition of 2.5 µL of a 4× working concentration of ATP in Kinase Buffer. Inhibition was determined at an ATP concentration equivalent to the apparent $K_m$ for each individual kinase, or at an ATP concentration of 100 µM if the apparent $K_m$ could not be reached. Table 4 shows the percent inhibition values obtained for Example 10 and Example 31 under these conditions.

TABLE 4

|  | Percent Inhibition at 1 µM (Example 10) | Percent Inhibition at 1 µM (Example 31) | Peptide Substrate |
|---|---|---|---|
| ABL1 | 54 | 81 | Tyr 2 |
| ABL1 E255K | 53 | 74 | Tyr 2 |
| ABL1 G250E | 60 | 85 | Tyr 2 |
| ABL1 T315I | 79 | 91 | Tyr 2 |
| ABL1 Y253F | 57 | 80 | Tyr 2 |
| ABL2 (Arg) | 32 | 74 | Tyr 2 |
| AKT1 (PKB alpha) | 9 | 5 | Ser/Thr 6 |
| AURKB (Aurora B) | 37 | 75 | Ser/Thr 1 |
| BLK | 67 | 90 | Tyr 1 |
| BMX | 19 | 61 | Tyr 1 |
| BTK | 28 | 63 | Tyr 1 |
| CDK2/cyclin A | 8 | 8 | Ser/Thr 12 |
| CSF1R (FMS) | 80 | 97 | Tyr 1 |
| DAPK3 (ZIPK) | 93 | 68 | Ser/Thr 13 |
| EPHA1 | 52 | 77 | Tyr 2 |
| EPHB1 | 32 | 61 | Tyr 1 |
| FGFR1 | 46 | 77 | Tyr 4 |
| FGFR2 | 53 | 86 | Tyr 4 |
| FLT1 (VEGFR1) | 25 | 53 | Tyr 4 |
| FLT3 | 93 | 98 | Tyr 2 |
| FLT3 D835Y | 80 | 98 | Tyr 2 |
| FLT4 (VEGFR3) | 87 | 97 | Tyr 4 |
| FYN | 50 | 89 | Tyr 2 |
| GSK3A (GSK3 alpha) | 38 | 36 | Ser/Thr 9 |
| GSK3B (GSK3 beta) | 26 | 28 | Ser/Thr 9 |
| IRAK4 | 14 | 63 | Ser/Thr 7 |
| JAK2 | 61 | 91 | Tyr 4 |
| KDR (VEGFR2) | 88 | 96 | Tyr 1 |
| KIT | 39 | 75 | Tyr 6 |
| KIT T670I | 44 | 79 | Tyr 6 |
| LCK | 81 | 94 | Tyr 2 |
| LYN A | 63 | 84 | Tyr 2 |
| MAP2K1 (MEK1) | 23 | 3 | Ser/Thr 3 |
| NTRK1 (TRKA) | 92 | 96 | Tyr 1 |
| PDGFRA (PDGFR alpha) | 58 | 83 | Tyr 4 |

TABLE 4-continued

|  | Percent Inhibition at 1 µM (Example 10) | Percent Inhibition at 1 µM (Example 31) | Peptide Substrate |
|---|---|---|---|
| PDGFRA D842V | 9 | 24 | Tyr 4 |
| PDGFRA T674I | 65 | 88 | Tyr 4 |
| PTK2 (FAK) | 81 | 94 | Tyr 1 |
| RET | 95 | 98 | Tyr 2 |
| ROS1 | 54 | 65 | Tyr 1 |
| SRC | 85 | 96 | Tyr 2 |
| STK6 (Aurora A) | 83 | 96 | Ser/Thr 1 |
| SYK | 88 | 86 | Tyr 2 |
| TBK1 | 73 | 80 | Ser/Thr 5 |
| YES1 | 80 | 88 | Tyr 2 |

Biological Testing Example 10

Whole Cell Cytotoxicity

Assay: Sulforhodamine B

Reference: Developmental Therapeutics Program NCI/NIH http://dtp.nci.nih.gov/branches/btb/ivclsp.html Human tumor-derived cell lines, HCT116 or MCF7 (ATCC) were plated in a 96 well plate in DMEM containing 10% fetal bovine serum and 2 mM L-glutamine at a density of 500 HCT116 cells or 1,000 MCF7 cells per well and incubated at 37° C., 5% $CO_2$, for 24 hours prior to the addition of experimental compounds. Compounds were added using the dilution series indicated to duplicate plates and the cells were incubated in media plus compound for 96 hours. An additional plate was fixed in 10% TCA at the time of the addition of compound to provide a measurement of the cell population at time zero, the time of drug addition. Following the 96 hour incubation, cells were fixed in situ by gently aspirating off the culture media and then adding 50 ul of ice cold 10% TCA per well and incubation at 4° C. for 60 minutes. The plates were washed with tap water five times and allowed to air dry for 5 minute. 50 ul of a 0.4% (w/v) Sulforhodamine B solution in 1% (v/v) acetic acid was added per well and the cells were incubated for 30 minutes at room temperature. Following staining, plates were washed four times with 1% acetic acid to remove any unbound dye and then allowed to air dry for 5 minutes. The stain was solubilized with 100 ul of 10 mM Tris pH 10.5 per well and placed on an orbital rotator for 5 minutes. The absorbance was read at 570 nm. Percentage growth was calculated using the absorbance readings from the time zero plate (Tz) and the dilution series plate (C) which included a column of cells grown in media without compound as a control (C) using the formulas:

[(Ti−Tz)/(C−Tz)]×100 for concentrations for which Ti>/=Tz

[(Ti−Tz)/Tz]×100 for concentrations for which Ti<Tz.

Three dose response parameters were calculated for each experimental agent. Growth inhibition of 50% (GI50) was calculated from [(Ti−Tz)/(C−Tz)]×100=50, which was the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from [(Ti−Tz)/Tz]×100=−50. Values are calculated for each of these three parameters if the level of activity was reached; however, if the effect was not reached or was exceeded, the value for that parameter is expressed as greater or less than the maximum or minimum concentration tested.

Table 5 shows representative values for the inhibition of HCT-116 cell growth by the compounds of this invention at a concentration of 100 μM.

TABLE 5

| Example No. | % Inhibition of HCT-116 cell growth @ 100 μM |
|---|---|
| 4 | 87 |
| 10 | 99 |
| 11 | 99 |
| 12 | 99 |
| 15 | 91 |
| 17 | 93 |
| 18 | 80 |
| 19 | 96 |
| 20 | 97 |
| 21 | 93 |
| 22 | 85 |
| 23 | 91 |
| 24 | 99 |
| 25 | 95 |
| 26 | 98 |

TABLE 5-continued

| Example No. | % Inhibition of HCT-116 cell growth @ 100 μM |
|---|---|
| 30 | 99 |
| 31 | 99 |
| 32 | 87 |
| 34 | 98 |
| 39 | 97 |
| 49 | 75 |
| 50 | 98 |
| 60 | 98 |
| 64 | 98 |
| 66 | 98 |
| 67 | 98 |
| 69 | 99 |
| 71 | 98 |
| 77 | 99 |
| 82 | 98 |
| 83 | 98 |
| 86 | 98 |
| 99 | 98 |
| 100 | 96 |
| 103 | 84 |
| 160 | 97 |
| 161 | 93 |
| 162 | 98 |
| 163 | 98 |
| 164 | 96 |
| 170 | 99 |
| 172 | 99 |
| 173 | 98 |

What is claimed is:

1. A compound of formula I:

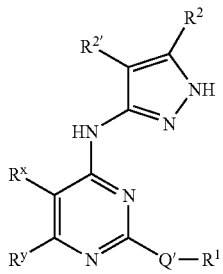

Formula I or a pharmaceutically acceptable salt or prodrug thereof, wherein:

$R^x$ is -T-$R^3$ or -L-Z-$R^3$;

$R^y$ is -T'-$R^{3'}$ or -L'-Z-$R^{3'}$, wherein $R^{3'}$ is —R', -halo, —OR', —C(=O)R', —$CO_2$R', —COCOR', —$COCH_2$COR', —$NO_2$, —CN, —S(O)R', —$S(O)_2$R', —SR', —N($R^4$)$_2$, —CON($R^7$)$_2$, —$SO_2$N($R^7$)$_2$, —OC(=O)R', —N($R^7$)COR', —N($R^7$)$CO_2$($C_{1-6}$ aliphatic), —N($R^4$)N($R^4$)$_2$, —C=NN($R^4$)$_2$, —C=N—OR', —N($R^7$)CON($R^7$)$_2$, —N($R^7$)$SO_2$N($R^7$)$_2$, —N($R^4$)$SO_2$R', or —OC(=O)N(R')$_2$;

T' is a valence bond or —(C($R^6$)$_2$)-A'-; A' is a valence bond or a $C_1$-$C_3$ alkylidene chain wherein a methylene unit of said $C_{1-3}$ alkylidene chain is optionally replaced by —O—, —S—, —N($R^4$)—, —CO—, —CONH—, —NHCO—, —$SO_2$—, —$SO_2$NH—, —$NHSO_2$—, —$CO_2$—, —OC(O)—, —OC(O)NH—, or —$NHCO_2$—;

L' is —O—, —S—, —SO—, —$SO_2$—, —N($R^{6a}$)$SO_2$—, —$SO_2$N($R^{6a}$)—, —CO—, —$CO_2$—, —N($R^{6a}$)CO—, —N($R^{6a}$)C(O)O—, —N($R^{6a}$)CON($R^{6a}$)—, —N($R^{6a}$)$SO_2$N($R^{6a}$)—, —N($R^{6a}$)N($R^{6a}$)—, —C(O)N($R^{6a}$)—, —OC(O)N($R^{6a}$)—, —C($R^{6a}$)$_2$O—, —C($R^{6a}$)$_2$—, —C($R^{6a}$)$_2$SO—, —C($R^{6a}$)$_2$$SO_2$—, —C($R^{6a}$)$_2$$SO_2$N($R^{6a}$)—, —C($R^{6a}$)$_2$N($R^{6a}$)—, —C($R^{6a}$)$_2$N($R^{6a}$)C(O)—, —C($R^{6a}$)$_2$N($R^{6a}$)C(O)O—, —C($R^{6a}$)=NN($R^{6a}$)—, —C($R^{6a}$)=N—O—, —C($R^{6a}$)$_2$N($R^{6a}$)N($R^{6a}$)—, —C($R^{6a}$)$_2$N($R^{6a}$)$SO_2$N($R^{6a}$)—, or —C($R^{6a}$)$_2$N($R^{6a}$)CON($R^{6a}$)—;

each $R^{6a}$ is independently hydrogen or an optionally substituted $C_{1-4}$ aliphatic group, or two $R^{6a}$ groups on the same nitrogen atom may be taken together with the nitrogen atom to form a 3-6 membered heterocyclyl or heteroaryl ring;

each $R^{4'}$ is independently —$R^{7'}$, —$COR^{7'}$, —$CO_2$(optionally substituted $C_{1-6}$ aliphatic), —CON($R^{7'}$)$_2$, or —$SO_2$$R^{7'}$;

each $R^{7'}$ is independently hydrogen or an optionally substituted $C_{1-6}$ aliphatic group, or two $R^{7'}$ on the same nitrogen are taken together with the nitrogen to form a 5-8 membered heterocyclyl or heteroaryl ring; and each R' is independently hydrogen, optionally substituted $C_{1-6}$ aliphatic, optionally substituted $C_{6-10}$ aryl, an optionally substituted heteroaryl ring having 5-10 ring atoms, or a an optionally substituted heterocyclyl ring having 5-10 ring atoms;

Q' is —$CR^{6''}$=$CR^{6''}$— or —=—, wherein said —$CR^{6''}$=$CR^{6''}$— may be a cis or trans double bond or a mixture thereof;

$R^1$ is -T-(Ring D);

Ring D is a 5-7 membered monocyclic ring or 8-10 membered bicyclic aryl or carbocyclyl ring wherein each substitutable ring carbon of Ring D is independently substituted by oxo, -T-$R^5$, or -V-Z-$R^5$;

T is a valence bond or —(C($R^6$)$_2$)-A-;

A is a valence bond or a $C_1$-$C_3$ alkylidene chain wherein a methylene unit of said $C_{1-3}$ alkylidene chain is optionally replaced by —O—, —S—, —N($R^4$)—, —CO—, —CONH—, —NHCO—, —$SO_2$—, —$SO_2$NH—, —$NHSO_2$—, —$CO_2$—, —OC(O)—, —OC(O)NH—, or —$NHCO_2$—;

Z is a $C_{1-4}$ alkylidene chain;

L is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

$R^2$ and $R^{2'}$ are independently —R or -T-W-$R^6$, or $R^2$ and $R^{2'}$ taken together with their intervening atoms form a fused, 5-8 membered, unsaturated or partially unsaturated ring wherein each substitutable ring carbon of said fused ring formed by $R^2$ and $R^{2'}$ is independently substituted by halo, oxo, —CN, —$NO_2$, $R^7$, or -V-$R^6$;

$R^3$ is —R, -halo, —OR, —C(=O)R, —$CO_2$R, —COCOR, —$COCH_2$COR, —$NO_2$, —CN, —S(O)R, —$S(O)_2$R, —SR, —N($R^4$)$_2$, —CON($R^7$)$_2$, —$SO_2$N($R^7$)$_2$, —OC(=O)R, —N($R^7$)COR, —N($R^7$)$CO_2$($C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, or —OC(=O)N(R)$_2$;

each R is independently hydrogen, optionally substituted $C_{1-6}$ aliphatic, or optionally substituted $C_{6-10}$ aryl;

each $R^4$ is independently —$R^7$, —$COR^7$, —$CO_2$(optionally substituted $C_{1-6}$ aliphatic), —CON($R^7$)$_2$, or —$SO_2R^7$;

each $R^5$ is independently —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$), —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$) CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$ N($R^6$)$SO_2$N($R^6$)—, —C($R^6$)$_2$N($R^6$)CON($R^6$)—, or —CON($R^6$)—;

each $R^6$ is independently hydrogen or an optionally substituted $C_{1-4}$ aliphatic group;

each $R^{6'}$ is independently hydrogen or a $C_{1-4}$ aliphatic group, or two $R^{6'}$ on the same carbon atom are taken together to form a 3-8 membered carbocyclic ring;

each $R^{6''}$ is independently hydrogen, a $C_{1-4}$ aliphatic group, halogen, or optionally substituted aryl, or two $R^{6''}$ on adjacent carbon atoms are taken together to form a 5-7 membered carbocyclic ring; and each $R^7$ is independently hydrogen or an optionally substituted $C_{1-6}$ aliphatic group.

2. A compound of the formula:

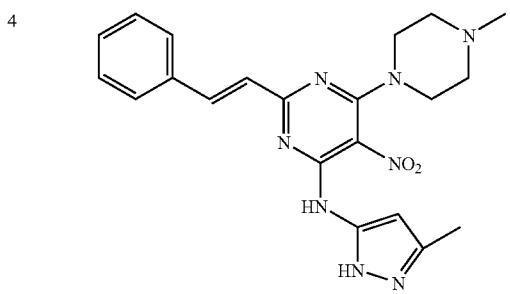

-continued
| Example No. | Structure |
|---|---|
| 11 | 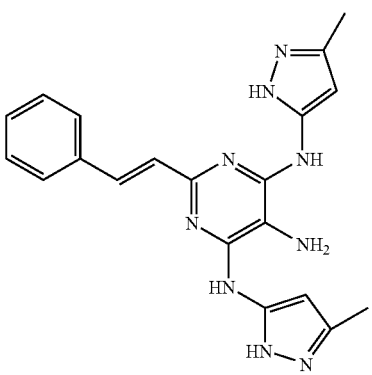 |
| 12 | 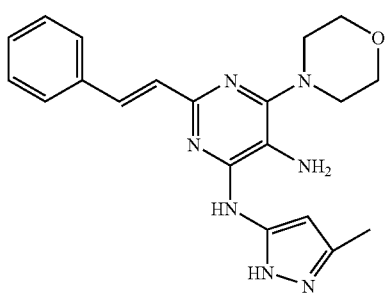 |
| 13 | 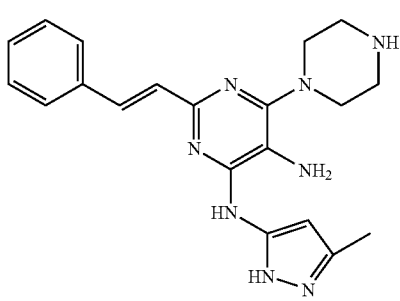 |
| 14 | 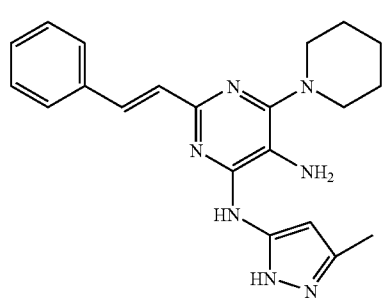 |
-continued
| Example No. | Structure |
|---|---|
| 15 | 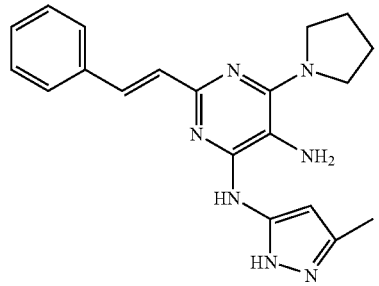 |
| 17 | 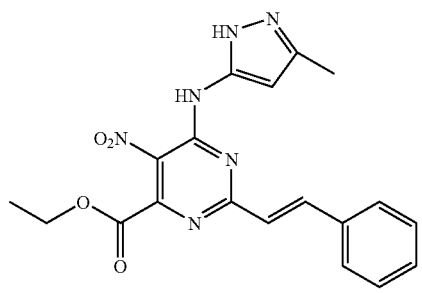 |
| 18 | 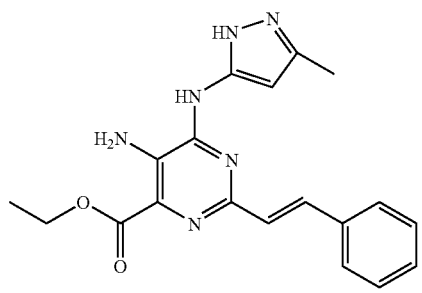 |
| 19 | 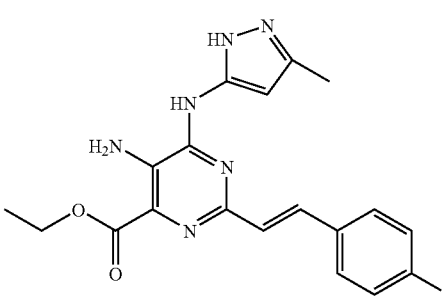 |
| 20 | 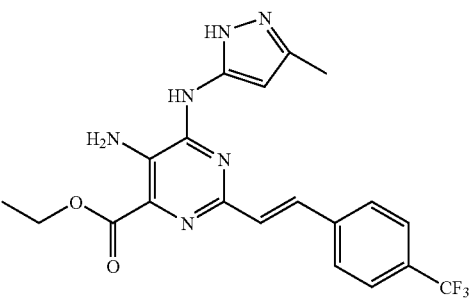 |

-continued
| Example No. | Structure |
|---|---|
| 21 | 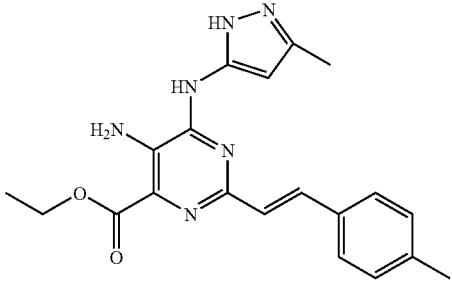 |
| 22 | 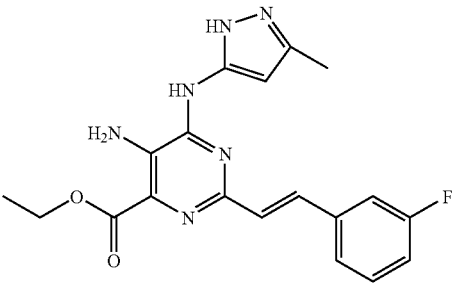 |
| 23 | 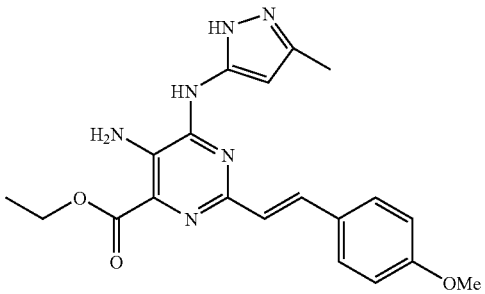 |
| 24 | 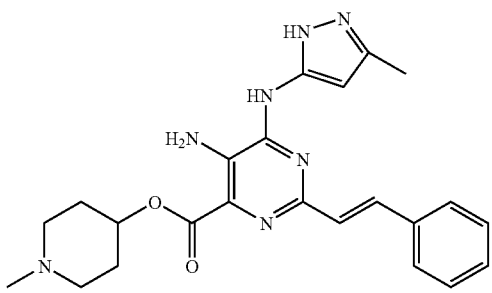 |
| 25 | 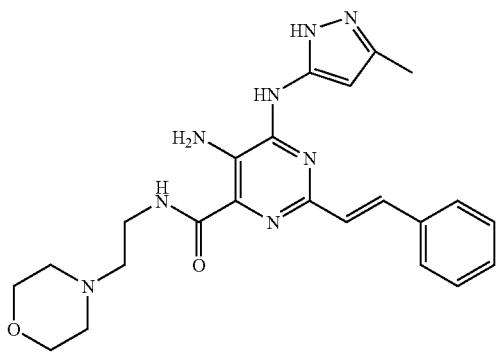 |
-continued
| Example No. | Structure |
|---|---|
| 26 | 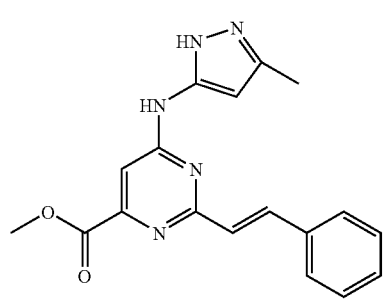 |
| 29 | 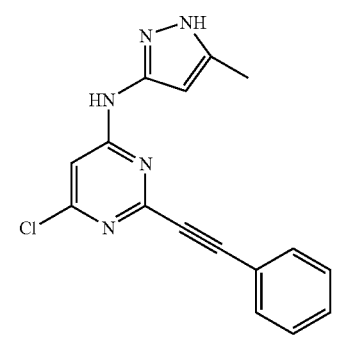 |
| 30 | 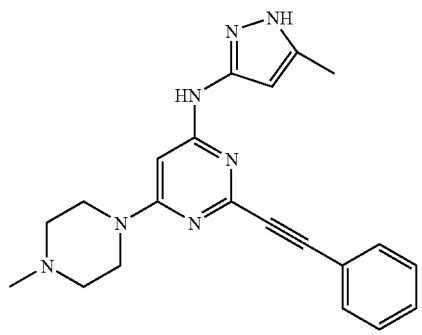 |
| 31 | 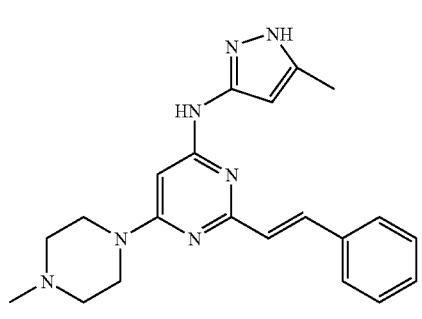 |

-continued
| Example No. | Structure |
|---|---|
| 32 | 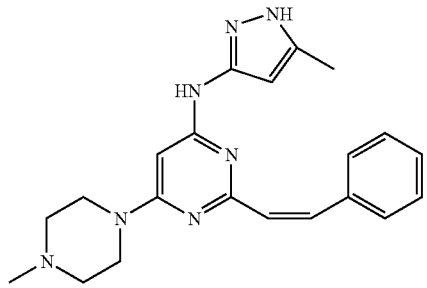 |
| 34 | 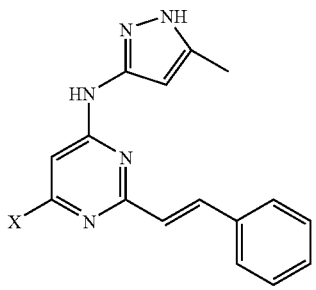
X = Cl, Br, I |
| 37 | 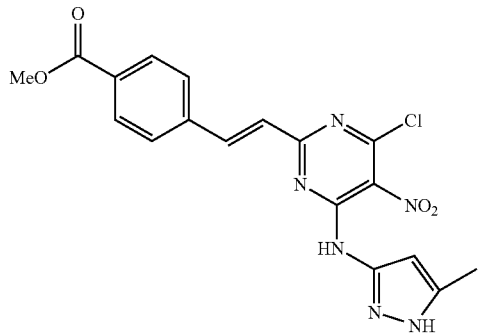 |
| 38 | 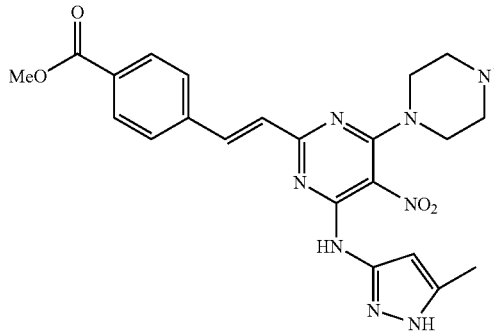 |
-continued
| Example No. | Structure |
|---|---|
| 39 | 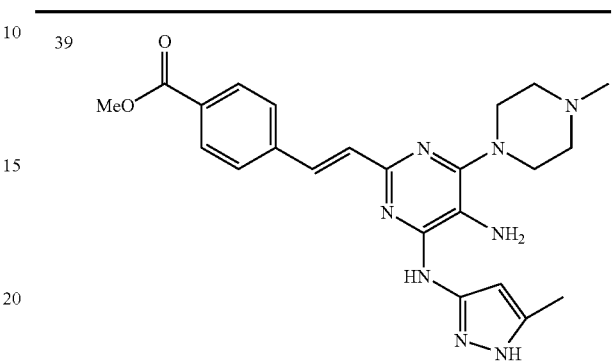 |
| 40 | 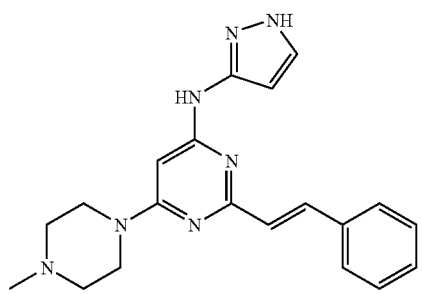 |
| 41 | 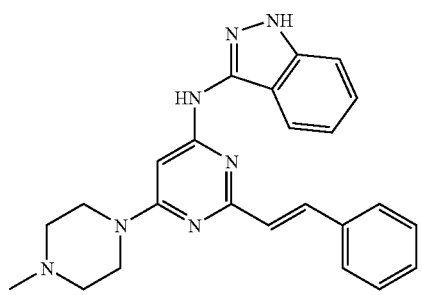 |
| 44 | 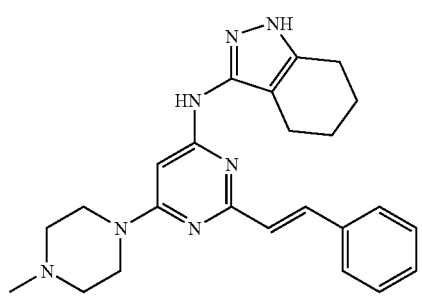 |

| Example No. | Structure |
|---|---|
| 46 | 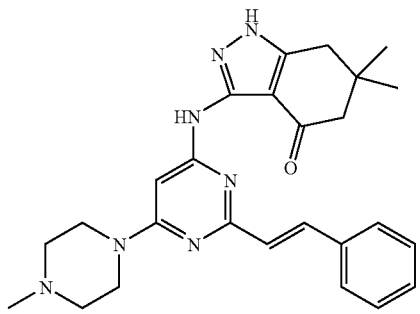 |
| 49 | 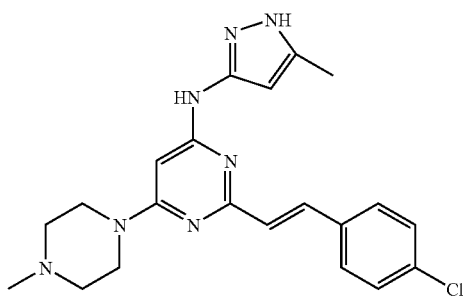 |
| 50 | 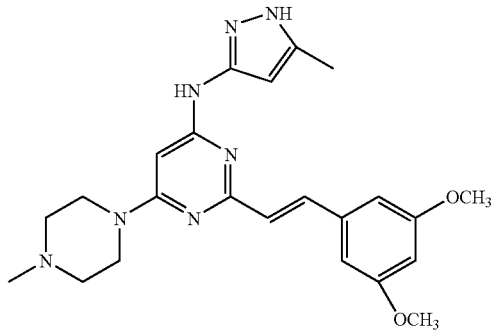 |
| 52 | 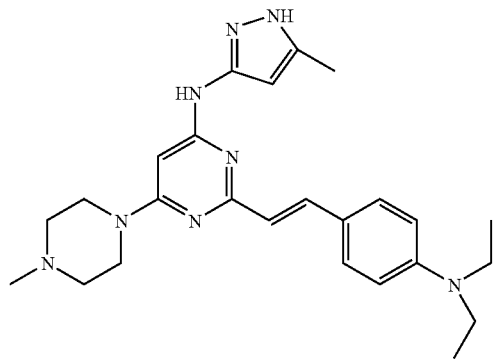 |
| Example No. | Structure |
|---|---|
| 53 | 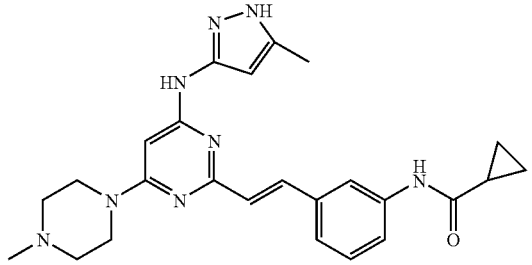 |
| 55 | 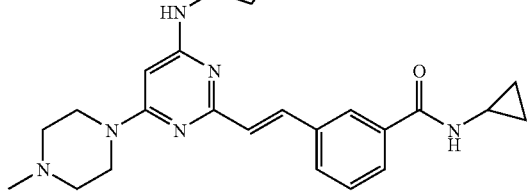 |
| 56 | 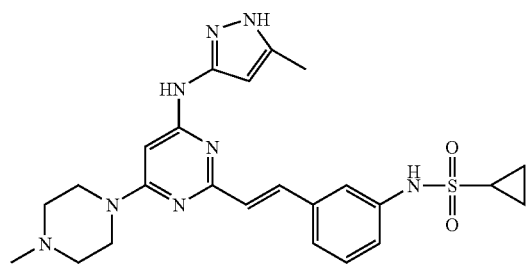 |
| 58 | 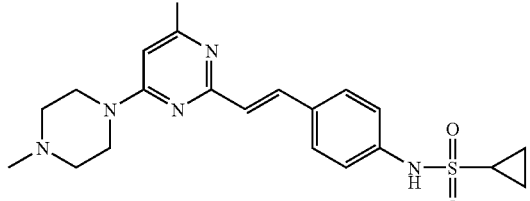 |
| 59 | 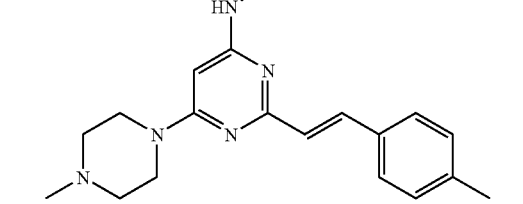 |

| Example No. | Structure |
|---|---|
| 62 | 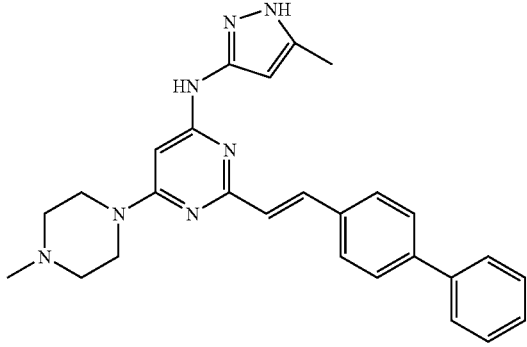 |
| 63 | 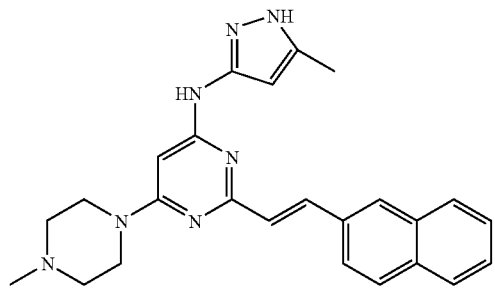 |
| 64 | 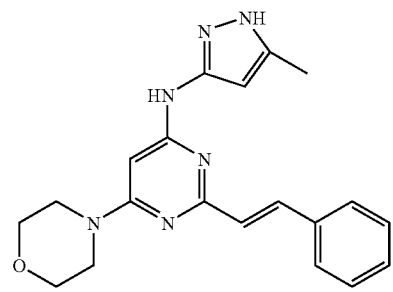 |
| 65 | 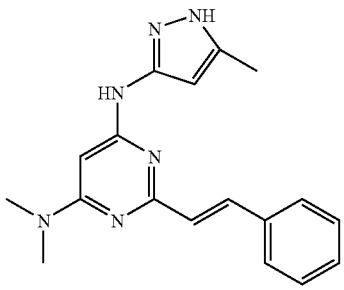 |
| 66 | 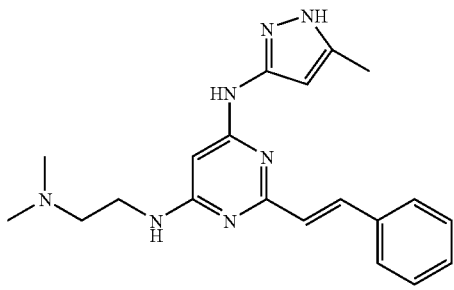 |
| 67 | 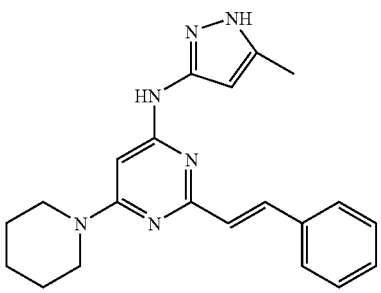 |
| 68 | 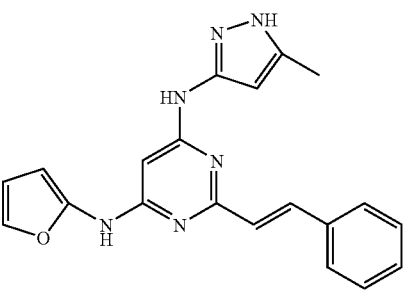 |
| 69 | 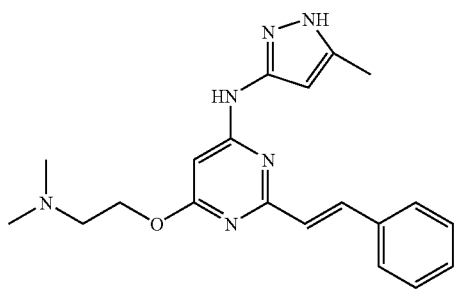 |
| 70 | 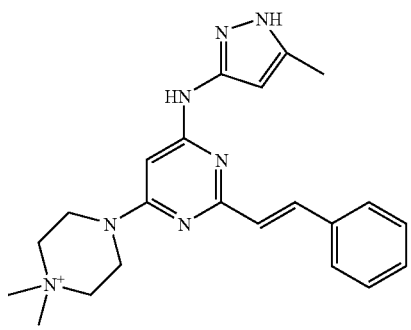 |

-continued
| Example No. | Structure |
|---|---|
| 71 | 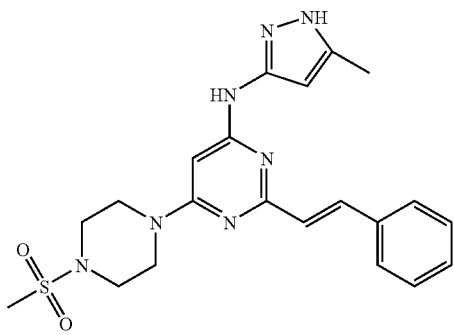 |
| 72 | 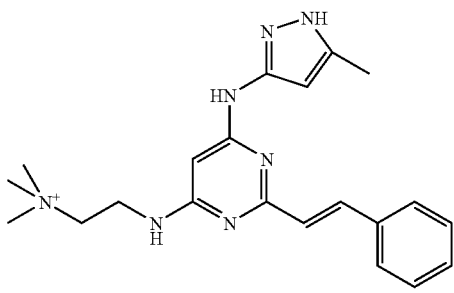 |
| 73 | 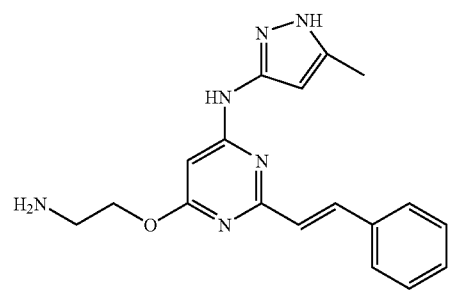 |
| 74 | 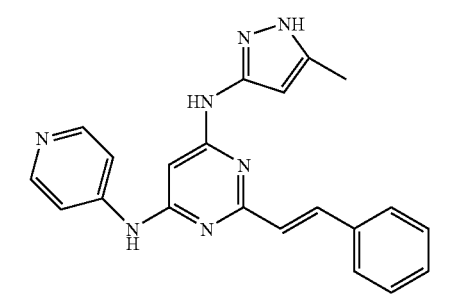 |
| 75 | 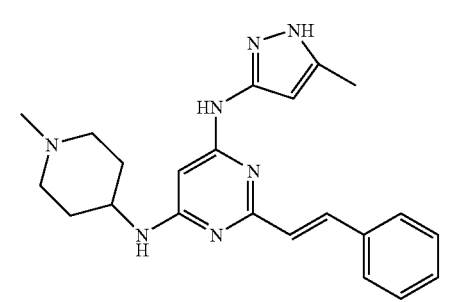 |
-continued
| Example No. | Structure |
|---|---|
| 76 | 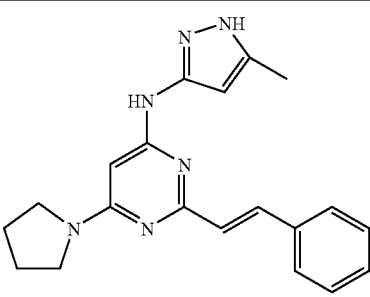 |
| 77 | 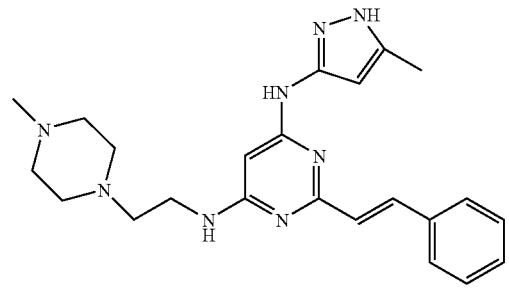 |
| 78 | 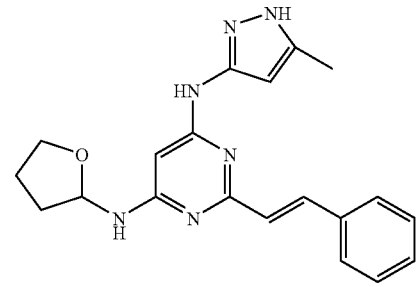 |
| 79 | 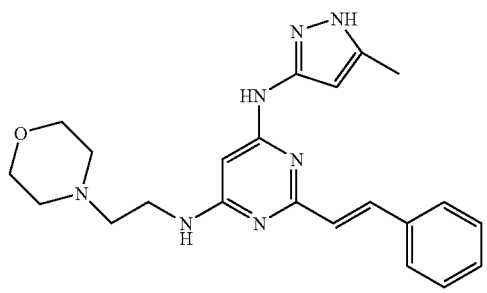 |
| 80 | 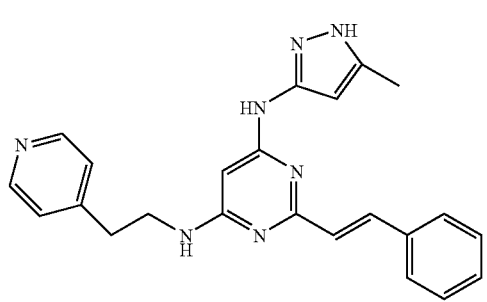 |

149
-continued
| Example No. | Structure |
|---|---|
| 81 | 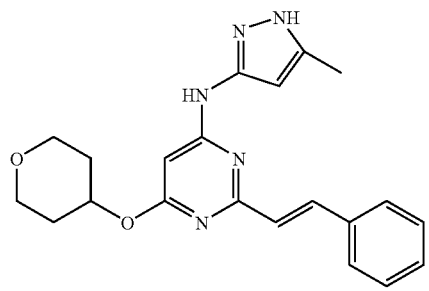 |
| 82 | 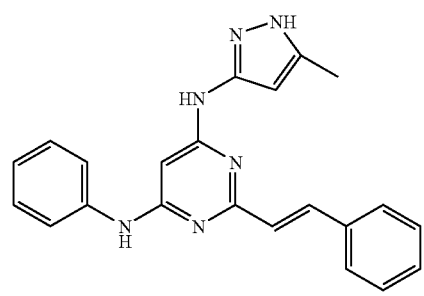 |
| 83 | 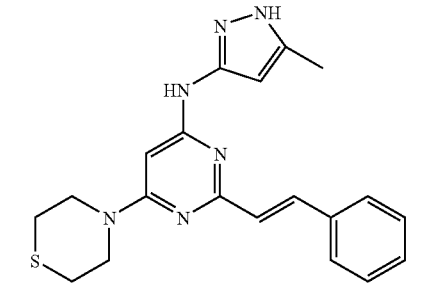 |
| 84 | 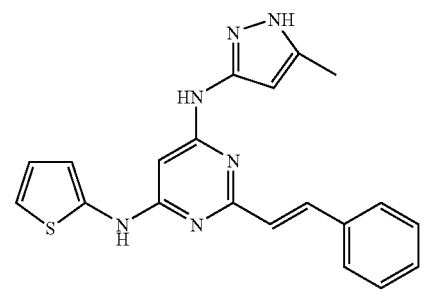 |
| 85 | 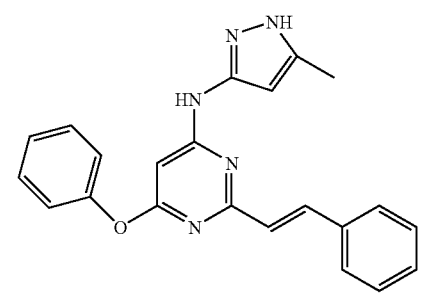 |
150
-continued
| Example No. | Structure |
|---|---|
| 86 | 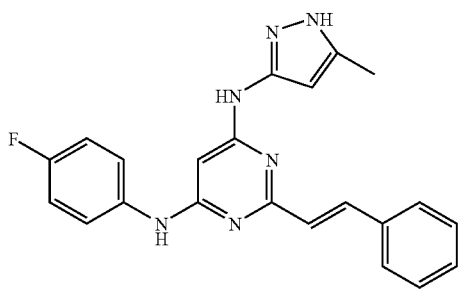 |
| 87 | 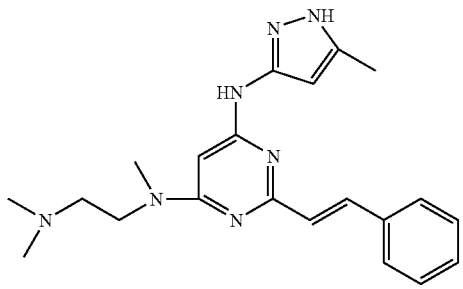 |
| 88 | 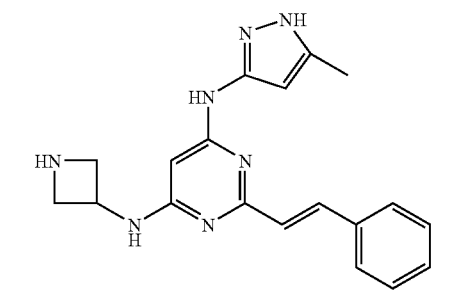 |
| 89 | 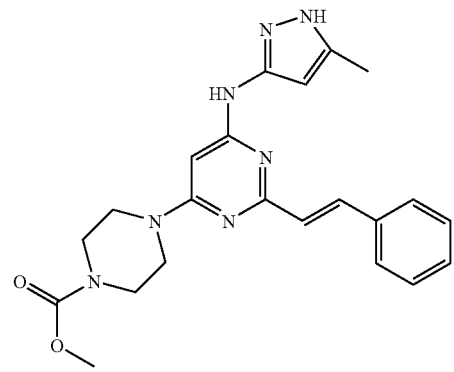 |

-continued

| Example No. | Structure |
|---|---|
| 90 | (chemical structure: 6-(4-acetylpiperazin-1-yl)-N-(5-methyl-1H-pyrazol-3-yl)-2-styrylpyrimidin-4-amine) |
| 91 | (chemical structure: 6-(3-aminoazetidin-1-yl)-N-(5-methyl-1H-pyrazol-3-yl)-2-styrylpyrimidin-4-amine) |
| 92 | (chemical structure: N-(5-methyl-1H-pyrazol-3-yl)-6-(morpholin-2-yl)-2-styrylpyrimidin-4-amine) |
| 93 | (chemical structure: N-(5-methyl-1H-pyrazol-3-yl)-6-(morpholin-3-yl)-2-styrylpyrimidin-4-amine) |

-continued

| Example No. | Structure |
|---|---|
| 94 | (chemical structure: 6-ethyl-N-(5-methyl-1H-pyrazol-3-yl)-2-styrylpyrimidin-4-amine) |
| 95 | (chemical structure: 6-ethoxy-N-(5-methyl-1H-pyrazol-3-yl)-2-styrylpyrimidin-4-amine) |
| 96 | (chemical structure: N-(5-methyl-1H-pyrazol-3-yl)-6-phenyl-2-styrylpyrimidin-4-amine) |
| 97 | (chemical structure: 6-(methoxymethoxy)-N-(5-methyl-1H-pyrazol-3-yl)-2-styrylpyrimidin-4-amine) |
| 98 | (chemical structure: 2-(4-fluorostyryl)-6-(4-methylpiperazin-1-yl)-N-(5-methyl-1H-pyrazol-3-yl)pyrimidin-4-amine) |

-continued
| Example No. | Structure |
|---|---|
| 99 | 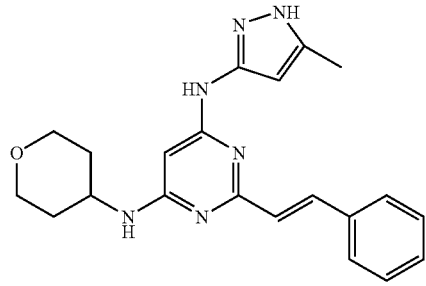 |
| 100 | 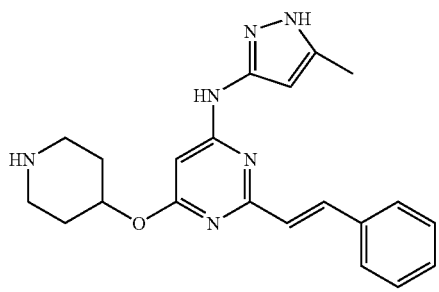 |
| 101 | 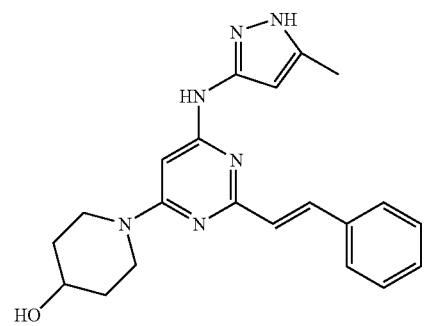 |
| 102 | 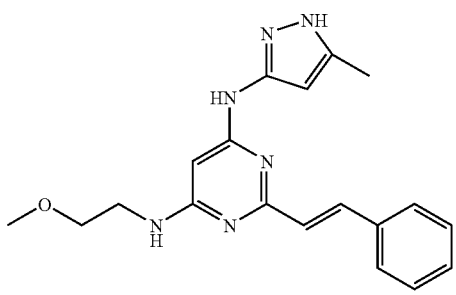 |
| 103 | 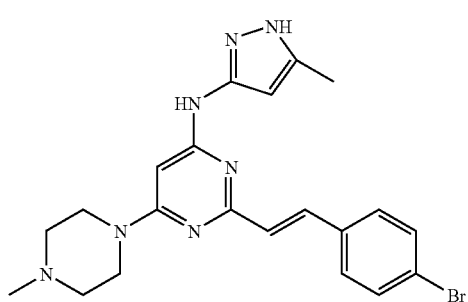 |
-continued
| Example No. | Structure |
|---|---|
| 104 | 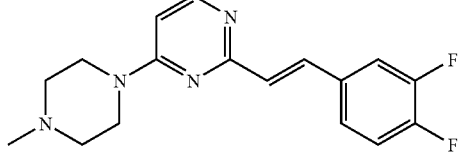 |
| 105 | 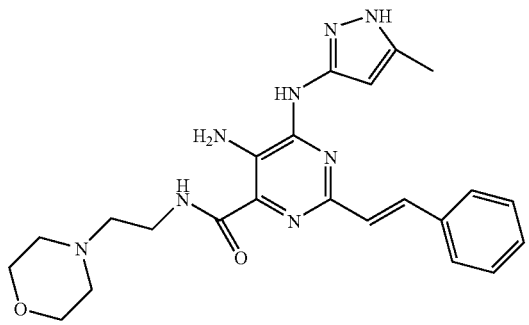 |
| 106 | 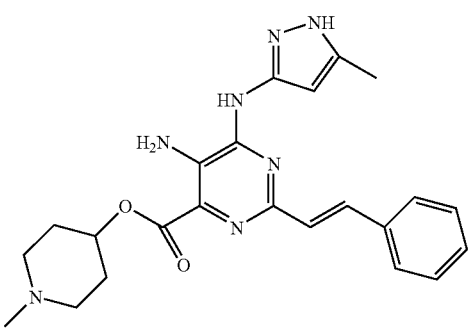 |
| 107 | 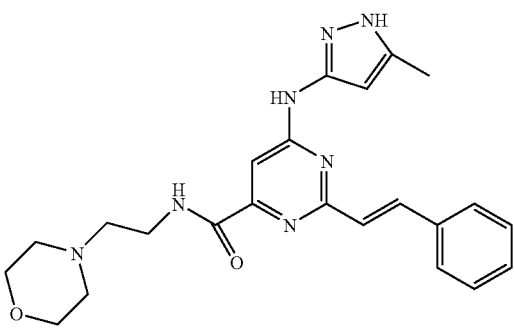 |

| Example No. | Structure |
|---|---|
| 108 | 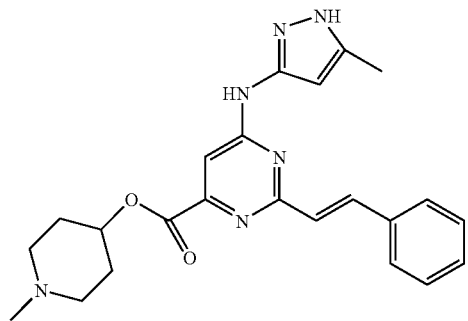 |
| 109 | 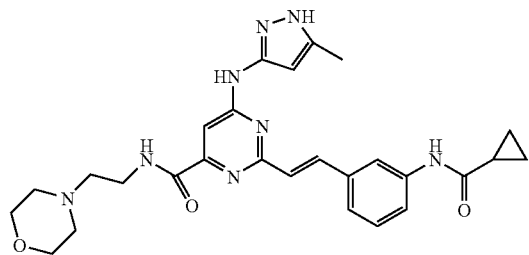 |
| 110 | 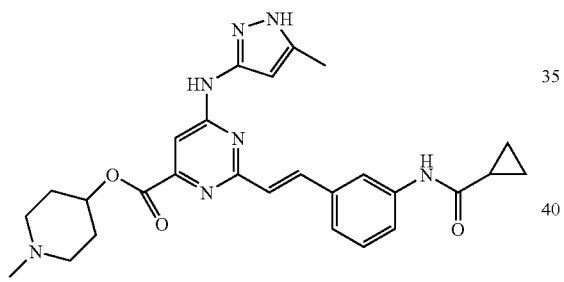 |
| 111 | 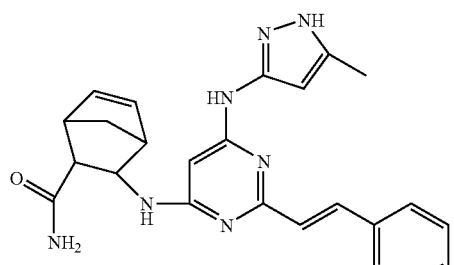 |
| 112 | 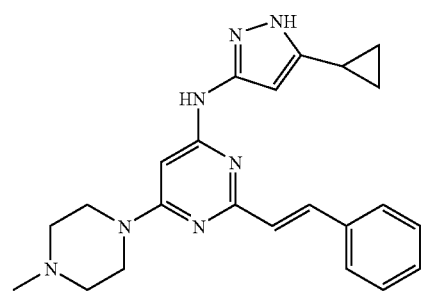 |
| Example No. | Structure |
|---|---|
| 113 | 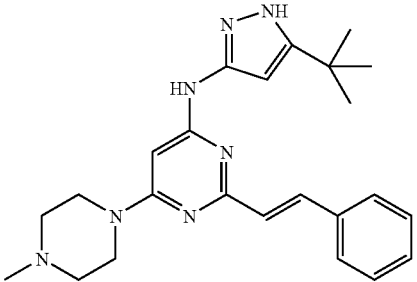 |
| 114 | 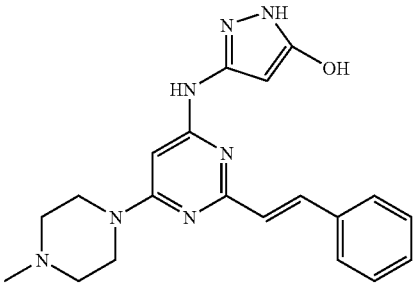 |
| 117 | 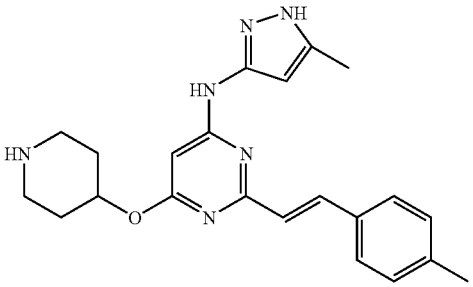 |
| 118 | 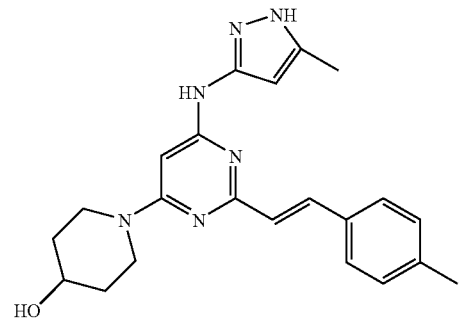 |
| 119 | 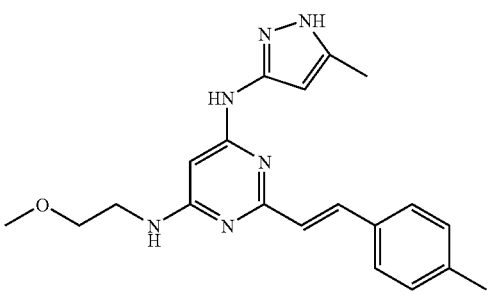 |

-continued
| Example No. | Structure |
|---|---|
| 120 | 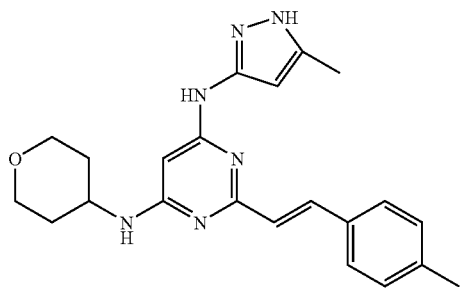 |
| 121 | 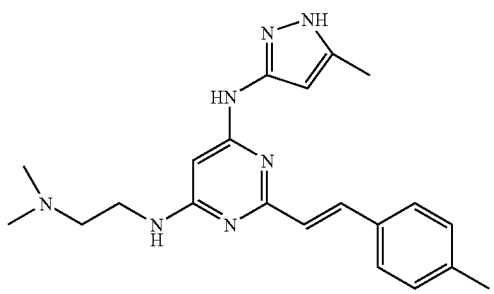 |
| 122 | 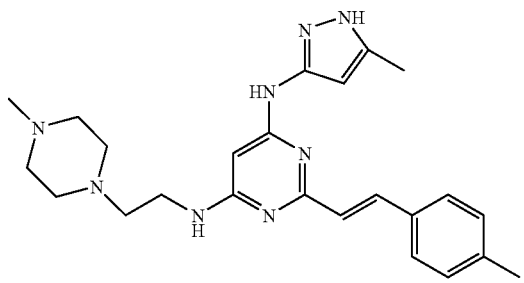 |
| 123 | 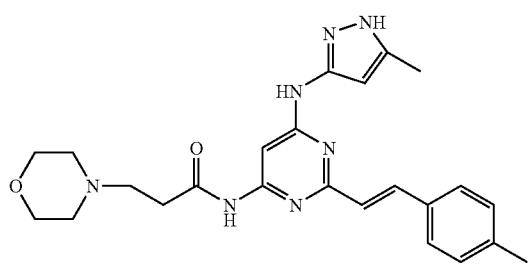 |
| 124 | 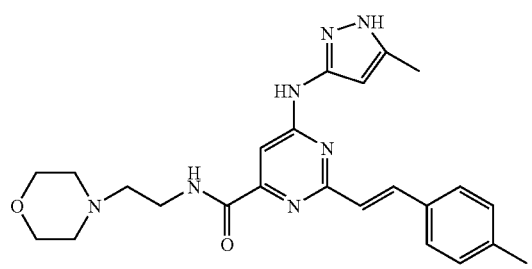 |
-continued
| Example No. | Structure |
|---|---|
| 125 | 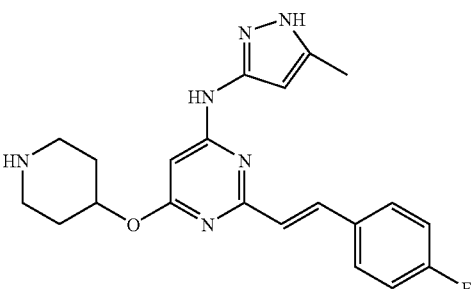 |
| 126 | 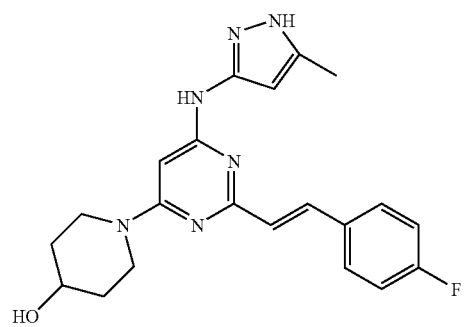 |
| 127 | 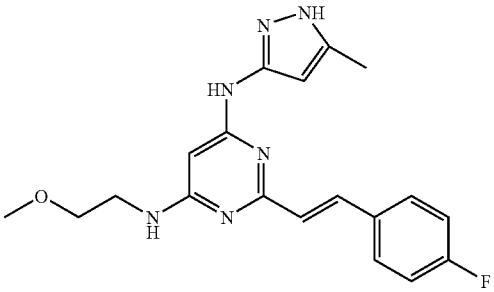 |
| 128 | 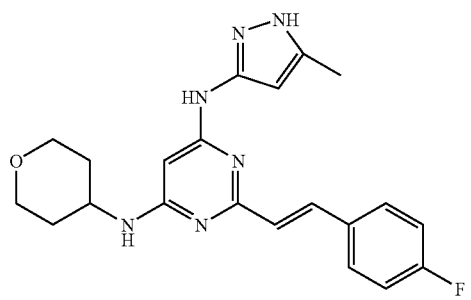 |
| 129 | 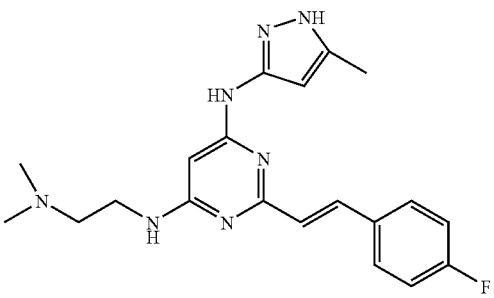 |

US 7,563,787 B2
159                                                               160
-continued                                                        -continued
| Example No. | Structure |
|---|---|
| 130 | 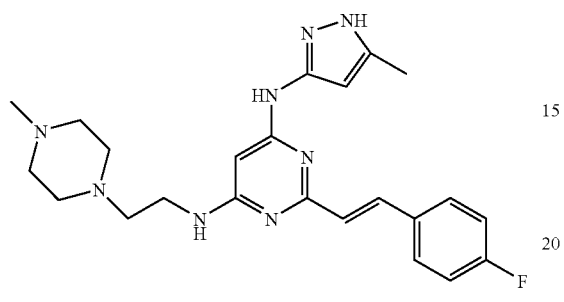 |
| 131 | 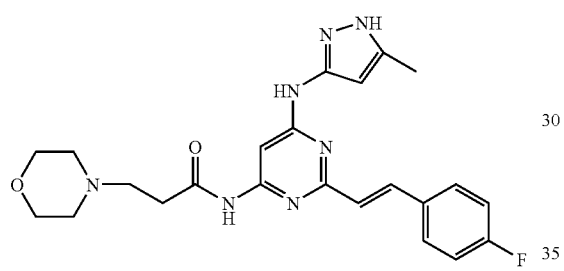 |
| 132 | 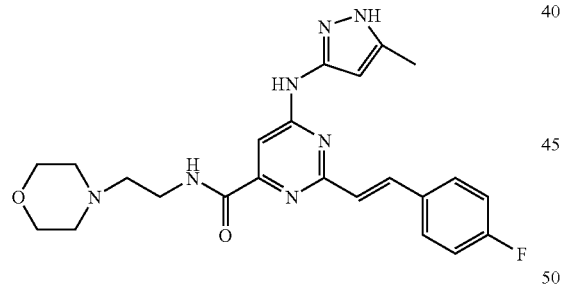 |
| 133 | 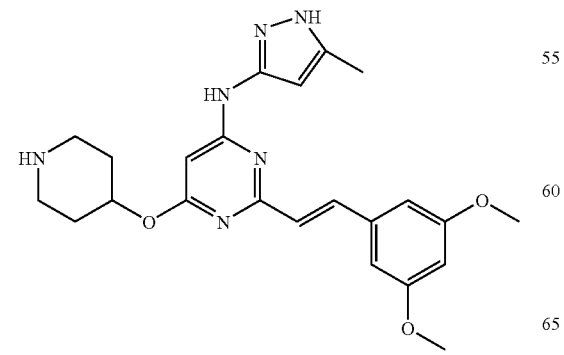 |
| Example No. | Structure |
|---|---|
| 134 | 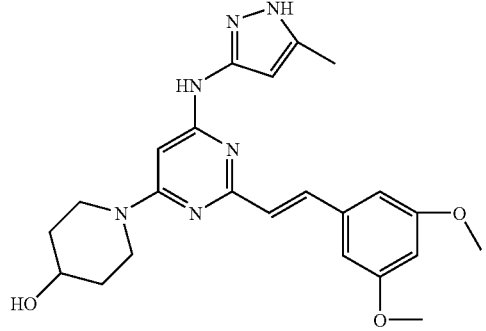 |
| 135 | 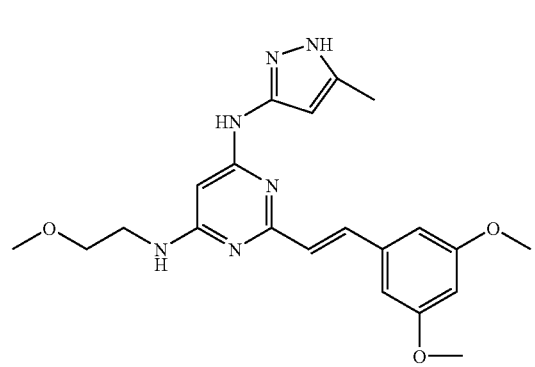 |
| 136 | 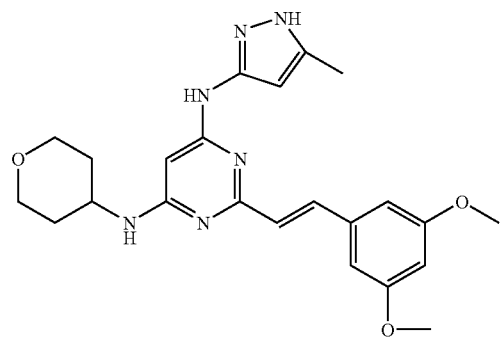 |
| 137 | 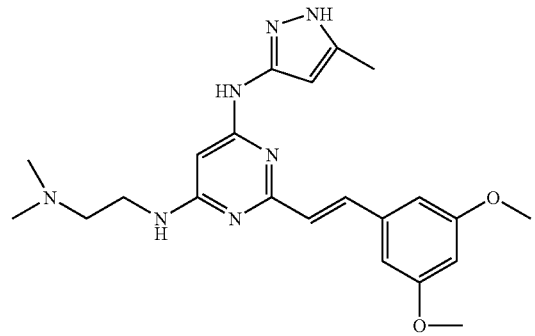 |

-continued
| Example No. | Structure |
|---|---|
| 138 | 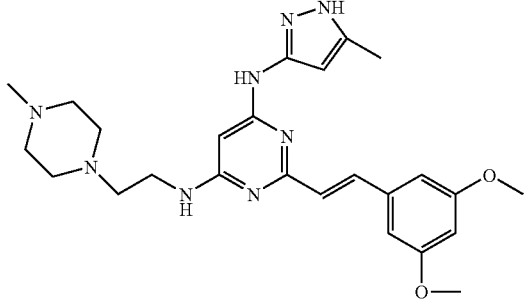 |
| 139 | 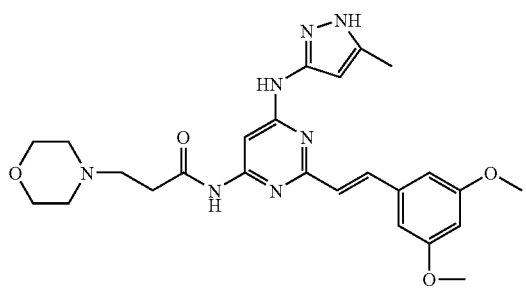 |
| 140 | 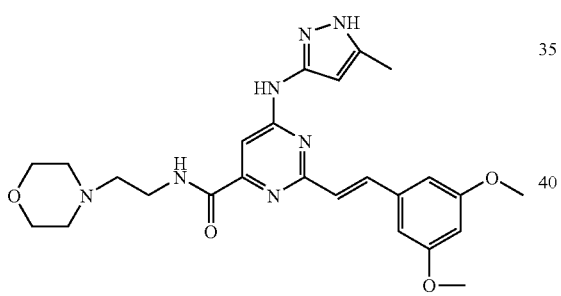 |
| 155 | 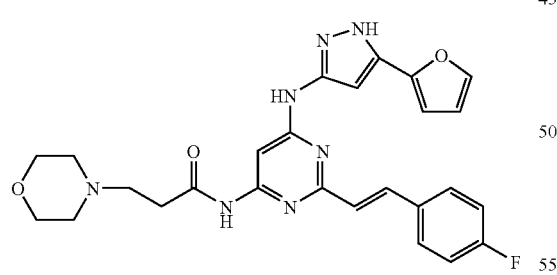 |
| 156 | 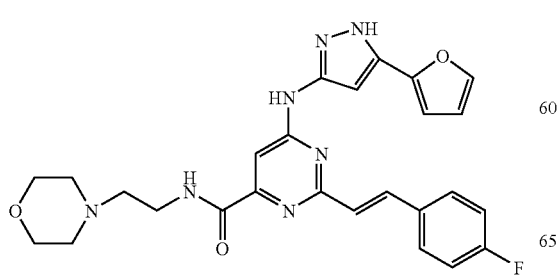 |
-continued
| Example No. | Structure |
|---|---|
| 157 | 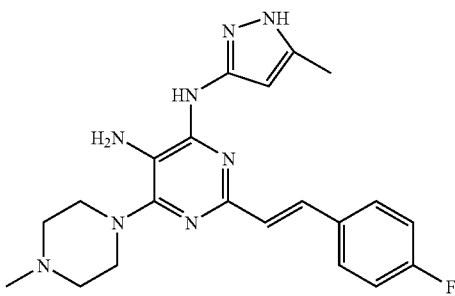 |
| 158 | 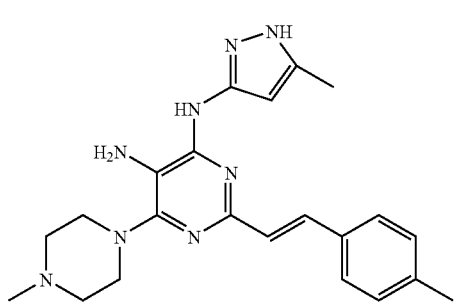 |
| 160 | 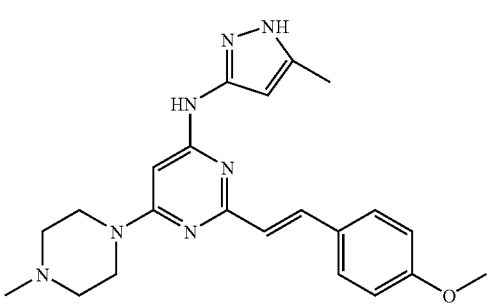 |
| 161 | 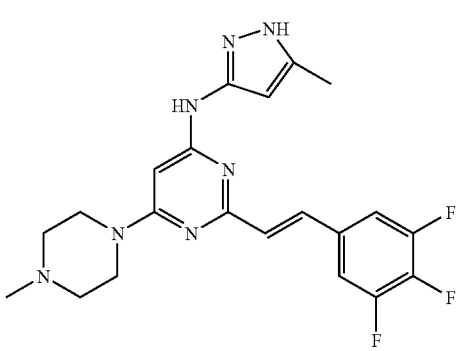 |
| 162 | 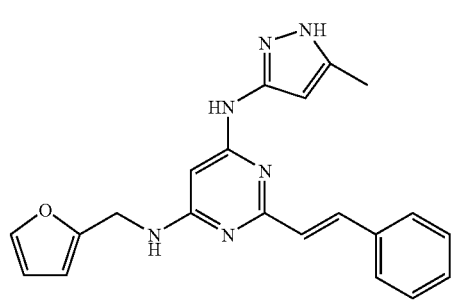 |

-continued
| Example No. | Structure |
|---|---|
| 163 | 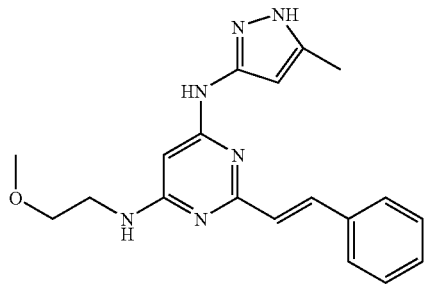 |
| 164 | 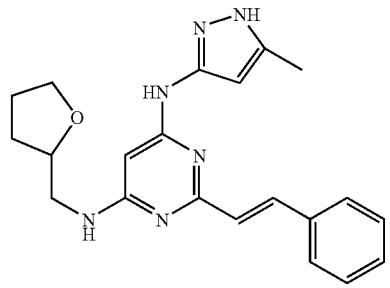 |
| 165 | 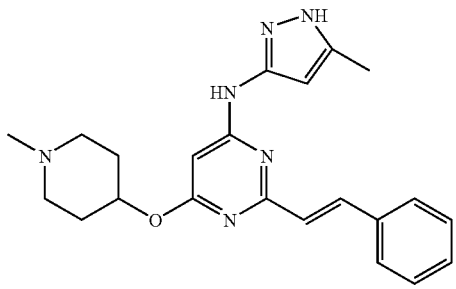 |
| 166 | 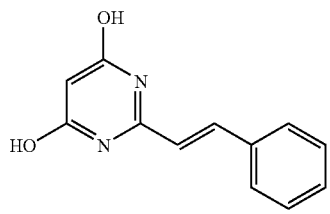 |
| 167 | 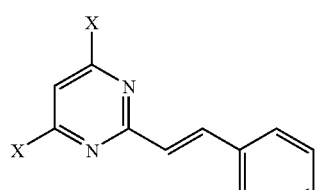<br>X = Cl, Br, I |
-continued
| Example No. | Structure |
|---|---|
| 168 | 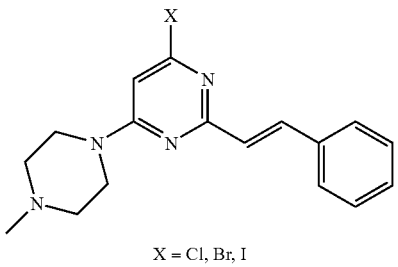<br>X = Cl, Br, I |
| 169 | 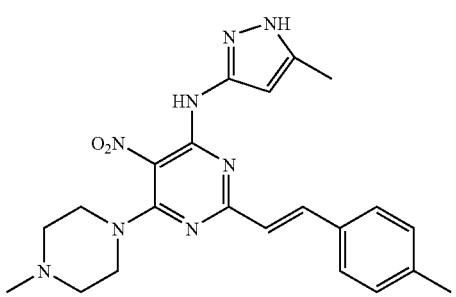 |
| 170 | 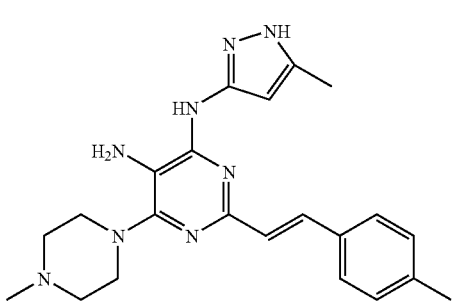 |
| 171 | 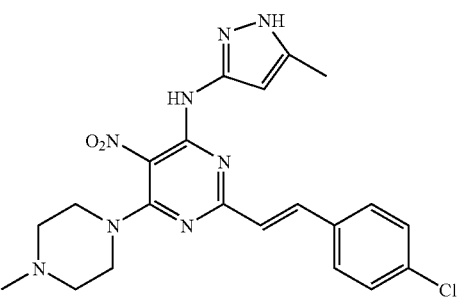 |
| 172 | 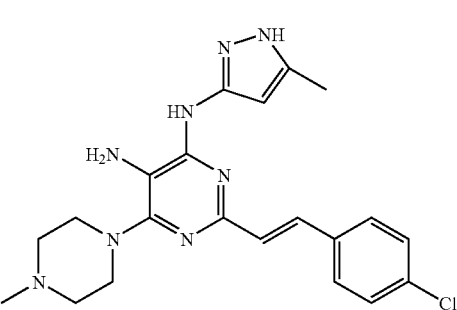 |

-continued

| Example No. | Structure |
|---|---|
| 173 | 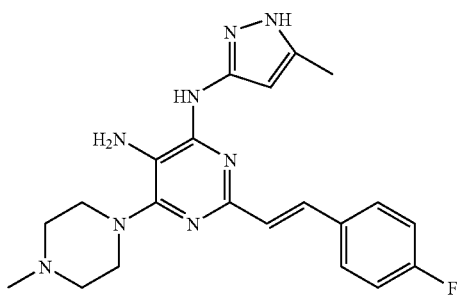 |
| 174 | 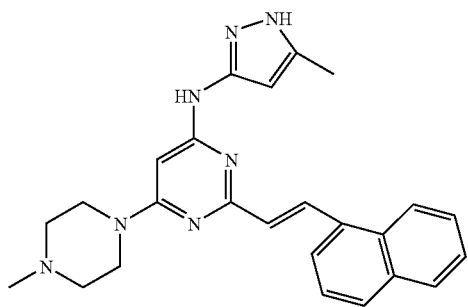 |
| 175 | 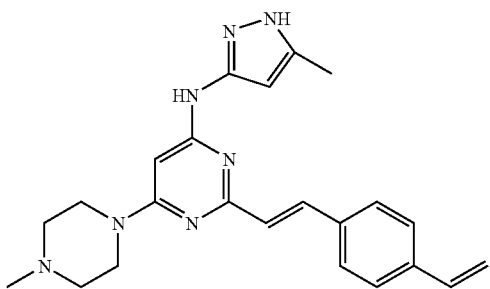 |

-continued

| Example No. | Structure |
|---|---|
| 176 | 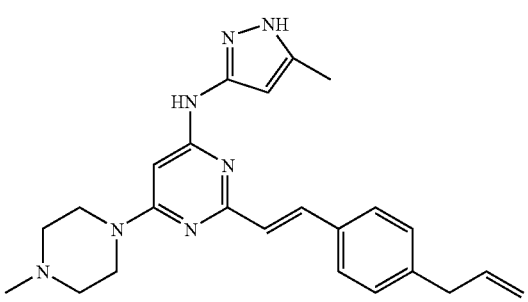 |
| 178 | 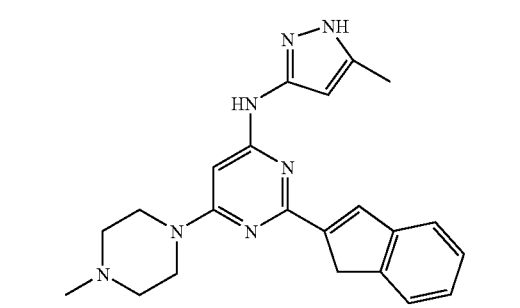 | or biologically acceptable salts thereof.

3. The composition of claim 2 wherein the composition comprises particles that are less than about 2 microns average particle size.

4. The composition of claim 2 wherein the composition is incorporated into a biodegradable or non-biodegradable polymer.

5. The composition of claim 2 comprising a compound selected from claim 2 and an additive.

6. The composition of claim 5 wherein the additive is selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

* * * * *

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Glu Ala Ile Tyr Ala Ala Pro Phe Ala Lys Lys Lys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Lys Val Glu Lys Ile Gly Glu Gly Thr Tyr Gly Val Val Tyr Lys
1               5                   10                  15